US010689716B1

(12) United States Patent
Daunert et al.

(10) Patent No.: US 10,689,716 B1
(45) Date of Patent: Jun. 23, 2020

(54) MATERIALS AND METHODS FOR DETECTING CORONAVIRUS

(71) Applicant: UNIVERSITY OF MIAMI, Miami, FL (US)

(72) Inventors: Sylvia Daunert, Miami, FL (US); Sapna K. Deo, Miami, FL (US); Jean-Marc Zingg, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 0 days.

(21) Appl. No.: 16/823,522

(22) Filed: Mar. 19, 2020

(51) Int. Cl.
 *C12Q 1/68* (2018.01)
 *C12Q 1/70* (2006.01)
(52) U.S. Cl.
 CPC .................. *C12Q 1/701* (2013.01)
(58) Field of Classification Search
 None
 See application file for complete search history.

(56) References Cited

U.S. PATENT DOCUMENTS

2018/0127815 A1* 5/2018 Belousov ............. C12Q 1/6823

FOREIGN PATENT DOCUMENTS

WO    WO 2016/141066    9/2016

OTHER PUBLICATIONS

NCBI Accession No. NC_045512.2, Jan. 13, 2020.*
Cheng et al, Diagnostic Testing for Severe Acute Respiratory Syndrome—Related Coronavirus-2: A Narrative Review, Ann Intern Med. 2020, DOI: 10.7326/M20-1301, Apr. 13, 2020.*
Corman et al., Detection of 2019 novel coronavirus (2019-nCoV) by real-time RT-PCR, Euro Surveill. Jan. 23, 2020; 25(3):2000045, doi: 10.2807/1560-7917.ES.2020.25.3.2000045.*
Yang et al., Point-of-Care RNA-Based Diagnostic Device for COVID-19, Diagnostics (Basel). Mar. 18, 2020;10(3). pii: E165. doi: 10.3390/diagnostics10030165.*
Loinc, SARS Coronavirus 2, available at https://loinc.org/sars-coronavirus-2/, accessed Apr. 29, 2020.*
ASM, False Negatives and Reinfections: the Challenges of SARS-CoV-2 RT-PCR Testing, available at https://asm.org/Articles/2020/April/False-Negatives-and-Reinfections-the-Challenges-of, Apr. 27, 2020, accessed Apr. 29, 2020.*
Jauset-Rubio et al., Ultrasensitive, rapid and inexpensive detection of DNA using paper based lateral flow assay, Sci Rep. Nov. 25, 2016;6:37732. doi: 10.1038/srep37732.*
Ivanov et al., Nucleic acid lateral flow assay with recombinase polymerase amplification: Solutions for highly sensitive detection of RNA virus, Talanta, vol. 210, 120616, DOI: 10.1016/j.talanta.2019.120616, Dec. 5, 2019.*
Banerjee et al., Fast, Efficient, and Stable Conjugation of Multiple DNA Strands on Colloidal Quantum Dots, *Bioconjug. Chem.* 26:1582-1589 (2015).
Banerjee et al., Quantum dots—DNA bioconjugates: synthesis to applications, *Interface Focus.* 6:20160064 (2016).
Barbieri et al., Detection of high-risk human papillomavirus type 16 and 18 using isothermal helicase-dependent amplification, *Diagnostic Microbiology and Infectious Disease.* 79:178-182 (2014).

(Continued)

*Primary Examiner* — Aaron A Priest
(74) *Attorney, Agent, or Firm* — Marshall, Gerstein & Borun LLP

(57) ABSTRACT

The disclosure relates to test kits and methods for detecting the presence of Coronavirus polynucleotides in a biological sample.

21 Claims, 3 Drawing Sheets

Specification includes a Sequence Listing.

```
NC_019843.3   GAGTATCTTAATTGATTTTAACGAAT---CTCAATTTCATTGTTATGGCATCC-------   28574
MN908947.3    TTGTTTTAGATTTCATCTAAACGAACAAACTAAAATGTCTGATAATGGACCCCA---AAA  28296
FJ882957.1    TTGTTTTAAA-------TAAACGAACAAATTAAAATGTCTGATAATGGACCCCAATCAAA  28138
              ** *    *        * ******     *  ** *    * *  ****    **

NC_019843.3   ----CCTGCTGCACCTCGTGCTGTTTCCTTTGCCGATAACAATGATATAACAAATACAAA  28630
MN908947.3    TCAGCGAAATGCACCCCG---CATTACGTTTGGTGGACCCTCAGATTCAACTGGCAGTAA  28353
FJ882957.1    CCAACGTAGTGCCCCCCG---CATTACATTTGGTGGACCCACAGATTCAACTGACAATAA  28195
                  *   ***  ** **    ** * ****  *   *   *** ***    *   **

NC_019843.3   CCTATCTCGAG---GTAGAGGACGTAATCCAAAACCACG---------AGCTGCACCAAA  28678
MN908947.3    CCAGAATGGAGAACGCAGTGGGGCGCGATCAAAACAACGTCGGCCCCAAGGTTTACCCAA  28413
FJ882957.1    CCAGAATGGAGGACGCAATGGGGCAAGGCCAAAACAGCGCCGACCCCAAGGTTTACCCAA  28255
                *     * ***  ** **      ******  **      ** *   *** ** **

NC_019843.3   TAACACTGTCTCTTGGTACACTGGGCTTACCCAACACGGGAAAGTCCCTCTTACCTTTCC  28738
MN908947.3    TAATACTGCCGTCTTGGTTCACCGCTCTCACTCAACATGGCAAGGAAGACCTTAAATTCCC  28473
FJ882957.1    TAATACTGCGTCTTGGTTCACAGCTCTCACTCAGCATGGCAAGGAGGAACTTAGATTCCC  28315
              *** ****  ******  *** *  ** ** ** ** ** *      ****   ** **

NC_019843.3   ACCTGGGCAGGGTGTACCTCTTAATGCCAATTCTACCCCTGCGCAAAATGCTGGGTATTG  28798
MN908947.3    TCGAGGACAAGGCGTTCCAATTAACACCAATAGCAGTCCAGATGACCAAATTGGCTACTA  28533
FJ882957.1    TCGAGGCCAGGGCGTTCCAATCAACACCAATAGTGGTCCAGATGACCAAATTGGCTACTA  28375
               *  ** ** ** ** ** **     * *  ***    *  *  *  ***  ** *
```

Alignment of MERS, 2019-nCoV, SARS

(56) References Cited

OTHER PUBLICATIONS

Jauset-Rubio et al., Ultrasensitive, rapid and inexpensive detection of DNA using paper based lateral flow assay, *Scientific Reports.* 6:37732 (2016).

Lin et al., Colorimetric Detection of 23 Human Papillomavirus Genotypes by Loop-Mediated Isothermal Amplification, *Clin. Lab.* 63:495-505 (2017).

Lu et al., Self-primed isothermal amplification for genomic DNA detection of human papillomavirus, *Biosensors & Bioelectronics.* 90:258-263 (2017).

Ma et al., Isothermal Method of a Recombinase Polymerase Amplification Assay for the Detection of Most Common High-Risk Human Papillomavirus Type 16 and Type 18 DNA, *Clin. Lab.* 63:27-38 (2017).

Mahmoodi et al., Early detection of cervical cancer based on high-risk HPV DNA-based genosensors: A systematic review, *BioFactors.* 45:101-117 (2019).

Rodriguez et al., Paper-Based RNA Extraction, in Situ Isothermal Amplification, and Lateral Flow Detection for Low-Cost, Rapid Diagnosis of Influenza A (H1N1) from Clinical Specimens, *Analytical Chemistry.* 87:7872-7879 (2015).

Sheridan, C, Coronavirus and the race to distribute reliable diagnostics, *Nature Biotechnology.* 38:382-4 (2020).

Song et al., Two-Stage Isothermal Enzymatic Amplification for Concurrent Multiplex Molecular Detection, *Clinical Chemistry.* 63:495-505 (2017).

Stringer et al., TwistAmp Liquid: a versatile amplification method to replace PCR, *Nature Methods.* 15: 1-3 (2018).

Zhang et al., A paper-based platform for detection of viral RNA, *The Analyst.* 142:815-823 (2017).

Zhang et al., Recent advances in the detection of respiratory virus infection in humans, *J. Med. Virol.* 92:408-17 (2020).

Zingg et al., Trinucleotide Rolling Circle Amplification: A Novel Method for the Detection of RNA and DNA, *Methods and Protocols.* 1:15 (2018).

\* cited by examiner

```
NC_019843.3   GAGTATCTTAATTGATTTTAACGAAT---CTCAATTTCATTGTTATGGCATCC-------    28574
MN908947.3    TTGTTTTAGATTTCATCTAAACGAACAAACTAAAATGTCTGATAATGGACCCCA---AAA   28296
FJ882957.1    TTGTTTTAAA---------TAAACGAACAAATTAAAATGTCTGATAATGGACCCCAATCAAA 28138
              **  *   *          *  *****    *  ** *  *  ****  **

NC_019843.3   ----CCTGCTGCACCTCGTGCTGTTTCCTTTGCCGATAACAATGATATAACAAATACAAA  28630
MN908947.3    TCAGCGAAATGCACCCCG---CATTACGTTTGGTGGACCCTCAGATTCAACTGGCAGTAA  28353
FJ882957.1    CCAACGTAGTGCCCCCCG---CATTACATTTGGTGGACCCACAGATTCAACTGACAATAA  28195
                *   ***  ** **      ** * ****   *   *    ***  ***     *  **

NC_019843.3   CCTATCTCGAG---GTAGAGGACGTAATCCAAAACCACG---------AGCTGCACCAAA  28678
MN908947.3    CCAGAATGGAGAACGCAGTGGGGCGCGATCAAAACAACGTCGGCCCCAAGGTTTACCCAA  28413
FJ882957.1    CCAGAATGGAGGACGCAATGGGGCAAGGCCAAAACAGCGCCGACCCCAAGGTTTACCCAA  28255
              **    *   *      *  *    *  *     ******  **     **  *  *** **

NC_019843.3   TAACACTGTCTCTTGGTACACTGGGCTTACCCAACACGGGAAAGTCCCTCTTACCTTTCC  28738
MN908947.3    TAATACTGCGTCTTGGTTCACCGCTCTCACTCAACATGGCAAGGAAGACCTTAAATTCCC  28473
FJ882957.1    TAATACTGCGTCTTGGTTCACAGCTCTCACTCAGCATGGCAAG GAGGAACTTAGATTCCC  28315
              *** ****  ******* ***  *   *   **  ** **  **       ****  ** **

NC_019843.3   ACCTGGGCAGGGTGTACCTCTTAATGCCAATTCTACCCCTGCGCAAAATGCTGGGTATTG  28798
MN908947.3    TCGAGGACAAGGCGTTCCAATTAACACCAATAGCAGTCCAGATGACCAAATTGGCTACTA  28533
FJ882957.1    TCGAGGCCAGGGCGTTCCAATCAACACCAATAGTGGTCCAGATGACCAAATTGGCTACTA  28375
              *   ** **  **  ** **  **  ** *****    *   **    *  *** ** *
```

Figure 1: Alignment of MERS, 2019-nCoV, SARS 2019-nCoV plasmid copies in assay

Figure 2: Limit of detection of SARS-CoV-2 rapid RPA method

SEQUENCE LISTING

```
<160> NUMBER OF SEQ ID NOS: 13

<210> SEQ ID NO 1
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 1
tctgataatg gaccccaaaa tcagcgaaat                                        30

<210> SEQ ID NO 2
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 2
acgccttgtc ctcgagggaa tttaaggtct                                        30

<210> SEQ ID NO 3
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 3
ggtaaacctt ggggccgacg ttgttttgat                                        30

<210> SEQ ID NO 4
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 4
```
tctgataatg gaccccaaaa tcagcgaaat                                              30

<210> SEQ ID NO 5
<211> LENGTH: 30
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' - FAM

<400> SEQUENCE: 5
acgccttgtc ctcgagggaa tttaaggtct                                              30

<210> SEQ ID NO 6
<211> LENGTH: 46
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (16)..(16)
<223> OTHER INFORMATION: SpacerC3

<400> SEQUENCE: 6
gttttcccag tcagactctg ataatggacc ccaaaatcag cgaaat                            46

<210> SEQ ID NO 7
<211> LENGTH: 15
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Biotin

<400> SEQUENCE: 7
gcgatcaaaa caacg                                                              15

<210> SEQ ID NO 8
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (25)..(25)
<223> OTHER INFORMATION: 3' Biotin TEG

<400> SEQUENCE: 8
gtcgtgactg ggaaaacttt ttttt                                                   25

<210> SEQ ID NO 9
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 9
attcatcgat gataatacga ctcactatag gagggttgcg tttgaga                           47

<210> SEQ ID NO 10
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 10

```
taatgcagct ggcacgacag gt                                              22
```

<210> SEQ ID NO 11
<211> LENGTH: 30119
<212> TYPE: DNA
<213> ORGANISM: MERS-CoV

<400> SEQUENCE: 11

```
gatttaagtg aatagcttgg ctatctcact tccccctcgtt ctcttgcaga actttgattt    60
taacgaactt aaataaaagc cctgttgttt agcgtatcgt tgcacttgtc tggtgggatt    120
gtggcattaa tttgcctgct catctaggca gtggacatat gctcaacact gggtataatt    180
ctaattgaat actatttttc agttagagcg tcgtgtctct tgtacgtctc ggtcacaata    240
cacggtttcg tccggtgcgt ggcaattcgg ggcacatcat gtcttcgtg gctggtgtga    300 ccgcgcaagg tgcgcgcggt acgtatcgag cagcgctcaa ctctgaaaaa catcaagacc    360
atgtgtctct aactgtgcca ctctgtggtt caggaaacct ggttgaaaaa ctttcaccat    420
ggttcatgga tggcgaaaat gcctatgaag tggtgaaggc catgttactt aaaaaggagc    480
cacttctcta tgtgcccatc cggctggctg acacactag acacctccca ggtcctcgtg    540
tgtacctggt tgagaggctc attgcttgtg aaaatccatt catggttaac caattggctt    600
atagctctag tgcaaatggc agcctggttg cacaactttt gcagggcaag cctattggta    660
tgttcttccc ttatgacatc gaacttgtca caggaaagca aaatattctc ctgcgcaagt    720
atggccgtgg tggttatcac tacacccat tccactatga gcgagacaac acctcttgcc    780
ctgagtggat ggacgatttt gaggcggatc ctaaaggcaa atatgcccag aatctgctta    840
agaagttgat tggcggtgat gtcactccag ttgaccaata catgtgtggc gttgatggaa    900 acccattag tgcctacgca tttttaatgg ccaaggatgg aataaccaaa ctggctgatg    960
ttgaagcgga cgtcgcagca cgtgctgatg acgaaggctt catcacatta agaacaatc    1020 tatatagatt ggtttggcat gttgagcgta aagacgttcc atatcctaag caatctattt    1080
ttactattaa tagtgtggtc caaaaggatg gtgttgaaaa cactcctcct cactattta    1140 ctcttggatg caaaattta acgctcaccc cacgcaacaa gtggagtggc gtttctgact    1200
tgtccctcaa acaaaaactc ctttacacct tctatggtaa ggagtcactt gagaacccaa    1260
cctacattta ccactccgca ttcattgagt gtggaagttg tggtaatgat tcctggctta    1320
cagggaatgc tatccaaggg tttgcctgtg gatgtgggc atcatataca gctaatgatg    1380
tcgaagtcca atcatctggc atgattaagc caaatgctct tctttgtgct acttgcccct    1440
ttgctaaggg tgatagctgt tcttctaatt gcaaacattc agttgctcag ttggttagtt    1500 accttctga cgctgtaat gttattgctg attctaagtc cttcacactt atctttggtg    1560
gcgtagctta cgcctacttt ggatgtgagg aaggtactat gtactttgtg cctagagcta    1620
agtctgttgt ctcaaggatt ggagactcca tctttacagg ctgtactggc tcttggaaca    1680
aggtcactca aattgctaac atgttcttgg aacagactca gcattccctt aactttgtgg    1740
gagagttcgt tgtcaacgat gttgtcctcg caattctctc tggaaccaca actaatgttg    1800
```

```
acaaaatacg ccagcttctc aaaggtgtca cccttgacaa gttgcgtgat tatttagctg   1860
actatgacgt agcagtcact gccggcccat tcatggaata tgctattaat gttggtggta   1920
caggattaca gtatgccgcc attactgcac cttatgtagt tctcactggc ttaggtgagt   1980
cctttaagaa agttgcaacc ataccgtata aggtttgcaa ctctgttaag gatactctgg   2040
cttattatgc tcacagcgtg ttgtacagag ttttttcctta tgacatggat tctggtgtgt   2100
catcctttag tgaactactt tttgattgcg ttgatctttc agtagcttct acctattttt   2160
tagtccgcat cttgcaagat aagactggcg actttatgtc tacaattatt acttcctgcc   2220
aaactgctgt tagtaagctt ctagatacat gttttgaagc tacagaagca acatttaact   2280
tcttgttaga tttggcagga ttgttcagaa tctttctccg caatgcctat gtgtacactt   2340
cacaagggtt tgtggtggtc aatggcaaag tttctacact tgtcaaacaa gtgttagact   2400
tgcttaataa gggtatgcaa cttttgcata caaaggtctc ctgggctggt tctaaaatca   2460
ttgctgttat ctacagcggc agggagtctc taatattccc atcgggaacc tattactgtg   2520
tcaccactaa ggctaagtcc gttcaacaag atcttgacgt tattttgcct ggtgagtttt   2580
ccaagaagca gttaggactg ctccaaccta ctgacaattc tacaactgtt agtgttactg   2640
tatccagtaa catggttgaa actgttgtgg gtcaacttga gcaaactaat atgcatagtc   2700
ctgatgttat agtaggtgac tatgtcatta ttagtgaaaa attgtttgtg cgtagtaagg   2760
aagaagacgg atttgccttc taccctgctt gcactaatgg tcatgctgta ccgactctct   2820
ttagacttaa gggaggtgca cctgtaaaaa aagtagcctt tggcggtgat caagtacatg   2880
aggttgctgc tgtaagaagt gttactgtcg agtacaacat tcatgctgta ttagacacac   2940
tacttgcttc ttctagtctt agaacctttg ttgtagataa gtctttgtca attgaggagt   3000
ttgctgacgt agtaaaggaa caagtctcag acttgcttgt taaattactg cgtggaatgc   3060
cgattccaga ttttgattta gacgatttta ttgacgcacc atgctattgc tttaacgctg   3120
agggtgatgc atcctggtct tctactatga tcttctctct tcaccccgtc gagtgtgacg   3180
aggagtgttc tgaagtagag gcttcagatt tagaagaagg tgaatcagag tgcatttctg   3240
agacttcaac tgaacaagtt gacgtttctc atgagacttc tgacgacgag tgggctgctg   3300
cagttgatga agcgttccct ctcgatgaag cagaagatgt tactgaatct gtgcaagaag   3360
aagcacaacc agtagaagta cctgttgaag atattgcgca ggttgtcata gctgacacct   3420
tacaggaaac tcctgttgtg cctgatactg ttgaagtccc accgcaagtg gtgaaacttc   3480
cgtctgcacc tcagactatc cagcccgagg taaaagaagt tgcacctgtc tatgaggctg   3540
ataccgaaca gacacagaat gttactgtta aacctaagag gttacgcaaa agcgtaatg   3600 ttgaccctt tgtccaatttt gaacataagg ttattacaga gtgcgttacc atagtttag   3660 gtgacgcaat tcaagtagcc aagtgctatg gggagtctgt gttagttaat gctgctaaca   3720
cacatcttaa gcatgcggt ggtatcgctg gtgctattaa tgcggcttca aaaggggctg   3780
tccaaaaaga gtcagatgag tatattctgg ctaaagggcc gttacaagta ggagattcag   3840
ttctcttgca aggccattct ctagctaaga atatcctgca tgtcgtaggc ccagatgccc   3900
gcgctaaaca ggatgtttct ctccttagta agtgctataa ggctatgaat gcatatcctc   3960
ttgtagtcac tcctcttgtt tcagcaggca tatttggtgt aaaaccagct gtgtcttttg   4020
attatcttat tagggaggct aagactagag ttttagtcgt cgttaattcc caagatgtct   4080
ataagagtct taccatagtt gacattccac agagtttgac ttttttcatat gatgggttac   4140
```

```
gtggcgcaat acgtaaagct aaagattatg gtttactgt ttttgtgtgc acagacaact   4200
ctgctaacac taaagttctt aggaacaagg gtgttgatta tactaagaag tttcttacag   4260
ttgacggtgt gcaatattat tgctacacgt ctaaggacac tttagatgat atcttacaac   4320
aggctaataa gtctgttggt attatatcta tgcctttggg atatgtgtct catggtttag   4380
acttaatgca agcagggagt gtcgtgcgta gagttaacgt gccctacgtg tgtctcctag   4440
ctaataaaga gcaagaagct attttgatgt ctgaagacgt taagttaaac ccttcagaag   4500
attttataaa gcacgtccgc actaatggtg gttacaattc ttggcattta gtcgagggtg   4560
aactattggt gcaagactta cgcttaaata agctcctgca ttggtctgat caaaccatat   4620
gctacaagga tagtgtgttt tatgttgtaa agaatagtac agcttttcca tttgaaacac   4680
tttcagcatg tcgtgcgtat ttggattcac gcacgacaca gcagttaaca atcgaagtct   4740
tagtgactgt cgatggtgta aattttagaa cagtcgttct aaataataag aacacttata   4800
gatcacagct tggatgcgtt ttctttaatg gtgctgatat ttctgacacc attcctgatg   4860
agaaacagaa tggtcacagt ttatatctag cagacaattt gactgctgat gaaacaaagg   4920
cgcttaaaga gttatatggc cccgttgatc ctactttctt acacagattc tattcactta   4980
aggctgcagt ccatgggtgg aagatggttg tgtgtgataa ggtacgttct ctcaaattga   5040
gtgataataa ttgttatctt aatgcagtta ttatgacact tgatttattg aaggacatta   5100
aatttgttat acctgctcta cagcatgcat ttatgaaaca taagggcggt gattcaactg   5160
acttcatagc cctcattatg gcttatggca attgcacatt tggtgctcca gatgatgcct   5220
ctcggttact tcataccgtg cttgcaaagg ctgagttatg ctgttctgca cgcatggttt   5280
ggagagagtg gtgcaatgtc tgtggcataa aagatgttgt tctacaaggc ttaaaagctt   5340
gttgttacgt gggtgtgcaa actgttgaag atctgcgtgc tcgcatgaca tatgtatgcc   5400
agtgtggtgg tgaacgtcat cggcaattag tcgaacacac cacccctgg ttgctgctct   5460 caggcacacc aaatgaaaaa ttggtgacaa cctccacggc gcctgatttt gtagcattta   5520
atgtctttca gggcattgaa acggctgttg gccattatgt tcatgctcgc ctgaagggtg   5580
gtcttatttt aaagtttgac tctggcaccg ttagcaagac ttcagactgg aagtgcaagg   5640
tgacagatgt acttttccc ggccaaaaat acagtagcga ttgtaatgtc gtacggtatt   5700
ctttggacgg taatttcaga acagaggttg atcccgacct atctgctttc tatgttaagg   5760
atggtaaata ctttacaagt gaaccacccg taacatattc accagctaca attttagctg   5820
gtagtgtcta cactaatagc tgccttgtat cgtctgatgg acaacctggc ggtgatgcta   5880
ttagtttgag ttttaataac ctttagggt ttgattctag taaaccagtc actaagaaat   5940
acacttactc cttcttgcct aaagaagacg gcgatgtgtt gttggctgag tttgacactt   6000
atgaccctat ttataagaat ggtgccatgt ataaaggcaa accaattctt tgggtcaata   6060
aagcatctta tgatactaat cttaataagt tcaatagagc tagtttgcgt caaatttttg   6120
acgtagcccc cattgaactc gaaaataaat tcacaccttt gagtgtggag tctacaccag   6180
ttgaacctcc aactgtagat gtggtagcac ttcaacagga aatgacaatt gtcaaatgta   6240
agggttaaaa taaccctttc gtgaaggaca atgtcagttt cgttgctgat gattcaggta   6300
ctcccgttgt tgagtatctg tctaaagaag acctacatac attgtatgta gaccctaagt   6360
atcaagtcat tgtcttaaaa gacaatgtac ttcttctat gcttagattg cacaccgttg   6420
agtcaggtga tattaacgtt gttgcagctt ccgatcttt gacacgtaaa gtgaagttac   6480
tatttagggc ttcattttat ttcaaagaat ttgctacccg cactttcact gctaccactg   6540
```

```
ctgtaggtag ttgtataaag agtgtagtgc ggcatctagg tgttactaaa ggcatattga   6600
caggctgttt tagttttgcc aagatgttat ttatgcttcc actagcttac tttagtgatt   6660
caaaactcgg caccacagag gttaaagtga gtgctttgaa aacagccggc gttgtgacag   6720
gtaatgttgt aaaacagtgt tgcactgctg ctgttgattt aagtatggat aagttgcgcc   6780
gtgtggattg gaaatcaacc ctacggttgt tacttatgtt atgcacaact atggtattgt   6840
tgtcttctgt gtatcacttg tatgtcttca atcaggtctt atcaagtgat gttatgtttg   6900
aagatgccca aggtttgaaa aagttctaca agaagttag agcttaccta ggaatctctt   6960
ctgcttgtga cggtcttgct tcagcttata gggcgaattc cttttgatgta cctacattct   7020 gcgcaaaccg ttctgcaatg tgtaattggt gcttgattag ccaagattcc ataactcact   7080
acccagctct taagatggtt caaacacatc ttagccacta tgttcttaac atagattggt   7140
tgtggtttgc atttgagact ggtttggcat acatgctcta tacctcggcc ttcaactggt   7200
tgttgttggc aggtacattg cattatttct ttgcacagac ttccatattt gtagactggc   7260
ggtcatacaa ttatgctgtg tctagtgcct tctggttatt cacccacatt ccaatggcgg   7320
gtttggtacg aatgtataat ttgttagcat gcctttggct tttacgcaag ttttatcagc   7380
atgtaatcaa tggttgcaaa gatacggcat gcttgctctg ctataagagg aaccgactta   7440
ctagagttga agcttctacc gttgtctgtg gtggaaaacg tacgttttat atcacagcaa   7500
atggcggtat ttcattctgt cgtaggcata attggaattg tgtggattgt gacactgcag   7560
gtgtggggaa taccttcatc tgtgaagaag tcgcaaatga cctcactacc gccctacgca   7620
ggcctattaa cgctacggat agatcacatt attatgtgga ttccgttaca gttaaagaga   7680
ctgttgttca gtttaattat cgtagagacg gtcaaccatt ctacgagcgg tttcccctct   7740
gcgcttttac aaatctagat aagttgaagt tcaaagaggt ctgtaaaact actactggta   7800
tacctgaata caactttatc atctacgact catcagatcg tggccaggaa agtttagcta   7860
ggtctgcatg tgtttattat tctcaagtct tgtgtaaatc aattcttttg gttgactcaa   7920
gtttggttac ttctgttggt gattctagtg aaatcgccac taaaatgttt gattcctttg   7980
ttaatagttt cgtctcgctg tataatgtca cacgcgataa gttggaaaaa cttatctcta   8040
ctgctcgtga tggcgtaagg cgaggcgata acttccatag tgtcttaaca acattcattg   8100
acgcagcacg aggccccgca ggtgtggagt ctgatgttga gaccaatgaa attgttgact   8160
ctgtgcagta tgctcataaa catgacatac aaattactaa tgagagctac aataattatg   8220
taccctcata tgttaaacct gatagtgtgt ctaccagcga tttaggtagt ctcattgatt   8280
gtaatgcggc ttcagttaac caaattgtct tgcgtaattc taatggtgct tgcatttgga   8340
acgctgctgc atatatgaaa ctctcggatg cacttaaacg acagattcgc attgcatgcc   8400
gtaagtgtaa tttagctttc cggttaacca cctcaaagct acgcgctaat gataatatct   8460
tatcagttag attcactgct aacaaaattg ttggtggtgc tcctacatgg tttaatgcgt   8520
tgcgtgactt tacgttaaag ggttatgttc ttgctaccat tattgtgttt ctgtgtgctg   8580
tactgatgta tttgtgttta cctacatttt ctatggcacc tgttgaattt tatgaagacc   8640
gcatcttgga ctttaaagtt cttgataatg gtatcattag ggatgtaaat cctgatgata   8700
agtgctttgc taataagcac cggtccttca cacaatggta tcatgagcat gttggtggtg   8760
tctatgacaa ctctatcaca tgcccattga cagttgcagt aattgctgga gttgctggtg   8820
ctcgcattcc agacgtacct actacattgg cttgggtgaa caatcagata atttctctttg   8880
```

```
tttctcgagt ctttgctaat acaggcagtg tttgctacac tcctatagat gagatacact      8940
ataagagttt ctctgatagt ggttgcattc ttccatctga gtgcactatg tttagggatg      9000
cagagggccg tatgacacca tactgccatg atcctactgt tttgcctggg cttttgcgt       9060
acagtcagat gaggcctcat gttcgttacg acttgtatga tggtaacatg tttattaaat     9120
ttcctgaagt agtatttgaa agtacactta ggattactag aactctgtca actcagtact     9180
gccggttcgg tagttgtgag tatgcacaag agggtgtttg tattaccaca aatggctcgt     9240
gggccatttt taatgaccac catcttaata gacctggtgt ctattgtggc tctgattta     9300
ttgacattgt caggcggtta gcagtatcac tgttccagcc tattacttat ttccaattga     9360
ctacctcatt ggtcttgggt ataggtttgt gtgcgttcct gactttgctc ttctattata     9420
ttaataaagt aaaacgtgct tttgcagatt acacccagtg tgctgtaatt gctgttgttg      9480
ctgctgttct taatagcttg tgcatctgct ttgttacctc tataccattg tgtatagtac      9540
cttacactgc attgtactat tatgctacat tctattttac taatgagcct gcatttatta      9600
tgcatgtttc ttggtacatt atgttcgggc ctatcgttcc catatggatg acctgcgtct     9660
atacagttgc aatgtgcttt agacacttct tctgggtttt agcttatttt agtaagaaac     9720
atgtagaagt ttttactgat ggtaagctta attgtagttt ccaggacgct gcctctaata     9780
tctttgttat taacaaggac acttatgcag ctcttagaaa ctctttaact aatgatgcct     9840
attcacgatt tttggggttg tttaacaagt ataagtactt ctctggtgct atggaaacag     9900
ccgcttatcg tgaagctgca gcatgtcatc ttgctaaagc cttacaaaca tacagcgaga     9960
ctggtagtga tcttctttac caaccaccca actgtagcat aacctctggc gtgttgcaaa    10020
gcggtttggt gaaaatgtca catcccagtg gagatgttga ggcttgtatg gttcaggtta    10080
cctgcggtag catgactctt aatggtcttt ggcttgacaa cacagtctgg tgcccacgac    10140
acgtaatgtg cccggctgac cagttgtctg atcctaatta tgatgccttg ttgatttcta    10200
tgactaatca tagtttcagt gtgcaaaaac acattggcgc tccagcaaac ttgcgtgttg    10260
ttggtcatgc catgcaaggc actctttttga agttgactgt cgatgttgct aaccctagca    10320
ctccagccta cacttttaca acagtgaaac ctggcgcagc atttagtgtg ttagcatgct    10380
ataatggtcg tccgactggt acattcactg ttgtaatgcg ccctaactac acaattaagg    10440
gttcctttct gtgtggttct tgtggtagtt tggttacac caaggagggt agtgtgatca     10500
attctgtta catgcatcaa atggaacttg ctaatggtac acataccggt tcagcatttg    10560
atggtactat gtatggtgcc tttatggata aacaagtgca ccaagttcag ttaacagaca    10620
aatactgcag tgttaatgta gtagcttggc tttacgcagc aatacttaat ggttgcgctt    10680
ggtttgtaaa acctaatcgc actagtgttg tttcttttaa tgaatgggct cttgccaacc    10740
aattcactga atttgttggc actcaatccg ttgacatgtt agctgtcaaa acaggcgttg    10800
ctattgaaca gctgctttat gcgatccaac aactgtatac tgggttccag ggaaagcaaa    10860
tccttggcag taccatgttg gaagatgaat tcacacctga ggatgttaat atgcagatta    10920
tgggtgtggt tatgcagagt ggtgtgagaa agttacata tggtactgcg cattggttgt    10980
ttgcgacccc tgtctcaacc tatgtgataa tcttacaagc cactaaattt actttgtgga    11040
actacttgtt tgagactatt cccacacagt tgttcccact cttatttgtg actatggcct    11100
tcgttatgtt gttggttaaa cacaaacaca ccttttgac acttttcttg ttgcctgtgg    11160
ctatttgttt gacttatgca aacatagtct acgagcccac tactcccatt tcgtcagcgc    11220
tgattgcagt tgcaaattgg cttgccccca ctaatgctta tatgcgcact acacatactg    11280
```

```
atattggtgt ctacattagt atgtcacttg tattagtcat tgtagtgaag agattgtaca    11340
acccatcact ttctaacttt gcgttagcat tgtgcagtgg tgtaatgtgg ttgtacactt    11400
atagcattgg agaagcctca agccccattg cctatctggt ttttgtcact acactcacta    11460
gtgattatac gattacagtc tttgttactg tcaaccttgc aaaagtttgc acttatgcca    11520
tctttgctta ctcaccacag cttacacttg tgtttccgga agtgaagatg atacttttat    11580
tatacacatg tttaggtttc atgtgtactt gctattttgg tgtcttctct cttttgaacc    11640
ttaagcttag agcacctatg ggtgtctatg actttaaggt ctcaacacaa gagttcagat    11700
tcatgactgc taacaatcta actgcaccta gaaattcttg ggaggctatg gctctgaact    11760
ttaagttaat aggtattggc ggtacacctt gtataaaggt tgctgctatg cagtctaaac    11820
ttacagatct taaatgcaca tctgtggttc tcctctctgt gctccaacag ttacacttag    11880
aggctaatag tagggcctgg gctttctgtg ttaaatgcca taatgatata ttggcagcaa    11940
cagaccccag tgaggctttc gagaaaattcg taagtctctt tgctacttta atgactttt    12000
ctggtaatgt agatcttgat gcgttagcta gtgatatttt tgacactcct agcgtacttc    12060
aagctactct ttctgagttt tcacacttag ctacctttgc tgagttggaa gctgcgcaga    12120
aagcctatca ggaagctatg gactctggtg acacctcacc acaagttctt aaggctttgc    12180
agaaggctgt taatatagct aaaaacgcct atgagaagga taaggcagtg gcccgtaagt    12240
tagaacgtat ggctgatcag gctatgactt ctatgtataa gcaagcacgt gctgaagaca    12300
agaaagcaaa aattgtcagt gctatgcaaa ctatgttgtt tggtatgatt aagaagctcg    12360
acaacgatgt tcttaatggt atcatttcta acgctaggaa tggttgtata cctcttagtg    12420
tcatcccact gtgtgcttca aataaacttc gcgttgtaat tcctgacttc accgtctgga    12480
atcaggtagt cacatatccc tcgcttaact acgctggggc tttgtgggac attacagtta    12540
taaacaatgt ggacaatgaa attgttaagt cttcagatgt tgtagacagc aatgaaaatt    12600
taacatggcc acttgtttta gaatgcacta gggcatccac ttctgccgtt aagttgcaaa    12660
ataatgagat caaaccttca ggtctaaaaa ccatggttgt gtctgcgggt caagagcaaa    12720
ctaactgtaa tactagttcc ttagcttatt acgaacctgt gcagggtcgt aaaatgctga    12780
tggctcttct ttctgataat gcctatctca aatgggcgcg tgttgaaggt aaggacggat    12840
ttgtcagtgt agagctacaa cctccttgca aattcttgat gcgggacca aaaggacctg    12900
aaatccgata tctctatttt gttaaaaatc ttaacaacct tcatcgcggg caagtgttag    12960
ggcacattgc tgcgactgtt agattgcaag ctggttctaa caccgagttt gcctctaatt    13020
cctcggtgtt gtcacttgtt aacttcaccg ttgatcctca aaaagcttat ctcgatttcg    13080
tcaatgcggg aggtgcccca ttgacaaatt gtgttaagat gcttactcct aaaactggta    13140
caggtatagc tatatctgtt aaaccagaga gtacagctga tcaagagact tatggtggag    13200
cttcagtgtg tctctattgc cgtgcgcata tagaacatcc tgatgtctct ggtgtttgta    13260
aatataaggg taagtttgtc caaatccctg ctcagtgtgt ccgtgaccct gtgggatttt    13320
gtttgtcaaa tacccctgt aatgtctgtc aatattggat tggatatggg tgcaattgtg    13380
actcgcttag gcaagcagca ctgccccaat ctaaagattc caattttta aacgagtccg    13440
gggttctatt gtaaatgccc gaatagaacc ctgttcaagt ggtttgtcca ctgatgtcgt    13500
cttaggggca tttgacatct gcaactataa ggctaaggtt gctggtattg aaaatactca    13560
caagactaat acttgtaggt ttgtagaatt agatgaccaa gggcatcatt tagactccta    13620
```

```
ttttgtcgtt aagaggcata ctatggagaa ttatgaacta gagaagcact gttacgactt    13680
gttacgtgac tgtgatgctg tagctcccca tgatttcttc atctttgatg tagacaaagt    13740
taaaacacct catattgtac gtcagcgttt aactgagtac actatgatgg atcttgtata    13800
tgccctgagg cactttgatc aaaatagcga agtgcttaag gctatcttag tgaagtatgg    13860
ttgctgtgat gttacctact ttgaaaataa actctggttt gattttgttg aaaatcccag    13920
tgttattggt gtttatcata aacttggaga acgtgtacgc caagctatct taaacactgt    13980
taaattttgt gaccacatgg tcaaggctgg tttagtcggt gtgctcacac tagacaacca    14040
ggaccttaat ggcaagtggt atgattttgg tgacttcgta atcactcaac ctggttcagg    14100
agtagctata gttgatagct actattctta tttgatgcct gtgctctcaa tgaccgattg    14160
tctggccgct gagacacata gggattgtga ttttaataaa ccactcattg agtggccact    14220
tactgagtat gattttactg attataaggt acaactcttt gagaagtact ttaaatattg    14280
ggatcagacg tatcacgcaa attgcgttaa ttgtactgat gaccgttgtg tgttacattg    14340
tgctaatttc aatgtattgt ttgctatgac catgcctaag acttgtttcg gacccatagt    14400
ccgaaagatc tttgttgatg gcgtgccatt tgtagtatct tgtggttatc actacaaaga    14460
attaggttta gtcatgaata tggatgttag tctccataga cataggctct ctcttaagga    14520
gttgatgatg tatgccgctg atccagccat gcacattgcc tcctctaacg cttttcttga    14580
tttgaggaca tcatgtttta gtgtcgctgc acttacaact ggtttgactt ttcaaactgt    14640
gcggcctggc aattttaacc aagacttcta tgatttcgtg gtatctaaag gtttctttaa    14700
ggagggctct tcagtgacgc tcaaacattt tttctttgct caagatggta atgctgctat    14760
tacagattat aattactatt cttataatct gcctactatg tgtgacatca aacaaatgtt    14820
gttctgcatg gaagttgtaa acaagtactt cgaaatctat gacggtggtt gtcttaatgc    14880
ttctgaagtg gttgttaata atttagacaa gagtgctggc catcctttta ataagtttgg    14940
caaagctcgt gtctattatg agagcatgtc ttaccaggag caagatgaac ttttgccat     15000
gacaaagcgt aacgtcattc ctaccatgac tcaaatgaat ctaaaatatg ctattagtgc    15060
taagaataga gctcgcactg ttgcaggcgt gtccatactt agcacaatga ctaatcgcca    15120
gtaccatcag aaaatgctta agtccatggc tgcaactcgt ggagcgactt cgtcattgg    15180
tactacaaag ttctacggtg gctgggattt catgcttaaa acattgtaca agatgttga     15240
taatccgcat cttatgggtt gggattaccc taagtgtgat agagctatgc ctaatatgtg    15300
tagaatcttc gcttcactca tattagctcg taaacatggc acttgttgta ctacaaggga    15360
cagattttat cgcttggcaa atgagtgtgc tcaggtgcta agcgaatatg ttctatgtgg    15420
tggtggttac tacgtcaaac ctggaggtac cagtagcgga gatgccacca ctgcatatgc    15480
caatagtgtc tttaacattt tgcaggcgac aactgctaat gtcagtgcac ttatgggtgc    15540
taatggcaac aagattgttg acaaagaagt aaagacatg cagtttgatt tgtatgtcaa     15600
tgtttacagg agcactagcc cagaccccaa atttgttgat aaatactatg ctttctaa     15660
taagcacttt tctatgatga tactgtctga tgacggtgtc gtttgctata atagtgatta    15720
tgcagctaag ggttacattg ctggaataca gaattttaag gaaacgctgt attatcagaa    15780
caatgtcttt atgtctgaag ctaaatgctg ggtggaaacc gatctgaaga agggccaca     15840
tgaattctgt tcacagcata cgctttatat taaggatggc gacgatggtt acttccttcc    15900
ttatccagac ccttcaagaa ttttgtctgc cggttgcttt gtagatgata tcgttaagac    15960
tgacggtaca ctcatggtag agcggtttgt gtctttggct atagatgctt accctctcac    16020
```

```
aaagcatgaa gatatagaat accagaatgt attctgggtc tacttacagt atatagaaaa   16080
actgtataaa gaccttacag gacacatgct tgacagttat tctgtcatgc tatgtggtga   16140
taattctgct aagttttggg aagaggcatt ctatagagat ctctatagtt cgcctaccac   16200
tttgcaggct gtcggttcat gcgttgtatg ccattcacag acttccctac gctgtgggac   16260
atgcatccgt agaccatttc tctgctgtaa atgctgctat gatcatgtta tagcaactcc   16320
acataagatg gttttgtctg tttctcctta cgtttgtaat gccctggtt gtggcgtttc     16380 agacgttact aagctatatt taggtggtat gagctacttt tgtgtagatc atagacctgt   16440
gtgtagtttt ccactttgcg ctaatggtct tgtattcggc ttatacaaga atatgtgcac   16500
aggtagtcct tctatagttg aatttaatag gttggctacc tgtgactgga ctgaaagtgg   16560
tgattacacc cttgccaata ctacaacaga accactcaaa cttttttgctg ctgagacttt   16620 acgtgccact gaagaggcgt ctaagcagtc ttatgctatt gccaccatca agaaattgt    16680 tggtgagcgc caactattac ttgtgtggga ggctggcaag tccaaaccac cactcaatcg   16740
taattatgtt tttactggtt atcatataac caaaaatagt aaagtgcagc tcggtgagta   16800
cattttcgag cgcattgatt atagtgatgc tgtatcctac aagtctagta caacgtataa   16860
actgactgta ggtgacatct tcgtacttac ctctcactct gtggctacct tgacggcgcc   16920
cacaattgtg aatcaagaga ggtatgttaa aattactggg ttgtacccaa ccattacggt   16980
acctgaagag ttcgcaagtc atgttgccaa cttccaaaaa tcaggttata gtaaatatgt   17040
cactgttcag ggaccacctg gcactggcaa aagtcatttt gctataggt tagcgattta     17100 ctaccctaca gcacgtgttg tttatacagc atgttcacac gcagctgttg atgctttgtg   17160
tgaaaaagct tttaaatatt tgaacattgc taaatgttcc cgtatcattc ctgcaaaggc   17220
acgtgttgag tgctatgaca ggtttaaagt taatgagaca aattctcaat atttgtttag   17280
tactattaat gctctaccag aaacttctgc cgatattctg gtggttgatg aggttagtat   17340
gtgcactaat tatgatcttt caattattaa tgcacgtatt aaagctaagc acattgtcta   17400
tgtaggagat ccagcacagt tgccagctcc taggactttg ttgactagag gcacattgga   17460
accagaaaat ttcaatagtg tcactagatt gatgtgtaac ttaggtcctg acatattttt   17520
aagtatgtgc tacaggtgtc ctaaggaaat agtaagcact gtgagcgctc ttgtctacaa   17580
taataaattg ttagccaaga aggagctttc aggccagtgc tttaaaatac tctataaggg   17640
caatgtgacg catgatgcta gctctgccat taatagacca caactcacat tgtgaagaa      17700 ttttattact gccaatccgg catggagtaa ggcagtcttt atttcgcctt acaattcaca   17760
gaatgctgtg tctcgttcaa tgctgggtct taccactcag actgttgatt cctcacaggg   17820
ttcagaatac cagtacgtta tcttctgtca aacagcagat acggcacatg ctaacaacat   17880
taacagattt aatgttgcaa tcactcgtgc ccaaaaaggt attctttgtg ttatgacatc   17940
tcaggcactc tttgagtcct tagagtttac tgaattgtct tttactaatt acaagctcca   18000
gtctcagatt gtaactggcc ttttttaaaga ttgctctaga gaaacttctg gcctctcacc   18060
tgcttatgca ccaacatatg ttagtgttga tgacaagtat aagacgagtg atgagctttg   18120
cgtgaatctt aatttacccg caaatgtccc atactctcgt gttatttcca ggatgggctt   18180
taaactcgat gcaacagttc ctggatatcc taagcttttc attactcgtg aagaggctgt   18240
aaggcaagtt cgaagctgga taggcttcga tgttgagggt gctcatgctt cccgtaatgc   18300
atgtggcacc aatgtgcctc tacaattagg attttcaact ggtgtgaact tgttgttca      18360
```

```
gccagttggt gttgtagaca ctgagtgggg taacatgtta acgggcattg ctgcacgtcc   18420
tccaccaggt gaacagttta agcacctcgt gcctcttatg cataaggggg ctgcgtggcc   18480
tattgttaga cgacgtatag tgcaaatgtt gtcagacact ttagacaaat tgtctgatta   18540
ctgtacgttt gtttgttggg ctcatggctt tgaattaacg tctgcatcat acttttgcaa   18600
gataggtaag gaacagaagt gttgcatgtg caatagacgc gctgcagcgt actcttcacc   18660
tctgcaatct tatgcctgct ggactcattc ctgcggttat gattatgtct acaacccttt   18720 cttttgtcgat gttcaacagt ggggttatgt aggcaatctt gctactaatc acgatcgtta   18780
ttgctctgtc catcaaggag ctcatgtggc ttctaatgat gcaataatga ctcgttgttt   18840
agctattcat tcttgtttta tagaacgtgt ggattgggat atagagtatc cttatatctc   18900
acatgaaaag aaattgaatt cctgttgtag aatcgttgag cgcaacgtcg tacgtgctgc   18960
tcttcttgcc ggttcatttg acaaagtcta tgatattggc aatcctaaag gaattcctat   19020
tgttgatgac cctgtggttg attggcatta ttttgatgca cagcccttga ccaggaaggt   19080
acaacagctt ttctatacag aggacatggc ctcaagattt gctgatgggc tctgcttatt   19140
ttggaactgt aatgtaccaa aatatcctaa taatgcaatt gtatgcaggt ttgacacacg   19200
tgtgcattct gagttcaatt tgccaggttg tgatggcggt agtttgtatg ttaacaagca   19260
cgcttttcat acaccagcat atgatgtgag tgcattccgt gatctgaaac ctttaccatt   19320
cttttattat tctactacac catgtgaagt gcatggtaat ggtagtatga tagaggatat   19380
tgattatgta cccctaaaat ctgcagtctg tattacagct tgtaatttag ggggcgctgt   19440
ttgtaggaag catgctacag agtacagaga gtatatggaa gcataatcc ttgtctctgc   19500 atcaggtttc cgcctttggt gttataagac ctttgatatt tataatctct ggtctacttt   19560
tacaaaagtt caaggtttgg aaaacattgc ttttaatgtt gttaaacaag gccattttat   19620
tggtgttgag ggtgaactac ctgtagctgt agtcaatgat aagatcttca ccaagagtgg   19680
cgttaatgac atttgtatgt ttgagaataa aaccactttg cctactaata tagcttttga   19740
actctatgct aagcgtgctg tacgctcgca tcccgatttc aaaattgctac acaatttaca   19800 agcagacatt tgctacaagt tcgtcctttg ggattatgaa cgtagcaata tttatggtac   19860
tgctactatt ggtgtatgta agtacactga tattgatgtt aattcagctt tgaatatatg   19920
ttttgacata cgcgataatt gttcattgga gaagttcatg tctactccca atgccatctt   19980
tatttctgat agaaaaatca agaaataccc ttgtatggta ggtcctgatt atgcttactt   20040
caatggtgct atcatccgtg atagtgatgt tgttaaacaa ccagtgaagt tctacttgta   20100
taagaaagtc aataatgagt ttattgatcc tactgagtgt atttacactc agagtcgctc   20160
ttgtagtgac ttcctacccc tttctgacat ggagaaagac tttctatctt ttgatagtga   20220
tgttttcatt aagaagtatg gcttggaaaa ctatgctttt gagcacgtag tctatggaga   20280
cttctctcat actacgttag gcggtcttca cttgcttatt ggtttataca agaagcaaca   20340
ggaaggtcat attattatgg aagaaatgct aaaaggtagc tcaactattc ataactattt   20400
tattactgag actaacacag cggcttttaa ggcggtgtgt tctgttatag atttaaagct   20460
tgacgacttt gttatgattt taaagagtca agacctggc gtagtatcca aggttgtcaa   20520
ggttcctatt gacttaacaa tgattgagtt tatgttatgg tgtaaggatg acaggttca   20580 aaccttctac cctcgactcc aggcttctgc agattggaaa cctggtcatg caatgccatc   20640
cctctttaaa gttcaaaatg taaaccttga acgttgtgag cttgctaatt acaagcaatc   20700
tattcctatg cctcgcggtg tgcacatgaa catcgctaaa tatatgcaat tgtgccagta   20760
```

```
tttaaatact tgcacattag ccgtgcctgc caatatgcgt gttatacatt ttggcgctgg   20820
ttctgataaa ggtatcgctc ctggtacctc agttttacga cagtggcttc ctacagatgc   20880
cattattata gataatgatt taaatgagtt cgtgtcagat gctgacataa ctttatttgg   20940
agattgtgta actgtacgtg tcggccaaca agtggatctt gttatttccg acatgtatga   21000
tcctactact aagaatgtaa caggtagtaa tgagtcaaag gctttattct ttacttacct   21060
gtgtaacctc attaataata atcttgctct tggtgggtct gttgctatta aaataacaga   21120
acactcttgg agcgttgaac tttatgaact tatgggaaaa tttgcttggt ggactgtttt   21180
ctgcaccaat gcaaatgcat cctcatctga aggattcctc ttaggtatta attacttggg   21240
tactattaaa gaaaatatag atggtggtgc tatgcacgcc aactatatat tttggagaaa   21300
ttccactcct atgaatctga gtacttactc acttttttgat ttatccaagt ttcaattaaa   21360
attaaaagga acaccagttc ttcaattaaa ggagagtcaa attaacgaac tcgtaatatc   21420
tctcctgtcg cagggtaagt tactatccg tgacaatgat acactcagtg tttctactga   21480
tgttcttgtt aacacctaca gaaagttacg ttgatgtagg gccagattct gttaagtctg   21540
cttgtattga ggttgatata caacagactt tctttgataa aacttggcct aggccaattg   21600
atgtttctaa ggctgacggt attatatacc ctcaaggccg tacatattct aacataacta   21660
tcacttatca aggtctttt ccctatcagg gagaccatgg tgatatgtat gtttactctg   21720
caggacatgc tacaggcaca actccacaaa agttgtttgt agctaactat tctcaggacg   21780
tcaaacagtt tgctaatggg tttgtcgtcc gtataggagc agctgccaat tccactggca   21840
ctgttattat tagcccatct accagcgcta ctatacgaaa aatttacccct gcttttatgc   21900 tgggttcttc agttggtaat ttctcagatg gtaaaatggg ccgcttcttc aatcatactc   21960
tagttctttt gcccgatgga tgtggcactt tacttagagc ttttttattgt attctagagc   22020 ctcgctctgg aaatcattgt cctgctggca attcctatac ttcttttgcc acttatcaca   22080
ctcctgcaac agattgttct gatggcaatt acaatcgtaa tgccagtctg aactcttta   22140 aggagtattt taatttacgt aactgcaccct ttatgtacac ttataacatt accgaagatg   22200
agattttaga gtggtttggc attacacaaa ctgctcaagg tgttcacctc ttctcatctc   22260
ggtatgttga tttgtacggc ggcaatatgt ttcaatttgc caccttgcct gtttatgata   22320
ctattaagta ttattctatc attcctcaca gtattcgttc tatccaaagt gatagaaaag   22380
cttgggctgc cttctacgta tataaacttc aaccgttaac tttcctgttg gattttctg   22440 ttgatggtta tatacgcaga gctatagact gtggttttaa tgatttgtca caactccact   22500
gctcatatga atccttcgat gttgaatctg gagtttattc agtttcgtct ttcgaagcaa   22560
aaccttctgg ctcagttgtg gaacaggctg aaggtgttga atgtgatttt tcacctcttc   22620
tgtctggcac acctcctcag gtttataatt tcaagcgttt ggttttacc aattgcaatt   22680 ataatcttac caaattgctt tcactttttt ctgtgaatga ttttacttgt agtcaaatat   22740
ctccagcagc aattgctagc aactgttatt cttcactgat tttggattac ttttcatacc   22800
cacttagtat gaaatccgat ctcagtgtta gttctgctgg tccaatatcc cagtttaatt   22860
ataaacagtc ctttttctaat cccacatgtt tgatttttagc gactgttcct cataacctta   22920
ctactattac taagcctctt aagtacagct atattaacaa gtgctctcgt cttctttctg   22980
atgatcgtac tgaagtacct cagttagtga acgctaatca atactcaccc tgtgtatcca   23040
ttgtcccatc cactgtgtgg gaagacggtg attattatag gaaacaacta tctccacttg   23100
```

```
aaggtggtgg ctggcttgtt gctagtggct caactgttgc catgactgag caattacaga    23160
tgggctttgg tattacagtt caatatggta cagacaccaa tagtgtttgc cccaagcttg    23220
aatttgctaa tgacacaaaa attgcctctc aattaggcaa ttgcgtggaa tattccctct    23280
atggtgtttc gggccgtggt gttttttcaga attgcacagc tgtaggtgtt cgacagcagc    23340
gctttgttta tgatgcgtac cagaatttag ttggctatta ttctgatgat ggcaactact    23400
actgtttgcg tgcttgtgtt agtgttcctg tttctgtcat ctatgataaa gaaactaaaa    23460
cccacgctac tctatttggt agtgttgcat gtgaacacat ttcttctacc atgtctcaat    23520
actcccgttc tacgcgatca atgcttaaac ggcgagattc tacatatggc ccccttcaga    23580
cacctgttgg ttgtgtccta ggacttgtta attcctcttt gttcgtagag gactgcaagt    23640
tgcctcttgg tcaatctctc tgtgctcttc ctgacacacc tagtactctc acacctcgca    23700
gtgtgcgctc tgttccaggt gaaatgcgct tggcatccat tgcttttaat catcctattc    23760
aggttgatca acttaatagt agttatttta aattaagtat acccactaat ttttcctttg    23820
gtgtgactca ggagtacatt cagacaacca ttcagaaagt tactgttgat tgtaaacagt    23880
acgtttgcaa tggtttccag aagtgtgagc aattactgcg cgagtatggc cagttttgtt    23940
ccaaaataaa ccaggctctc catggtgcca atttacgcca ggatgattct gtacgtaatt    24000
tgtttgcgag cgtgaaaagc tctcaatcat ctcctatcat accaggtttt ggaggtgact    24060 taatttgac acttctagaa cctgtttcta tatctactgg cagtcgtagt gcacgtagtg    24120
ctattgagga tttgctattt gacaaagtca ctatagctga tcctggttat atgcaaggtt    24180
acgatgattg catgcagcaa ggtccagcat cagctcgtga tcttatttgt gctcaatatg    24240
tggctggtta caaagtatta cctcctctta tggatgttaa tatggaagcc gcgtatactt    24300
catctttgct tggcagcata gcaggtgttg gctggactgc tggcttatcc tcctttgctg    24360
ctattccatt tgcacagagt atcttttata ggttaaacgg tgttggcatt actcaacagg    24420
ttctttcaga gaaccaaaag cttattgcca ataagtttaa tcaggctctg ggagctatgc    24480
aaacaggctt cactacaact aatgaagctt ttcagaaggt tcaggatgct gtgaacaaca    24540
atgcacaggc tctatccaaa ttagctagcg agctatctaa tacttttggt gctatttccg    24600
cctctattgg agacatcata caacgtcttg atgttctcga acaggacgcc caaatagaca    24660
gacttattaa tggccgtttg acaacactaa atgctttttgt tgcacagcag cttgttcgtt    24720
ccgaatcagc tgctctttcc gctcaattgg ctaaagataa agtcaatgag tgtgtcaagg    24780
cacaatccaa cgcgttctga ttttgcggtc aaggcacaca tatagtgtcc tttgttgtaa    24840
atgcccctaa tggcctttac ttcatgcatg ttggttatta ccctagcaac cacattgagg    24900
ttgtttctgc ttatggtctt tgcgatgcag ctaaccctac taattgtata gcccctgtta    24960
atggctactt tattaaaact aataacacta ggattgttga tgagtggtca tatactggct    25020
cgtccttcta tgcacctgag cccattacct cccttaatac taagtatgtt gcaccacagg    25080
tgacatacca aaacatttct actaacctcc ctcctcctct tctcggcaat tccaccggga    25140
ttgacttcca agatgagttg gatgagtttt tcaaaaatgt tagcaccagt atacctaatt    25200
ttggttccct aacacagatt aatactacat tactcgatct tacctacgag atgttgtctc    25260
ttcaacaagt tgttaaagcc cttaatgagt cttcatagag ccttaaagag cttggcaatt    25320
atacttatta caacaaatgg ccgtggtaca tttggcttgg tttcattgct ggcttgttg    25380 ccttagctct atgcgtcttc ttcatactgt gctgcactgg ttgtggcaca aactgtatgg    25440
gaaaacttaa gtgtaatcgt tgttgtgata gatacgagga atacgacctc gagccgcata    25500
```

```
aggttcatgt tcactaatta acgaactatt aatgagagtt caaagaccac ccactctctt   25560
gttagtgttt tcactctctc ttttggtcac tgcatcctca aaacctctct atgtacctga   25620
gcattgtcag aattattctg gttgcatgct tagggcttgt attaaaactg cccaagctga   25680
tacagctggt ctttatacaa attttcgaat tgacgtccca tctgcagaat caactggtac   25740
tcaatcagtt tctgtcgatc ttgagtcaac ttcaactcat gatggtccta ccgaacatgt   25800
tactagtgtg aatcttttg acgttggtta ctcagttaat taacgaactc tatggattac    25860
gtgtctctgc ttaatcaaat ttggcagaag taccttaact caccgtatac tacttgtttg   25920
tacatcccta aacccacagc taagtataca cctttagttg gcacttcatt gcaccctgtg   25980
ctgtggaact gtcagctatc ctttgctggt tatactgaat ctgctgttaa ttctacaaaa   26040
gctttggcca acaggacgc agctcagcga atcgcttggt tgctacataa ggatggagga    26100
atccctgatg gatgttccct ctacctccgg cactcaagtt tattcgcgca aagcgaggaa   26160
gaggagccat tctccaacta agaaactgcg ctacgttaag cgtagatttt ctcttctgcg   26220
ccatgaagac cttagtgtta ttgtccaacc aacacactat gtcagggtta cattttcaga   26280
ccccaacatg tggtatctac gttcgggtca tcatttacac tcagttcaca attggcttaa   26340
accttatggc ggccaacctg tttctgagta ccatattact ctagctttgc taaatctcac   26400
tgatgaagat ttagctagag attttttcacc cattgcgctc tttttgcgca atgtcagatt   26460
tgagctacat gagttcgcct tgctgcgcaa aactcttgtt cttaatgcat cagagatcta   26520
ctgtgctaac atacatagat ttaagcctgt gtatagagtt aacacggcaa tccctactat   26580
taaggattgg cttctcgttc agggattttc cctttaccat agtggcctcc ctttacatat   26640
gtcaatctct aaattgcatg cactggatga tgttactcgc aattacatca ttacaatgcc   26700
atgctttaga acttaccctc aacaaatgtt tgttactcct ttggccgtag atgttgtctc   26760
catacggtct tccaatcagg gtaataaaca aattgttcat tcttatccca ttttacatca   26820
tccaggattt taacgaacta tggctttctc ggcgtctta tttaaacccg tccagctagt    26880
cccagtttct cctgcatttc atcgcattga gtctactgac tctattgttt tcacatacat   26940
tcctgctagc ggctatgtag ctgctttagc tgtcaatgtg tgtctcattc ccctattatt   27000
actgctacgt caagatactt gtcgtcgcag cattatcaga actatggttc tctatttcct   27060
tgttctgtat aactttttat tagccattgt actagtcaat ggtgtacatt atccaactgg   27120
aagttgcctg atagccttct tagttatcct cataatactt tggtttgtag atagaattcg   27180
tttctgtctc atgctgaatt cctacattcc actgttgac atgcgttccc actttattcg   27240
tgttagtaca gtttcttctc atggtatggt ccctgtaata cacaccaaac cattatttat   27300
tagaaacttc gatcagcgtt gcagctgttc tcgttgtttt tatttgcact cttccactta   27360
tatagagtgc acttatatta gccgttttag taagattagc ctagtttctg taactgactt   27420
ctccttaaac ggcaatgttt ccactgtttt cgtgcctgca acgcgcgatt cagttcctct   27480
tcacataatc gccccgagct cgcttatcgt ttaagcagct ctgcgctact atgggtcccg   27540
tgtagaggct aatccattag tctctctttg gacatatgga aaacgaacta tgttacccctt  27600 tgtccaagaa cgaatagggt tgttcatagt aaacttttc attttaccg tagtatgtgc     27660 tataacactc ttggtgtgta tggctttcct tacggctact agattatgtg tgcaatgtat   27720
gacaggcttc aatccctgt tagttcagcc cgcattatac ttgtataata ctggacgttc    27780
agtctatgta aaattccagg atagtaaacc ccctctacca cctgacgagt gggtttaacg   27840
```

```
aactccttca taatgtctaa tatgacgcaa ctcactgagg cgcagattat tgccattatt   27900
aaagactgga actttgcatg gtccctgatc tttctcttaa ttactatcgt actacagtat   27960
ggatacccat cccgtagtat gactgtctat gtctttaaaa tgtttgtttt atggctccta   28020
tggccatctt ccatggcgct atcaatattt agcgccgttt atccaattga tctagcttcc   28080
cagataatct ctggcattgt agcagctgtt tcagctatga tgtggatttc ctactttgtg   28140
cagagtatcc ggctgtttat gagaactgga tcatggtggt cattcaatcc tgagactaat   28200
tgccttttga acgttccatt tggtggtaca actgtcgtac gtccactcgt agaggactct   28260
accagtgtaa ctgctgttgt aaccaatggc cacctcaaaa tggctggcat gcatttcggt   28320
gcttgtgact acgacagact tcctaatgaa gtcaccgtgg ccaaacccaa tgtgctgatt   28380
gctttaaaaa tggtgaagcg gcaaagctac ggaactaatt ccggcgttgc catttaccat   28440
agatataagg caggtaatta caggagtccg cctattacgg cggatattga acttgcattg   28500
cttcgagctt aggctctttta gtaagagtat cttaattgat tttaacgaat ctcaatttca   28560
ttgttatggc atcccctgct gcacctcgtg ctgtttcctt tgccgataac aatgatataa   28620
caaatacaaa cctatctcga ggtagaggac gtaatccaaa accacgagct gcaccaaata   28680
acactgtctc ttggtacact gggcttaccc aacacgggaa agtccctctt accttttccac   28740
ctgggcaggg tgtacctctt aatgccaatt ctaccccctgc gcaaaatgct gggtattggc   28800
ggagacagga cagaaaaatt aataccggga atggaattaa gcaactggct cccaggtggt   28860
acttctacta cactggaact ggaccccgaag cagcactccc attccgggct gttaaggatg   28920
gcatcgtttg gtccatgaa gatggcgcca ctgatgctcc ttcaacttttt gggacgcgga   28980
accctaacaa tgattcagct attgttacac aattcgcgcc cggtactaag cttcctaaaa   29040
acttccacat tgaggggact ggaggcaata gtcaatcatc ttcaagagcc tctagcttaa   29100
gcagaaactc ttccagatct agttcacaag gttcaagatc aggaaactct acccgcggca   29160
cttctccagg tccatctgga atcggagcag taggaggtga tctactttac cttgatcttc   29220
tgaacagact acaagcccctt gagtctggca agtaaagca atcgcagcca aaagtaatca   29280
ctaagaaaga tgctgctgct gctaaaaata agatgcgcca caagcgcact tccaccaaaa   29340
gtttcaacat ggtgcaagct tttggtcttc gcggaccagg agacctccag ggaaactttg   29400
gtgatcttca attgaataaa ctcggcactg aggacccacg ttggcccaa attgctgagc   29460
ttgctcctac agccagtgct tttatgggta tgtcgcaatt taaacttacc catcagaaca   29520
atgatgatca tggcaaccct gtgtacttcc ttcggtacag tggagccatt aaacttgacc   29580
caaagaatcc caactacaat aagtggttgg agcttcttga caaaatatt gatgcctaca   29640
aaaccttccc taagaaggaa aagaaacaaa aggcaccaaa agaagaatca acagaccaaa   29700
tgtctgaacc tccaaaggag cagcgtgtgc aaggtagcat cactcagcgc actcgcaccc   29760
gtccaagtgt tcagcctggt ccaatgattg atgttaacac tgattagtgt cactcaaagt   29820
aacaagatcg cggcaatcgt ttgtgtttgg caacccccatc tcaccatcgc ttgtccactc   29880
ttgcacagaa tggaatcatg ttgtaattac agtgcaataa ggtaattata acccatttaa   29940
ttgatagcta tgctttatta aagtgtgtag ctgtagagag aatgttaaag actgtcacct   30000
ctgcttgatt gcaagtgaac agtgcccccc gggaagagct ctacagtgtg aaatgtaaat   30060
aaaaaatagc tattattcaa ttagattagg ctaattagat gatttgcaaa aaaaaaaaa    30119
```

<210> SEQ ID NO 12
<211> LENGTH: 29903

<212> TYPE: DNA
<213> ORGANISM: SARS-CoV-2

<400> SEQUENCE: 12
attaaaggtt tataccttcc caggtaacaa accaaccaac tttcgatctc ttgtagatct 60
gttctctaaa cgaactttaa aatctgtgtg gctgtcactc ggctgcatgc ttagtgcact 120
cacgcagtat aattaataac taattactgt cgttgacagg acacgagtaa ctcgtctatc 180
ttctgcaggc tgcttacggt ttcgtccgtg ttgcagccga tcatcagcac atctaggttt 240
cgtccgggtg tgaccgaaag gtaagatgga gagccttgtc cctggtttca acgagaaaac 300
acacgtccaa ctcagtttgc ctgttttaca ggttcgcgac gtgctcgtac gtggctttgg 360
agactccgtg gaggaggtct tatcagaggc acgtcaacat cttaaagatg gcacttgtgg 420
cttagtagaa gttgaaaaag gcgttttgcc tcaacttgaa cagccctatg tgttcatcaa 480
acgttcggat gctcgaactg cacctcatgg tcatgttatg gttgagctgg tagcagaact 540
cgaaggcatt cagtacggtc gtagtggtga gacacttggt gtccttgtcc ctcatgtggg 600
cgaaatacca gtggcttacc gcaaggttct tcttcgtaag aacggtaata aaggagctgg 660
tggccatagt tacggcgccg atctaaagtc atttgactta ggcgacgagc ttggcactga 720
tccttatgaa gattttcaag aaaactggaa cactaaacat agcagtggtg ttacccgtga 780
actcatgcgt gagcttaacg gaggggcata cactcgctat gtcgataaca acttctgtgg 840
ccctgatggc taccctcttg agtgcattaa agaccttcta gcacgtgctg gtaaagcttc 900
atgcactttg tccgaacaac tggactttat tgacactaag aggggtgtat actgctgccg 960
tgaacatgag catgaaattg cttggtacac ggaacgttct gaaaagagct atgaattgca 1020
gacacctttt gaaattaaat tggcaaagaa atttgacacc ttcaatgggg aatgtccaaa 1080
ttttgtattt cccttaaatt ccataatcaa gactattcaa ccaagggttg aaaagaaaaa 1140
gcttgatggc tttatgggta gaattcgatc tgtctatcca gttgcgtcac caaatgaatg 1200
caaccaaatg tgcctttcaa ctctcatgaa gtgtgatcat tgtggtgaaa cttcatggca 1260
gacgggcgat tttgttaaag ccacttgcga attttgtggc actgagaatt tgactaaaga 1320
aggtgccact acttgtggtt acttacccca aaatgctgtt gttaaaattt attgtccagc 1380
atgtcacaat tcagaagtag gacctgagca tagtcttgcc gaataccata atgaatctgg 1440
cttgaaaacc attcttcgta agggtggtcg cactattgcc tttggaggct gtgtgttctc 1500
ttatgttggt tgccataaca agtgtgccta ttgggttcca cgtgctagcg ctaacatagg 1560
ttgtaaccat acaggtgttg ttggagaagg ttccgaaggt cttaatgaca accttcttga 1620
aatactccaa aaagagaaag tcaacatcaa tattgttggt gactttaaac ttaatgaaga 1680
gatcgccatt attttggcat ctttttctgc ttccacaagt gcttttgtgg aaactgtgaa 1740
aggtttggat tataaagcat tcaaacaaat tgttgaatcc tgtggtaatt ttaaagttac 1800
aaaaggaaaa gctaaaaaag gtgcctggaa tattggtgaa cagaaatcaa tactgagtcc 1860
tctttatgca tttgcatcag aggctgctcg tgttgtacga tcaattttct cccgcactct 1920
tgaaactgct caaaattctg tgcgtgtttt acagaaggcc gctataacaa tactagatgg 1980
aatttcacag tattcactga gactcattga tgctatgatg ttcacatctg atttggctac 2040
taacaatcta gttgtaatgg cctacattac aggtggtgtt gttcagttga cttcgcagtg 2100
gctaactaac atctttggca ctgtttatga aaaactcaaa cccgtccttg attggcttga 2160
agagaagttt aaggaaggtg tagagtttct tagagacggt tgggaaattg ttaaatttat 2220

```
ctcaacctgt gcttgtgaaa ttgtcggtgg acaaattgtc acctgtgcaa aggaaattaa    2280
ggagagtgtt cagacattct ttaagcttgt aaataaattt ttggctttgt gtgctgactc    2340
tatcattatt ggtggagcta aacttaaagc cttgaattta ggtgaaacat tgtcacgca     2400 ctcaaaggga ttgtacagaa agtgtgttaa atccagagaa gaaactggcc tactcatgcc    2460
tctaaaagcc ccaaaagaaa ttatcttctt agagggagaa acacttccca cagaagtgtt    2520
aacagaggaa gttgtcttga aaactggtga tttacaacca ttagaacaac ctactagtga    2580
agctgttgaa gctccattgg ttggtacacc agtttgtatt aacgggctta tgttgctcga    2640
aatcaaagac acagaaaagt actgtgccct tgcacctaat atgatggtaa caaacaatac    2700
cttcacactc aaaggcggtg caccaacaaa ggttactttt ggtgatgaca ctgtgataga    2760
agtgcaaggt tacaagagtg tgaatatcac ttttgaactt gatgaaagga ttgataaagt    2820
acttaatgag aagtgctctg cctatacagt tgaactcggt acagaagtaa atgagttcgc    2880
ctgtgttgtg gcagatgctg tcataaaaac tttgcaacca gtatctgaat tacttacacc    2940
actgggcatt gatttagatg agtggagtat ggctacatac tacttatttg atgagtctgg    3000
tgagtttaaa ttggcttcac atatgtattg ttctttctac cctccagatg aggatgaaga    3060
agaaggtgat tgtgaagaag aagagtttga gccatcaact caatatgagt atggtactga    3120
agatgattac caaggtaaac ctttggaatt tggtgccact tctgctgctc ttcaacctga    3180
agaagagcaa gaagaagatt ggttagatga tgatagtcaa caaactgttg gtcaacaaga    3240
cggcagtgag gacaatcaga caactactat tcaaacaatt gttgaggttc aacctcaatt    3300
agagatggaa cttacaccag ttgttcagac tattgaagtg aatagttta gtggttattt     3360 aaaacttact gacaatgtat acattaaaaa tgcagacatt gtggaagaag ctaaaaaggt    3420
aaaaccaaca gtggttgtta atgcagccaa tgtttacctt aaacatggag gaggtgttgc    3480
aggagcctta ataaggctac taacaatgc catgcaagtt gaatctgatg attacatagc      3540
tactaatgga ccacttaaag tgggtggtag ttgtgtttta agcggacaca atcttgctaa    3600
acactgtctt catgttgtcg gcccaaatgt taacaaaggt gaagacattc aacttcttaa    3660
gagtgcttat gaaaatttta atcagcacga agttctactt gcaccattat tatcagctgg    3720 tattttttggt gctgacccta cattctcttt aagagtttgt gtagatactg ttcgcacaaa    3780
tgtctactta gctgtctttg ataaaaatct ctatgacaaa cttgtttcaa gcttttgga     3840 aatgaagagt gaaaagcaag ttgaacaaaa gatcgctgag attcctaaag aggaagttaa    3900
gccatttata actgaaagta aaccttcagt tgaacagaga aaacaagatg ataagaaaat    3960
caaagcttgt gttgaagaag ttacaacaac tctggaagaa actaagttcc tcacagaaaa    4020
cttgttactt tatattgaca ttaatggcaa tcttcatcca gattctgcca ctcttgttag    4080
tgacattgac atcactttct aaagaaaga tgctccatat atagtgggtg atgttgttca      4140
agagggtgtt ttaactgctg tggttatacc tactaaaaag gctggtggca ctactgaaat    4200
gctagcgaaa gctttgagaa aagtgccaac agacaattat ataaccactt acccgggtca    4260
gggtttaaat ggttacactg tagaggaggc aaagacagtg cttaaaaagt gtaaaagtgc    4320
cttttacatt ctaccatcta ttatctctaa tgagaagcaa gaaattcttg gaactgtttc    4380
ttggaatttg cgagaaatgc ttgcacatgc agaagaaaca cgcaaattaa tgcctgtctg    4440
tgtggaaact aaagccatag tttcaactat acagcgtaaa tataagggta ttaaaataca    4500
agagggtgtg gttgattatg gtgctagatt ttacttttac accagtaaaa caactgtagc    4560
gtcacttatc aacacactta acgatctaaa tgaaactctt gttacaatgc cacttggcta    4620
```

```
tgtaacacat ggcttaaatt tggaagaagc tgctcggtat atgagatctc tcaaagtgcc   4680
agctacagtt tctgtttctt cacctgatgc tgttacagcg tataatggtt atcttacttc   4740
ttcttctaaa acacctgaag aacattttat tgaaaccatc tcacttgctg gttcctataa   4800
agattggtcc tattctggac aatctacaca actaggtata gaatttctta agagaggtga   4860
taaaagtgta tattcacacta gtaatcctac cacattccac ctagatggtg aagttatcac   4920
ctttgacaat cttaagacac ttctttcttt gagagaagtg aggactatta aggtgtttac   4980
aacagtagac aacattaacc tccacacgca agttgtggac atgtcaatga catatggaca   5040
acagtttggt ccaacttatt tggatggagc tgatgttact aaaataaaac ctcataattc   5100
acatgaaggt aaaacatttt atgttttacc taatgatgac actctacgtg ttgaggcttt   5160
tgagtactac cacacaactg atcctagttt tctgggtagg tacatgtcag cattaaatca   5220
cactaaaaag tggaaatacc cacaagttaa tggtttaact tctattaaat gggcagataa   5280
caactgttat cttgccactg cattgttaac actccaacaa atagagttga agtttaatcc   5340
acctgctcta caagatgctt attacagagc aagggctggt gaagctgcta acttttgtgc   5400
acttatctta gcctactgta ataagacagt aggtgagtta ggtgatgtta gagaaacaat   5460
gagttacttg tttcaacatg ccaatttaga ttcttgcaaa agagtcttga acgtggtgtg   5520
taaaacttgt ggacaacagc agacaaccct taagggtgta gaagctgtta tgtacatggg   5580
cacactttct tatgaacaat ttaagaaagg tgttcagata ccttgtacgt gtggtaaaca   5640
agctacaaaa tatctagtac aacaggagtc acctttgtt atgatgtcag caccacctgc   5700
tcagtatgaa cttaagcatg gtacatttac ttgtgctagt gagtacactg gtaattacca   5760
gtgtggtcac tataaacata taacttctaa agaaactttg tattgcatag acggtgcttt   5820
acttacaaag tcctcagaat acaaaggtcc tattacggat gttttctaca agaaaacag   5880 ttacacaaca accataaaac cagttactta taaattggat ggtgttgttt gtacagaaat   5940
tgaccctaag ttggacaatt attataagaa agacaattct tatttcacag agcaaccaat   6000
tgatcttgta ccaaaccaac catatccaaa cgcaagcttc gataatttta gtttgtatg   6060 tgataatatc aaatttgctg atgatttaaa ccagttaact ggttataaga aacctgcttc   6120
aagagagctt aaagttacat ttttccctga cttaaatggt gatgtggtgg ctattgatta   6180
taaacactac acaccctctt ttaagaaagg agctaaattg ttacataaac ctattgtttg   6240
gcatgttaac aatgcaacta ataaagccac gtataaacca aatacctggt gtatacgttg   6300
tctttggagc acaaaaccag ttgaaacatc aaattcgttt gatgtactga agtcagagga   6360
cgcgcaggga atggataatc ttgcctgcga agatctaaaa ccagtctctg aagaagtagt   6420
ggaaaatcct accatacaga aagacgttct tgagtgtaat gtgaaaacta ccgaagttgt   6480
aggagacatt atacttaaac cagcaaataa tagtttaaaa attacagaag aggttggcca   6540
cacagatcta atggctgctt atgtagacaa ttcagtctt actattaaga aacctaatga   6600
attatctaga gtattaggtt tgaaaacct tgctactcat ggtttagctg ctgttaatag   6660
tgtcccttgg gatactatag ctaattatgc taagccttt cttaacaaag ttgttagtac   6720
aactactaac atagttacac ggtgtttaaa ccgtgtttgt actaattata tgccttattt   6780
ctttactttt ttgctacaat tgtgtacttt tactagaagt acaaattcta gaattaaagc   6840
atctatgccg actactatag caaagaatac tgttaagagt gtcggtaaat tttgtctaga   6900
ggcttcattt aattattttg agtcacctaa ttttttctaaa ctgataaata ttataatttg   6960
```

```
gttttttacta ttaagtgttt gcctaggttc tttaatctac tcaaccgctg ctttaggtgt      7020
tttaatgtct aatttaggca tgccttctta ctgtactggt tacagagaag gctatttgaa      7080
ctctactaat gtcactattg caacctactg tactggttct ataccttgta gtgtttgtct      7140
tagtggttta gattctttag acacctatcc ttctttagaa actatacaaa ttaccatttc      7200
atcttttaaa tgggatttaa ctgcttttgg cttagttgca gagtggtttt tggcatatat      7260
tcttttcact aggttttttct atgtacttgg attggctgca atcatgcaat tgttttcag       7320 ctattttgca gtacatttta ttagtaattc ttggcttatg tggttaataa ttaatcttgt       7380
acaaatggcc ccgatttcag ctatggttag aatgtacatc ttctttgcat cattttatta      7440
tgtatggaaa agttatgtgc atgttgtaga cggttgtaat tcatcaactt gtatgatgtg      7500
ttacaaacgt aatagagcaa caagagtcga atgtacaact attgttaatg gtgttagaag      7560
gtccttttat gtctatgcta atggaggtaa aggcttttgc aaactacaca attggaattg      7620
tgttaattgt gatacattct gtgctggtag tacatttatt agtgatgaag ttgcgagaga      7680
cttgtcacta cagtttaaaa gaccaataaa tcctactgac cagtcttctt acatcgttga      7740
tagtgttaca gtgaagaatg gttccatcca tcttttacttt gataaagctg gtcaaaagac     7800
ttatgaaaga cattctctct ctcattttgt aacttagac aacctgagag ctaataacac        7860
taaaggttca ttgcctatta atgttatagt ttttgatggt aaatcaaaat gtgaagaatc      7920
atctgcaaaa tcagcgtctg tttactacag tcagcttatg tgtcaaccta tactgttact      7980
agatcaggca ttagtgtctg atgttggtga tagtgcggaa gttgcagtta aatgtttga        8040 tgcttacgtt aatacgtttt catcaacttt taacgtacca atggaaaaac tcaaaacact      8100
agttgcaact gcagaagctg aacttgcaaa gaatgtgtcc ttagacaatg tcttatctac      8160
ttttatttca gcagctcggc aagggtttgt tgattcagat gtagaaacta agatgttgt        8220 tgaatgtctt aaattgtcac atcaatctga catagaagtt actggcgata gttgtaataa      8280
ctatatgctc acctataaca aagttgaaaa catgacaccc cgtgaccttg gtgcttgtat      8340
tgactgtagt gcgcgtcata ttaatgcgca ggtagcaaaa agtcacaaca ttgcttttgat     8400 atggaacgtt aaagatttca tgtcattgtc tgaacaacta cgaaaacaaa tacgtagtgc      8460
tgctaaaaag aataacttac cttttaagtt gacatgtgca actactagac aagttgttaa      8520
tgttgtaaca acaaagatag cacttaaggg tggtaaaatt gttaataatt ggttgaagca      8580
gttaattaaa gttacacttg tgttccttttt tgttgctgct attttctatt taataacacc     8640
tgttcatgtc atgtctaaac atactgactt ttcaagtgaa atcataggat acaaggctat     8700
tgatggtggt gtcactcgtg acatagcatc tacagatact tgttttgcta acaaacatgc      8760
tgattttgac acatggttta gccagcgtgg tggtagttat actaatgaca aagcttgccc      8820
attgattgct gcagtcataa caagagaagt gggttttgtc gtgcctggtt tgcctggcac      8880
gatattacgc acaactaatg gtgactttt gcatttctta cctagagttt ttagtgcagt       8940
tggtaacatc tgttacacac catcaaaact tatagagtac actgactttg caacatcagc     9000
ttgtgttttg gctgctgaat gtacaatttt taaagatgct tctggtaagc cagtaccata      9060
ttgttatgat accaatgtac tagaaggttc tgttgcttat gaaagtttac gccctgacac      9120
acgttatgtg ctcatggatg gctctattat tcaatttcct aacacctacc ttgaaggttc      9180
tgttagagtg gtaacaactt ttgattctga gtactgtagg cacggcactt gtgaaagatc      9240
agaagctggt gtttgtgtat ctactagtgg tagatgggga cttaacaatg attattacag      9300
atctttacca ggagttttct gtggtgtaga tgctgtaaat ttacttacta atatgttac       9360
```

```
accactaatt caacctattg gtgctttgga catatcagca tctatagtag ctggtggtat    9420
tgtagctatc gtagtaacat gccttgccta ctattttatg aggtttagaa gagcttttgg    9480
tgaatacagt catgtagttg cctttaatac tttactattc cttatgtcat tcactgtact    9540
ctgtttaaca ccagtttact cattcttacc tggtgtttat tctgttattt acttgtactt    9600
gacattttat cttactaatg atgtttcttt tttagcacat attcagtgga tggttatgtt    9660 cacacccttta gtacctttct ggataacaat tgcttatatc atttgtattt ccacaaagca    9720
tttctattgg ttctttagta attacctaaa gagacgtgta gtctttaatg gtgtttcctt    9780
tagtactttt gaagaagctg cgctgtgcac cttttttgtta aataaagaaa tgtatctaaa    9840
gttgcgtagt gatgtgctat tacctcttac gcaatataat agatacttag ctctttataa    9900
taagtacaag tattttagtg gagcaatgga tacaactagc tacagagaag ctgcttgttg    9960
tcatctcgca aaggctctca atgacttcag taactcaggt tctgatgttc tttaccaacc   10020
accacaaacc tctatcacct cagctgtttt gcagagtggt tttagaaaaa tggcattccc   10080
atctggtaaa gttgagggtt gtatggtaca agtaacttgt ggtacaacta cacttaacgg   10140
tctttggctt gatgacgtag tttactgtcc aagacatgtg atctgcacct ctgaagacat   10200 gcttaacccct aattatgaag atttactcat tcgtaagtct aatcataatt tcttggtaca   10260
ggctggtaat gttcaactca gggttattgg acattctatg caaaattgtg tacttaagct   10320
taaggttgat acagccaatc ctaagacacc taagtataag tttgttcgca ttcaaccagg   10380
acagactttt tcagtgttag cttgttacaa tggttcacca tctggtgttt accaatgtgc   10440
tatgaggccc aatttcacta ttaagggttc attccttaat ggttcatgtg gtagtgttgg   10500
ttttaacata gattatgact gtgtctcttt ttgttacatg caccatatgg aattaccaac   10560
tggagttcat gctggcacag acttagaagg taactttat ggacctttttg ttgacaggca   10620 aacagcacaa gcagctggta cggacacaac tattacagtt aatgttttag cttggttgta   10680
cgctgctgtt ataaatggag acaggtggtt tctcaatcga tttaccacaa ctcttaatga   10740
ctttaacctt gtggctatga gtacaattta tgaacctcta acacaagacc atgttgacat   10800
actaggacct ctttctgctc aaactggaat tgccgtttta gatatgtgtg cttcattaaa   10860
agaattactg caaaatggta tgaatggacg taccatattg ggtagtgctt tattagaaga   10920
tgaatttaca cctttttgatg ttgttagaca atgctcaggt gttactttcc aaagtgcagt   10980
gaaaagaaca atcaagggta cacaccactg gttgttactc acaattttga cttcactttt   11040
agttttagtc cagagtactc aatggtcttt gttctttttt ttgtatgaaa atgcctttttt   11100 accttttgct atgggtatta ttgctatgtc tgcttttgca atgatgtttg tcaaacataa   11160
gcatgcattt ctctgtttgt ttttgttacc ttctcttgcc actgtagctt atttaatat   11220 ggtctatatg cctgctagtt gggtgatgcg tattatgaca tggttggata tggttgatac   11280
tagtttgtct ggttttaagc taaaagactg tgttatgtat gcatcagctg tagtgttact   11340
aatccttatg acagcaagaa ctgtgtatga tgatggtgct aggagagtgt ggacacttat   11400
gaatgtcttg acactcgttt ataaagttta ttatggtaat gctttagatc aagccatttc   11460
catgtgggct cttataatct ctgttacttc taactactca ggtgtagtta caactgtcat   11520
gtttttggcc agaggtattg ttttttatgtg tgttgagtat tgccctattt tcttcataac   11580
tggtaataca cttcagtgta ataatgctagt ttattgtttc ttaggctatt tttgtacttg   11640
ttactttggc ctcttttgtt tactcaaccg ctactttaga ctgactcttg gtgtttatga   11700
```

```
ttacttagtt tctacacagg agtttagata tatgaattca cagggactac tcccacccaa    11760
gaatagcata gatgccttca aactcaacat taaattgttg ggtgttggtg gcaaaccttg    11820
tatcaaagta gccactgtac agtctaaaat gtcagatgta aagtgcacat cagtagtctt    11880
actctcagtt ttgcaacaac tcagagtaga atcatcatct aaattgtggg ctcaatgtgt    11940
ccagttacac aatgacattc tcttagctaa agatactact gaagcctttg aaaaaatggt    12000
ttcactactt tctgttttgc tttccatgca gggtgctgta gacataaaca agctttgtga    12060
agaaatgctg gacaacaggg caaccttaca agctatagcc tcagagttta gttcccttcc    12120
atcatatgca gcttttgcta ctgctcaaga agcttatgag caggctgttg ctaatggtga    12180
ttctgaagtt gttcttaaaa agttgaagaa gtctttgaat gtggctaaat ctgaatttga    12240
ccgtgatgca gccatgcaac gtaagttgga aaagatggct gatcaagcta tgacccaaat    12300
gtataaacag gctagatctg aggacaagag ggcaaaagtt actagtgcta tgcagacaat    12360
gcttttcact atgcttagaa agttggataa tgatgcactc aacaacatta tcaacaatgc    12420
aagagatggt tgtgttccct tgaacataat acctcttaca acagcagcca aactaatggt    12480
tgtcatacca gactataaca catataaaaa tacgtgtgat ggtacaacat ttacttatgc    12540
atcagcattg tgggaaatcc aacaggttgt agatgcagat agtaaaattg ttcaacttag    12600
tgaaattagt atggacaatt cacctaattt agcatggcct cttattgtaa cagctttaag    12660
ggccaattct gctgtcaaat tacagaataa tgagcttagt cctgttgcac tacgacagat    12720
gtcttgtgct gccggtacta cacaaactgc ttgcactgat gacaatgcgt tagcttacta    12780
caacacaaca aagggaggta ggtttgtact tgcactgtta tccgatttac aggatttgaa    12840
atgggctaga ttccctaaga gtgatggaac tggtactatc tatacagaac tggaaccacc    12900
ttgtaggttt gttacagaca cacctaaagg tcctaaagtg aagtatttat actttattaa    12960
aggattaaac aacctaaata gaggtatggt acttggtagt ttagctgcca cagtacgtct    13020
acaagctggt aatgcaacag aagtgcctgc caattcaact gtattatctt tctgtgcttt    13080
tgctgtagat gctgctaaag cttacaaaga ttatctagct agtgggggac aaccaatcac    13140
taattgtgtt aagatgttgt gtacacacac tggtactggt caggcaataa cagttacacc    13200
ggaagccaat atggatcaag aatcctttgg tggtgcatcg tgttgtctgt actgccgttg    13260
ccacatagat catccaaatc ctaaaggatt ttgtgactta aaaggtaagt atgtacaaat    13320
acctacaact tgtgctaatg accctgtggg ttttacactt aaaaacacag tctgtaccgt    13380
ctgcggtatg tggaaaggtt atggctgtag ttgtgatcaa ctccgcgaac ccatgcttca    13440
gtcagctgat gcacaatcgt ttttaaacgg gtttgcggtg taagtgcagc ccgtcttaca    13500
ccgtgcggca caggcactag tactgatgtc gtatacaggg cttttgacat ctacaatgat    13560
aaagtagctg gttttgctaa attcctaaaa actaattgtt gtcgcttcca agaaaaggac    13620
gaagatgaca atttaattga ttcttacttt gtagttaaga gacacacttt ctctaactac    13680
caacatgaag aaacaattta aatttactt aaggattgtc cagctgttgc taaacatgac    13740
ttctttaagt ttagaataga cggtgacatg gtaccacata tatcacgtca acgtcttact    13800
aaatacacaa tggcagacct cgtctatgct ttaaggcatt ttgatgaagg taattgtgac    13860
acattaaaag aaatacttgt cacatacaat tgttgtgatg atgattattt caataaaaag    13920
gactggtatg attttgtaga aaacccagat atattacgcg tatacgccaa cttaggtgaa    13980
cgtgtacgcc aagctttgtt aaaaacagta caattctgtg atgccatgcg aaatgctggt    14040
attgttggtg tactgacatt agataatcaa gatctcaatg gtaactggta tgatttcggt    14100
```

```
gatttcatac aaaccacgcc aggtagtgga gttcctgttg tagattctta ttattcattg    14160
ttaatgccta tattaacctt gaccagggct ttaactgcag agtcacatgt tgacactgac    14220
ttaacaaagc cttacattaa gtgggatttg ttaaaatatg acttcacgga agagaggtta    14280
aaactctttg accgttattt taaatattgg gatcagacat accacccaaa ttgtgttaac    14340
tgtttggatg acagatgcat tctgcattgt gcaaacttta atgttttatt ctctacagtg    14400
ttcccaccta caagttttgg accactagtg agaaaaatat ttgttgatgg tgttccattt    14460
gtagtttcaa ctggatacca cttcagagag ctaggtgttg tacataatca ggatgtaaac    14520
ttacatagct ctagacttag ttttaaggaa ttacttgtgt atgctgctga ccctgctatg    14580
cacgctgctt ctggtaatct attactagat aaacgcacta cgtgcttttc agtagctgca    14640
cttactaaca atgttgcttt tcaaactgtc aaacccggta attttaacaa agacttctat    14700
gactttgctg tgtctaaggg tttctttaag gaaggaagtt ctgttgaatt aaaacacttc    14760
ttctttgctc aggatggtaa tgctgctatc agcgattatg actactatcg ttataatcta    14820
ccaacaatgt gtgatatcag acaactacta tttgtagttg aagttgttga taagtacttt    14880
gattgttacg atggtggctg tattaatgct aaccaagtca tcgtcaacaa cctagacaaa    14940
tcagctggtt ttccatttaa taaatggggt aaggctagac tttattatga ttcaatgagt    15000
tatgaggatc aagatgcact tttcgcatat acaaaacgta atgtcatccc tactataact    15060
caaatgaatc ttaagtatgc cattagtgca agaatagag ctcgcaccgt agctggtgtc    15120
tctatctgta gtactatgac caatagacag tttcatcaaa aattattgaa atcaatagcc    15180
gccactagag gagctactgt agtaattgga acaagcaaat tctatggtgg ttggcacaac    15240
atgttaaaaa ctgtttatag tgatgtagaa aaccctcacc ttatgggttg ggattatcct    15300
aaatgtgata gagccatgcc taacatgctt agaattatgg cctcacttgt tcttgctcgc    15360
aaacatacaa cgtgttgtag cttgtcacac cgtttctata gattagctaa tgagtgtgct    15420
caagtattga gtgaaatggt catgtgtggc ggttcactat atgttaaacc aggtggaacc    15480
tcatcaggag atgccacaac tgcttatgct aatagtgttt ttaacattg tcaagctgtc    15540 acggccaatg ttaatgcact tttatctact gatggtaaca aaattgccga taagtatgtc    15600
cgcaatttac aacacagact ttatgagtgt ctctatagaa atagagatgt tgacacagac    15660
tttgtgaatg agttttacgc atatttgcgt aaacatttct caatgatgat actctctgac    15720
gatgctgttg tgtgtttcaa tagcacttat gcatctcaag gtctagtggc tagcataaag    15780
aactttaagt cagttcttta ttatcaaaac aatgttttta tgtctgaagc aaaatgttgg    15840
actgagactg accttactaa aggacctcat gaattttgct ctcaacatac aatgctagtt    15900
aaacagggtg atgattatgt gtaccttcct tacccagatc catcaagaat cctaggggcc    15960
ggctgttttg tagatgatat cgtaaaaaca gatggtacac ttatgattga acggttcgtg    16020
tctttagcta tagatgctta cccacttact aaacatccta atcaggagta tgctgatgtc    16080
tttcatttgt acttacaata cataagaaag ctacatgatg agttaacagg acacatgtta    16140
gacatgtatt ctgttatgct tactaatgat aacactcaa ggtattggga acctgagttt    16200
tatgaggcta tgtacacacc gcatacagtc ttacaggctg ttggggcttg tgttctttgc    16260
aattcacaga cttcattaag atgtggtgct tgcatacgta gaccattctt atgttgtaaa    16320
tgctgttacg accatgtcat atcaacatca cataaattag tcttgtctgt taatccgtat    16380
gtttgcaatg ctccaggttg tgatgtcaca gatgtgactc aactttactt aggaggtatg    16440
```

```
agctattatt gtaaatcaca taaaccaccc attagttttc cattgtgtgc taatggacaa    16500 gttttttggtt tatataaaaa tacatgtgtt ggtagcgata atgttactga ctttaatgca   16560
attgcaacat gtgactggac aaatgctggt gattacattt tagctaacac ctgtactgaa   16620
agactcaagc tttttgcagc agaaacgctc aaagctactg aggagacatt taaactgtct   16680
tatggtattg ctactgtacg tgaagtgctg tctgacagag aattacatct ttcatgggaa   16740
gttggtaaac ctagaccacc acttaaccga aattatgtct ttactggtta tcgtgtaact   16800
aaaaacagta aagtacaaat aggagagtac acctttgaaa aaggtgacta tggtgatgct   16860
gttgtttacc gaggtacaac aacttacaaa ttaaatgttg gtgattattt tgtgctgaca   16920
tcacatacag taatgccatt aagtgcacct acactagtgc cacaagagca ctatgttaga   16980
attactggct tatacccaac actcaatatc tcagatgagt tttctagcaa tgttgcaaat   17040
tatcaaaagg ttggtatgca aaagtattct acactccagg gaccacctgg tactggtaag   17100
agtcattttg ctattggcct agctctctac tacccttctg ctcgcatagt gtatacagct   17160
tgctctcatg ccgctgttga tgcactatgt gagaaggcat taaaatattt gcctatagat   17220
aaatgtagta gaattatacc tgcacgtgct cgtgtagagt gttttgataa attcaaagtg   17280
aattcaacat tagaacagta tgtcttttgt actgtaaatg cattgcctga gacgacagca   17340
gatatagttg tctttgatga aatttcaatg gccacaaatt atgatttgag tgttgtcaat   17400
gccagattac gtgctaagca ctatgtgtac attggcgacc ctgctcaatt acctgcacca   17460
cgcacattgc taactaaggg cacactagaa ccagaatatt tcaattcagt gtgtagactt   17520
atgaaaacta taggtccaga catgttcctc ggaacttgtc ggcgttgtcc tgctgaaatt   17580
gttgacactg tgagtgcttt ggtttatgat aataagctta aagcacataa agacaaatca   17640
gctcaatgct ttaaaatgtt ttataagggt gttatcacgc atgatgtttc atctgcaatt   17700
aacaggccac aaataggcgt ggtaagagaa ttccttacac gtaaccctgc ttggagaaaa   17760
gctgtcttta tttcacctta taattcacag aatgctgtag cctcaaagat tttgggacta   17820
ccaactcaaa ctgttgattc atcacagggc tcagaatatg actatgtcat attcactcaa   17880
accactgaaa cagctcactc ttgtaatgta aacagattta atgttgctat taccagagca   17940
aaagtaggca tactttgcat aatgtctgat agagacctt atgacaagtt gcaatttaca   18000
agtcttgaaa ttccacgtag gaatgtggca actttacaag ctgaaaatgt aacaggactc   18060
tttaaagatt gtagtaaggt aatcactggg ttacatccta cacaggcacc tacacacctc   18120
agtgttgaca ctaaattcaa aactgaaggt ttatgtgttg acataccggg catacctaag   18180
gacatgacct atagaagact catctctatg atgggtttta aaatgaatta tcaagttaat   18240
ggttacccta acatgtttat cacccgcgaa gaagctataa gacatgtacg tgcatggatt   18300
ggcttcgatg tcgagggtg tcatgctact agagaagctg ttggtaccaa tttaccttta   18360
cagctaggtt tttctacagg tgttaaccta gttgctgtac ctacaggtta tgttgataca   18420
cctaataata cagatttttc cagagttagt gctaaaccac cgcctggaga tcaatttaaa   18480
cacctcatac cacttatgta caaggacttc cttggaatgt tagtgcgtat aaagattgta   18540
caaatgttaa gtgacacact taaaaatctc tctgacagag tcgtatttgt cttatgggca   18600
catggctttg agttgacatc tatgaagtat tttgtgaaaa taggacctga gcgcacctgt   18660
tgtctatgtg atagacgtgc cacatgcttt tccactgctt cagacactta tgcctgttgg   18720
catcattcta ttgatttga ttacgtctat aatccgttta tgattgatgt tcaacaatgg   18780
ggttttacag gtaacctaca aagcaaccat gatctgtatt gtcaagtcca tggtaatgca   18840
```

```
catgtagcta gttgtgatgc aatcatgact aggtgtctag ctgtccacga gtgctttgtt    18900
aagcgtgttg actggactat tgaatatcct ataattggtg atgaactgaa gattaatgcg    18960
gcttgtagaa aggttcaaca catggttgtt aaagctgcat tattagcaga caaattccca    19020
gttcttcacg acattggtaa ccctaaagct attaagtgtg tacctcaagc tgatgtagaa    19080
tggaagttct atgatgcaca gccttgtagt gacaaagctt ataaaataga agaattattc    19140
tattcttatg ccacacattc tgacaaattc acagatggtg tatgcctatt ttggaattgc    19200
aatgtcgata gatatcctgc taattccatt gtttgtagat ttgacactag agtgctatct    19260
aaccttaact tgcctggttg tgatggtggc agtttgtatg taaataaaca tgcattccac    19320
acaccagctt ttgataaaag tgcttttgtt aatttaaaac aattaccatt tttctattac    19380
tctgacagtc catgtgagtc tcatggaaaa caagtagtgt cagatataga ttatgtacca    19440
ctaaagtctg ctacgtgtat aacacgttgc aatttaggtg gtgctgtctg tagacatcat    19500
gctaatgagt acagattgta tctcgatgct tataacatga tgatctcagc tggctttagc    19560
ttgtgggttt acaaacaatt tgatacttat aacctctgga acactttttac aagacttcag    19620 agtttagaaa atgtggcttt taatgttgta aataagggac actttgatgg acaacagggt    19680
gaagtaccag tttctatcat taataacact gtttacacaa aagttgatgg tgttgatgta    19740
gaattgtttg aaaataaaac aacattacct gttaatgtag catttgagct ttgggctaag    19800
cgcaacatta aaccagtacc agaggtgaaa atactcaata atttgggtgt ggacattgct    19860
gctaatactg tgatctggga ctacaaaaga gatgctccag cacatatatc tactattggt    19920
gtttgttcta tgactgacat agccaagaaa ccaactgaaa cgatttgtgc accactcact    19980
gtcttttttg atggtagagt tgatggtcaa gtagacttat ttagaaatgc ccgtaatggt    20040
gttcttatta cagaaggtag tgttaaaggt ttacaaccat ctgtaggtcc caaacaagct    20100
agtcttaatg gagtcacatt aattggagaa gccgtaaaaa cacagttcaa ttattataag    20160
aaagttgatg gtgttgtcca acaattacct gaaacttact ttactcagag tagaaattta    20220
caagaattta aacccaggag tcaaatggaa attgatttct tagaattagc tatggatgaa    20280
ttcattgaac ggtataaatt agaaggctat gccttcgaac atatcgttta tggagatttt    20340
agtcatagtc agttaggtgg tttacatcta ctgattggac tagctaaacg ttttaaggaa    20400 tcacctttg aattagaaga ttttattcct atggacagta cagttaaaaa ctatttcata    20460
acagatgcgc aaacaggttc atctaagtgt gtgtgttctg ttattgattt attacttgat    20520
gattttgttg aaataataaa atcccaagat ttatctgtag tttctaaggt tgtcaaagtg    20580
actattgact atacagaaat ttcatttatg ctttggtgta aagatggcca tgtagaaaca    20640
ttttacccaa aattacaatc tagtcaagcg tggcaaccgg tgttgctat gcctaatctt    20700 tacaaaatgc aaagaatgct attagaaaag tgtgaccttc aaaattatgg tgatagtgca    20760
acattaccta aaggcataat gatgaatgtc gcaaaatata ctcaactgtg tcaatattta    20820
aacacattaa cattagctgt accctataat atgagagtta cattttggg tgctggttct    20880 gataaaggag ttgcaccagg tacagctgtt ttaagacagt ggttgcctac gggtacgctg    20940
cttgtcgatt cagatcttaa tgactttgtc tctgatgcag attcaacttt gattggtgat    21000
tgtgcaactg tacatacagc taataaatgg gatctcatta ttagtgatat gtacgaccct    21060
aagactaaaa atgttacaaa agaaaatgac tctaaagagg ttttttcac ttacatttgt    21120 gggtttatac aacaaaagct agctcttgga ggttccgtgg ctataaagat aacagaacat    21180
```

```
tcttggaatg ctgatctttq taagctcatg ggacacttcg catggtggac agcctttgtt   21240
actaatgtga atgcgtcatc atctgaagca ttttaattg  gatgtaatta tcttggcaaa   21300
ccacgcgaac aaatagatgg ttatgtcatg catgcaaatt acatattttg gaggaataca   21360
aatccaattc agttgtcttc ctattcttta tttgacatga gtaaatttcc ccttaaatta   21420
aggggtactg ctgttatgtc tttaaaagaa ggtcaaatca atgatatgat tttatctctt   21480
cttagtaaag gtagacttat aattagagaa aacaacagag ttgttatttc tagtgatgtt   21540
cttgttaaca actaaacgaa caatgtttgt ttttcttgtt ttattgccac tagtctctag   21600
tcagtgtgtt aatcttacaa ccagaactca attaccccct gcatacacta attctttcac   21660
acgtggtgtt tattaccctg acaaagtttt cagatcctca gttttacatt caactcagga   21720
cttgttctta cctttctttt ccaatgttac ttggttccat gctatacatg tctctgggac   21780
caatggtact aagaggtttg ataaccctgt cctaccattt aatgatggtg tttattttgc   21840
ttccactgag aagtctaaca taataagagg ctggattttt ggtactactt tagattcgaa   21900
gacccagtcc ctacttattg ttaataacgc tactaatgtt gttattaaag tctgtgaatt   21960 tcaatttttgt aatgatccat ttttgggtgt ttattaccac aaaaacaaca aaagttggat   22020
ggaaagtgag ttcagagttt attctagtgc gaataattgc acttttgaat atgtctctca   22080
gccttttctt atggaccttg aaggaaaaca gggtaatttc aaaaatctta gggaatttgt   22140
gtttaagaat attgatggtt attttaaaat atattctaag cacacgccta ttaatttagt   22200
gcgtgatctc cctcagggtt tttcggcttt agaaccattg gtagatttgc caataggtat   22260
taacatcact aggtttcaaa ctttacttgc tttacataga agttatttga ctcctggtga   22320
ttcttcttca ggttggacag ctggtgctgc agcttattat gtgggttatc ttcaacctag   22380
gacttttcta ttaaaatata tgaaaatgg aaccattaca gatgctgtag actgtgcact   22440 tgacccctctc tcagaaacaa agtgtacgtt gaaatccttc actgtagaaa aaggaatcta   22500
tcaaacttct aactttagag tccaaccaac agaatctatt gttagatttc ctaatattac   22560
aaacttgtgc ccttttggtg aagtttttaa cgccaccaga tttgcatctg tttatgcttg   22620
gaacaggaag agaatcagca actgtgttgc tgattattct gtcctatata attccgcatc   22680
attttccact tttaagtgtt atggagtgtc tcctactaaa ttaaatgatc tctgctttac   22740
taatgtctat gcagattcat ttgtaattag aggtgatgaa gtcagacaaa tcgctccagg   22800
gcaaactgga aagattgctg attataatta taaattacca gatgatttta caggctgcgt   22860
tatagcttgg aattctaaca atcttgattc taaggttggt ggtaattata attacctgta   22920
tagattgttt aggaagtcta atctcaaacc ttttgagaga gatatttcaa ctgaaatcta   22980
tcaggccgga agcacacctt gtaatggtgt tgaaggtttt aattgttact tcccttaca   23040 atcatatggt ttccaaccca ctaatggtgt tggttaccaa ccatacagag tagtagtact   23100
ttcttttgaa cttctacatg caccagcaac tgtttgtgga cctaaaaagt ctactaattt   23160
ggttaaaaac aaatgtgtca atttcaactt caatggttta acaggcacag gtgttcttac   23220
tgagtctaac aaaaagtttc tgcctttcca acaatttggc agagacattg ctgacactac   23280
tgatgctgtc cgtgatccac agacacttga gattcttgac attacaccat gttcttttgg   23340
tggtgtcagt gttataacac caggaacaaa tacttctaac caggttgctg ttctttatca   23400
ggatgttaac tgcacagaag tccctgttgc tattcatgca gatcaactta ctcctacttg   23460
gcgtgtttat tctacaggtt ctaatgtttt tcaaacacgt gcaggctgtt aatagggggc   23520
tgaacatgtc aacaactcat atgagtgtga catacccatt ggtgcaggta tatgcgctag   23580
```

```
ttatcagact cagactaatt ctcctcggcg ggcacgtagt gtagctagtc aatccatcat   23640
tgcctacact atgtcacttg gtgcagaaaa ttcagttgct tactctaata actctattgc   23700
catacccaca aattttacta ttagtgttac cacagaaatt ctaccagtgt ctatgaccaa   23760
gacatcagta gattgtacaa tgtacatttg tggtgattca actgaatgca gcaatctttt   23820
gttgcaatat ggcagttttt gtacacaatt aaaccgtgct ttaactggaa tagctgttga   23880
acaagacaaa aacacccaag aagttttttgc acaagtcaaa caaatttaca aaacaccacc   23940
aattaaagat tttggtggtt ttaatttttc acaaatatta ccagatccat caaaaccaag   24000
caagaggtca tttattgaag atctactttt caacaaagtg acacttgcag atgctggctt   24060
catcaaacaa tatggtgatt gccttggtga tattgctgct agagacctca tttgtgcaca   24120
aaagtttaac ggccttactg tttttgccacc tttgctcaca gatgaaatga ttgctcaata   24180
cacttctgca ctgttagcgg gtacaatcac ttctggttgg acctttggtg caggtgctgc   24240
attacaaata ccatttgcta tgcaaatggc ttataggttt aatggtattg gagttacaca   24300
gaatgttctc tatgagaacc aaaaattgat tgccaaccaa tttaatagtg ctattggcaa   24360
aattcaagac tcacttttctt ccacagcaag tgcacttgga aaacttcaag atgtggtcaa   24420
ccaaaatgca caagctttaa acacgcttgt taaacaactt agctccaatt ttggtgcaat   24480
ttcaagtgtt ttaaatgata tcctttcacg tcttgacaaa gttgaggctg aagtgcaaat   24540
tgataggttg atcacaggca gacttcaaag tttgcagaca tatgtgactc aacaattaat   24600
tagagctgca gaaatcagag cttctgctaa tcttgctgct actaaaatgt cagagtgtgt   24660
acttggacaa tcaaaaagag ttgatttttg tggaaagggc tatcatcta tgtccttccc   24720 tcagtcagca cctcatggtg tagtcttctt gcatgtgact tatgtccctg cacaagaaaa   24780
gaacttcaca actgctcctg ccatttgtca tgatggaaaa gcacactttc ctcgtgaagg   24840
tgtctttgtt tcaaatggca cacactggt tgtaacacaa aggaattttt atgaaccaca   24900
aatcattact acagacaaca catttgtgtc tggtaactgt gatgttgtaa taggaattgt   24960
caacaacaca gttatgatc ctttgcaacc tgaattagac tcattcaagg aggagttaga   25020
taaatatttt aagaatcata catcaccaga tgttgattta ggtgacatct ctggcattaa   25080
tgcttcagtt gtaaacattc aaaaagaaat tgaccgcctc aatgaggttg ccaagaattt   25140
aaatgaatct ctcatcgatc tccaagaact tggaaagtat gagcagtata taaaatggcc   25200
atggtacatt tggctaggtt ttatagctgg cttgattgcc atagtaatgg tgacaattat   25260
gctttgctgt atgaccagtt gctgtagttg tctcaagggc tgttgttctt gtggatcctg   25320
ctgcaaattt gatgaagacg actctgagcc agtgctcaaa ggagtcaaat tacattacac   25380
ataaacgaac ttatggattt gtttatgaga atcttcacaa ttggaactgt aactttgaag   25440
caaggtgaaa tcaaggatgc tactccttca gatttttgttc gcgctactgc aacgataccg   25500
atacaagcct cactcccttt cggatggctt attgttggcg ttgcacttct tgctgttttt   25560
cagagcgctt ccaaaatcat aaccctcaaa aagagatggc aactagcact ctccaagggt   25620
gttcactttg tttgcaactt gctgttgttg tttgtaacag tttactcaca ccttttgctc   25680
gttgctgctg gccttgaagc ccttttctc tatctttatg ctttagtcta cttcttgcag   25740 agtataaaact ttgtaagaat aataatgagg ctttggcttt gctggaaatg ccgttccaaa   25800
aacccattac tttatgatgc caactatttt ctttgctggc atactaattg ttacgactat   25860 tgtataccctt acaatagtgt aacttcttca attgtcatta cttcaggtga tggcacaaca   25920
```

```
agtcctattt ctgaacatga ctaccagatt ggtggttata ctgaaaaatg ggaatctgga  25980
gtaaaagact gtgttgtatt acacagttac ttcacttcag actattacca gctgtactca  26040
actcaattga gtacagacac tggtgttgaa catgttacct tcttcatcta aataaaatt   26100 gttgatgagc ctgaagaaca tgtccaaatt cacacaatcg acggttcatc cggagttgtt  26160
aatccagtaa tggaaccaat ttatgatgaa ccgacgacga ctactagcgt gcctttgtaa  26220
gcacaagctg atgagtacga acttatgtac tcattcgttt cggaagagac aggtacgtta  26280
atagttaata gcgtacttct ttttcttgct ttcgtggtat tcttgctagt tacactagcc  26340
atccttactg cgcttcgatt gtgtgcgtac tgctgcaata ttgttaacgt gagtcttgta  26400
aaaccttctt tttacgttta ctctcgtgtt aaaaatctga attcttctag agttcctgat  26460
cttctggtct aaacgaacta aatattatat tagttttct gtttggaact ttaattttag    26520
ccatggcaga ttccaacggt actattaccg ttgaagagct aaaaagctc cttgaacaat    26580 ggaacctagt aataggtttc ctattcctta catggatttg tcttctacaa tttgcctatg   26640
ccaacaggaa taggttttg tatataatta agttaatttt cctctggctg ttatggccag    26700
taactttagc ttgttttgtg cttgctgctg tttacagaat aaattggatc accggtggaa   26760
ttgctatcgc aatggcttgt cttgtaggct tgatgtggct cagctacttc attgcttct    26820 tcagactgtt tgcgcgtacg cgttccatgt ggtcattcaa tccagaaact aacattcttc   26880
tcaacgtgcc actccatggc actattctga ccagaccgct tctagaaagt gaactcgtaa   26940
tcggagctgt gatccttcgt ggacatcttc gtattgctgg acaccatcta ggacgctgtg   27000
acatcaagga cctgcctaaa gaaatcactg ttgctacatc acgaacgctt tcttattaca   27060
aattgggagc ttcgcagcgt gtagcaggtg actcaggttt tgctgcatac agtcgctaca   27120
ggattggcaa ctataaatta aacacagacc attccagtag cagtgacaat attgctttgc   27180
ttgtacagta agtgacaaca gatgtttcat ctcgttgact ttcaggttac tatagcagag   27240
atattactaa ttattatgag gacttttaaa gtttccattt ggaatcttga ttacatcata   27300
aacctcataa ttaaaaattt atctaagtca ctaactgaga ataaatattc tcaattagat   27360
gaagagcaac caatggagat tgattaaacg aacatgaaaa ttattctttt cttggcactg   27420
ataacactcg ctacttgtga gctttatcac taccaagagt gtgttagagg tacaacagta   27480
cttttaaaag aaccttgctc ttctggaaca tacgagggca attcaccatt tcatcctcta   27540
gctgataaca aatttgcact gacttgcttt agcactcaat ttgcttttgc ttgtcctgac   27600
ggcgtaaaac acgtctatca gttacgtgcc agatcagttt cacctaaact gttcatcaga   27660
caagaggaag ttcaagaact ttactctcca attttctta ttgttgcggc aatagtgttt   27720
ataacacttt gcttcacact caaaagaaag acagaatgat tgaactttca ttaattgact   27780
tctatttgtg ctttttagcc tttctgctat tccttgtttt aattatgctt attatctttt   27840
ggttctcact tgaactgcaa gatcataatg aaacttgtca cgcctaaacg aacatgaaat   27900
ttcttgtttt cttaggaatc atcacaactg tagctgcatt tcaccaagaa tgtagtttac   27960
agtcatgtac tcaacatcaa ccatatgtag ttgatgaccc gtgtcctatt cacttctatt   28020
ctaaatggta tattagagta ggagctgaaa atcagcacc tttaattgaa ttgtgcgtgg   28080
atgaggctgg ttctaaatca cccattcagt acatcgatat cggtaattat acagtttcct   28140
gtttaccttt tacaattaat tgccaggaac ctaaattggg tagtcttgta gtgcgttgtt   28200
cgttctatga agacttttta gagtatcatg acgttcgtgt tgtttagat ttcatctaaa    28260 cgaacaaact aaaatgtctg ataatggacc ccaaaatcag cgaaatgcac cccgcattac   28320
```

```
gtttggtgga ccctcagatt caactggcag taaccagaat ggagaacgca gtggggcgcg    28380
atcaaaacaa cgtcggcccc aaggtttacc caataatact gcgtcttggt tcaccgctct    28440
cactcaacat ggcaaggaag accttaaatt ccctcgagga caaggcgttc caattaacac    28500
caatagcagt ccagatgacc aaattggcta ctaccgaaga gctaccagac gaattcgtgg    28560
tggtgacggt aaaatgaaag atctcagtcc aagatggtat ttctactacc taggaactgg    28620
gccagaagct ggacttccct atggtgctaa caaagacggc atcatatggg ttgcaactga    28680
gggagccttg aatacaccaa agatcacat tggcacccgc aatcctgcta caatgctgc     28740 aatcgtgcta caacttcctc aaggaacaac attgccaaaa ggcttctacg cagaagggag    28800
cagaggcggc agtcaagcct cttctcgttc ctcatcacgt agtcgcaaca gttcaagaaa    28860
ttcaactcca ggcagcagta ggggaacttc tcctgctaga atggctggca atggcggtga    28920
tgctgctctt gctttgctgc tgcttgacag attgaaccag cttgagagca aaatgtctgg    28980
taaaggccaa caacaacaag ccaaactgt cactaagaaa tctgctgctg aggcttctaa    29040
gaagcctcgg caaaaacgta ctgccactaa agcatacaat gtaacacaag ctttcggcag    29100
acgtggtcca gaacaaaccc aaggaaattt tggggaccag gaactaatca gacaaggaac    29160
tgattacaaa cattggccgc aaattgcaca atttgccccc agcgcttcag cgttcttcgg    29220
aatgtcgcgc attggcatgg aagtcacacc ttcgggaacg tggttgacct acacaggtgc    29280
catcaaattg gatgacaaag atccaaattt caaagatcaa gtcattttgc tgaataagca    29340
tattgacgca tacaaaacat cccaccaac agagcctaaa aaggacaaaa agaagaaggc    29400
tgatgaaact caagccttac cgcagagaca gaagaaacag caaactgtga ctcttcttcc    29460
tgctgcagat ttggatgatt tctccaaaca attgcaacaa tccatgagca gtgctgactc    29520
aactcaggcc taaactcatg cagaccacac aaggcagatg ggctatataa acgttttcgc    29580
ttttccgttt acgatatata gtctactctt gtgcagaatg aattctcgta actacatagc    29640
acaagtagat gtagttaact ttaatctcac atagcaatct ttaatcagtg tgtaacatta    29700
gggaggactt gaaagagcca ccacattttc accgaggcca cgcggagtac gatcgagtgt    29760
acagtgaaca atgctaggga gagctgccta tatggaagag ccctaatgtg taaaattaat    29820
tttagtagtg ctatccccat gtgattttaa tagcttctta ggagaatgac aaaaaaaaaa    29880
aaaaaaaaaa aaaaaaaaaa aaa                                             29903

<210> SEQ ID NO 13
<211> LENGTH: 29720
<212> TYPE: DNA
<213> ORGANISM: SARS

<400> SEQUENCE: 13
gtttttacct acccaggaaa agccaaccaa cctcgatctc ttgtagatct gttctctaaa        60
cgaactttaa aatctgtgta gctgtcgctc ggctgcatgc ctagtgcacc tacgcagtat       120
aaacaataat aaattttact gtcgttgaca agaaacgagt aactcgtccc tcttctgcag       180
actgcttacg gtttcgtccg tgttgcagtc gatcatcagc ataccaggt ttcgtccggg        240 tgtgaccgaa aggtaagatg gagagccttg ttcttggtgt caacgagaaa acacacgtcc       300
aactcagttt gcctgtcctt caggttagag acgtgctagt gcgtggcttc ggggactctg       360
tggaagaggc cctatcggag gcacgtgaac acctcaaaaa tggcacttgt ggtcagtag       420 agctggaaaa aggcgtactg ccccagcttg aacagcccta tgtgttcatt aaacgttctg       480
```

```
atgccttaag caccaatcac ggccacaagg tcgttgagct ggttgcagaa atggacggca    540
ttcagtacgg tcgtagcggt ataacactgg gagtactcgt gccacatgtg ggcgaaaccc    600
caattgcata ccgcaatgtt cttcttcgta agaacggtaa taagggagcc ggtggtcata    660
gctatggcat cgatctaaag tcttatgact taggtgacga gcttggcact gatcccattg    720
aagattatga acaaaactgg aacactaagc atggcagtgg tgcactccgt gaactcactc    780
gtgagctcaa tggaggtgca gtcactcgct atgtcgacaa caatttctgt ggcccagatg    840
ggtaccctct tgattgcatc aaagattttc tcgcacgcgc gggcaagtca atgtgcactc    900
tttccgaaca acttgattac atcgagtcga agagaggtgt ctactgctgc cgtgaccatg    960
agcatgaaat tgcctggttc actgagcgct ctgataagag ctacgagcac cagacaccct   1020
tcgaaattaa gagtgccaag aaatttgaca cttttcaaagg ggaatgccca agtttgtgt   1080 ttcctcttaa ctcaaaagtc aaagtcattc aaccacgtgt tgaaagaaaa aagactgagg   1140
gtttcatggg gcgtatacgc tctgtgtacc ctgttgcatc tccacaggag tgtaacaata   1200
tgcacttgtc taccttgatg aaatgtaatc attgcgatga agtttcatgg cagacgtgcg   1260
actttctgaa agccacttgt gaacattgtg gcactgaaaa tttagttatt gaaggaccta   1320
ctacatgtgg gtacctacct actaatgctg tagtgaaaat gccatgtcct gcctgtcaag   1380
acccagagat tggacctgag catagtgttg cagattatca caaccactca aacattgaaa   1440
ctcgactccg caagggaggt aggactagat gtttttgagg ctgtgtgttt gcctatgttg   1500
gctgctataa taagcgtgcc tactgggttc ctcgtgctag tgctgatatt ggctcaggac   1560
atactggaat tactggtgac aatgtggaga ccttgaatga ggatctcctt gagatactga   1620
gtcgtgaacg tgttaacatt aacattgttg gcgatttttca tttgaatgaa gaggttgcca   1680
tcattttggc atctttctct gcttctacaa gtgcctttat tgacactata aagagtcttg   1740
attacaagtc tttcaaaacc attgttgagt cctgcggtaa ctataaagtt accaagggaa   1800
agcccgtaaa aggtgcttgg aacattggac aacagagatc agtttttaaca ccactgtgtg   1860 gttttcccctc acaggctgct ggtgttatca gatcaatttt tgcgcgcaca cttgatgcag   1920
caaaccactc aattcctgat ttgcaaagag cagctgtcac catacttgat ggtatttctg   1980
aacagtcatt acgtcttgtc gacgccatgg tttatacttc agacctgctc accaacagtg   2040
tcattattat ggcatatgta actggtggtc ttgtacaaca gacttctcag tggttgtcta   2100
atcttttggg cactactgtt gaaaaactca ggcctatctt tgaatggatt gaggcgaaac   2160
ttagtgcagg agttgaattt ctcaaggatg cttgggagat tctcaaattt ctcattacag   2220 gtgttttttga catcgtcaag ggtcaaatac aggttgcttc agataacatc aaggattgtg   2280
taaaatgctt cattgatgtt gttaacaagg cactcgaaat gtgcattgat caagtcacta   2340
tcgctggcgc aaagttgcga tcactcaact taggtgaagt cttcatcgct caaagcaagg   2400
gactttaccg tcagtgtata cgtggcaagg agcagctgca actactcatg cctcttaagg   2460
caccaaaaga agtaaccttt cttgaaggtg attcacatga cacagtactt acctctgagg   2520
aggttgttct caagaacggt gaactcgaag cactcgagac gcccgttgat agcttcacaa   2580
atggagctat cgttggcaca ccagtctgtg taaatggcct catgctctta gagattaagg   2640
acaaagaaca atactgcgca ttgtctcctg gtttactggc tacaaacaat gtctttcgct   2700 taaaagggg tgcaccaatt aaaggtgtaa ccttttggaga agatactgtt tgggaagttc   2760
aaggttacaa gaatgtgaga atcacatttg agcttgatga acgtgttgac aaagtgctta   2820
atgaaaagtg ctctgtctac actgttgaat ccggtaccga agttactgag tttgcatgtg   2880
```

```
ttgtagcaga ggctgttgtg aagactttac aaccagtttc tgatctcctt accaacatgg    2940
gtattgatct tgatgagtgg agtgtagcta cattctactt atttgatgat gctggtgaag    3000 aaaactttc atcacgtatg tattgttcct tttaccctcc agatgaggaa gaagaggacg     3060
atgcagagtg tgaggaagaa gaaattgatg aaacctgtga acatgagtac ggtacagagg    3120
atgattatca aggtctccct ctggaatttg gtgcctcagc tgaaacagtt cgagttgagg    3180
aagaagaaga ggaagactgg ctggatgata ctactgagca atcagagatt gagccagaac    3240
cagaacctac acctgaagaa ccagttaatc agtttactgg ttatttaaaa cttactgaca    3300
atgttgccat taaatgtgtt gacatcgtta aggaggcaca aagtgctaat cctatggtga    3360
ttgtaaatgc tgctaacata cacctgaaac atggtggtgg tgtagcaggt gcactcaaca    3420
aggcaaccaa tggtgccatg caaaaggaga gtgatgatta cattaagcta aatgccctc    3480 ttacagtagg agggtcttgt ttgctttctg acataatct tgctaagaag tgtctgcatg     3540
ttgttggacc taacctaaat gcaggtgagg acatccagct tcttaaggca gcatatgaaa    3600
atttcaattc acaggacatc ttacttgcac cattgttgtc agcaggcata tttggtgcta    3660
aaccacttca gtctttacaa gtgtgcgtgc agacggttcg tacacaggtt tatattgcag    3720
tcaatgacaa agctctttat gagcaggttg tcatggatta tcttgataac ctgaagccta    3780
gagtggaagc acctaaacaa gaggagccac caaacacaga agattccaaa actgaggaga    3840
aatctgtcgt acagaagcct gtcgatgtga agccaaaaat taaggcctgc attgatgagg    3900
ttaccacaac actggaagaa actaagtttc ttaccaataa gttactcttg tttgctgata    3960
tcaatggtaa gctttaccat gattctcaga acatgcttag aggtgaagat atgtctttcc    4020
ttgagaagga tgcaccttac atggtaggtg atgttatcac tagtggtgat atcacttgtg    4080
ttgtaatacc ctccaaaaag gctggtgcca ctactgagat gctctcaaga gctttgaaga    4140
aagtgccagt tgatgagtat ataaccacgt accctggaca aggatgtgct ggttatacac    4200
ttgaggaagc taagactgct cttaagaaat gcaaatctgc atttatgta ctaccttcag     4260 aagcacctaa tgctaaggaa gagattctag gaactgtatc ctggaatttg agagaaatgc    4320
ttgctcatgc tgaagagaca agaaaattaa tgcctatatg catggatgtt agagccataa    4380
tggcaaccat ccaacgtaag tataaaggaa ttaaaattca agagggcatc gttgactatg    4440
gtgtccgatt cttcttttat actagtaaag agcctgtagc ttctattatt acgaagctga    4500
actctctaaa tgagccgctt gtcacaatgc caattggtta tgtgacacat ggttttaatc    4560
ttgaagaggc tgcgcgctgt atgcgttctc ttaaagctcc tgccgtagtg tcagtatcat    4620
caccagatgc tgttactaca tataatggat acctcacttc gtcatcaaag acatctgagg    4680
agcactttgt tgaaacagtt tctttggctg gctcttacag agattggtcc tattcaggac    4740
agcgtacaga gttaggtgtt gaatttctta agcgtggtga caaaattgtg taccacactc    4800
tggagagccc cgtcgagttt catcttgacg gtgaggttct ttcacttgac aaactaaaga    4860
gtctcttatc cctgcgggag gttaagacta taaaagtgtt cacaactgtg acaacactag    4920
atctccacac acagcttgtg gatatgtcta tgacatatgg acagcagttt ggtccaacat    4980
acttggatgg tgctgatgtt acaaaaatta aacctcatgt aaatcatgag ggtaagactt    5040
tctttgtact acctagtgat gacacactac gtagtgaagc tttcgagtac taccatactc    5100
ttgatgagag ttttcttggt aggtacatgt ctgctttaaa ccacacaaag aaatggaaat    5160
ttcctcaagt tggtggtttta acttcaatta aatgggctga taacaattgt tatttgtcta    5220
```

```
gtgttttatt agcacttcaa cagcttgaag tcaaattcaa tgcaccagca cttcaagagg   5280
cttattatag agcccgtgct ggtgatgctg ctaacttttg tgcactcata ctcgcttaca   5340
gtaataaaac tgttggcgag cttggtgatg tcagagaaac tatgacccat cttctacagc   5400
atgctaattt ggaatctgca aagcgagttc ttaatgtggt gtgtaaacat tgtggtcaga   5460
aaactactac cttaacgggt gtagaagctg tgatgtatat gggtactcta tcttatgata   5520
atcttaagac aggtgtttcc attccatgtg tgtgtggtcg tgatgctaca caatatctag   5580
tacaacaaga gtcttctttt gttatgatgt ctgcaccacc tgctgagtat aaattacagc   5640
aaggtacatt cttatgtgcg aatgagtaca ctggtaacta tcagtgtggt cattacactc   5700
atataactgc taaggagacc ctctatcgta ttgacggagc tcaccttaca aagatgtcag   5760
agtacaaagg accagtgact gatgttttct acaaggaaac atcttacact acaaccatca   5820
agcctgtgtc gtataaactc gatggagtta cttacacaga gattgaacca aaattggatg   5880
ggtattataa aaaggataat gcttactata cagagcagcc tatagacctt gtaccaactc   5940
aaccattacc aaatgcgagt tttgataatt tcaaactcac atgttctaac acaaaatttg   6000
ctgatgattt aaatcaaatg acaggcttca caaagccagc ttcacgagag ctatctgtca   6060
cattcttccc agacttgaat ggcgatgtag tggctattga ctatagacac tattcagcga   6120
gtttcaagaa aggtgctaaa ttactgcata agccaattgt ttggcacatt aaccaggcta   6180
caaccaagac aacgttcaaa ccaaacactt ggtgtttacg ttgtctttgg agtacaaagc   6240
cagtagatac ttcaaaattca tttgaagttc tggcagtaga agacacacaa ggaatggaca   6300
atcttgcttg tgaaagtcaa caacccacct ctgaagaagt agtggaaaat cctaccatac   6360
agaaggaagt catagagtgt gacgtgaaaa ctaccgaagt tgtaggcaat gtcatactta   6420
aaccatcaga tgaaggtgtt aaagtaacac aggagttagg tcatgaggat cttatggctg   6480
cttatgtgga aaacacaagc attaccatta agaaacctaa tgagctttca ctagccttag   6540
gtttaaaaac aattgccact catggtattg ctgcaattaa tagtgttcct tggagtaaaa   6600
ttttggctta tgtcaaacca ttcttaggac aagcagcaat tacaacatca aattgcgcta   6660
agagattagc acaacgtgtg tttaacaatt atatgccta tgtgtttaca ttattgttcc   6720
aattgtgtac ttttactaaa agtaccaatt ctagaattag agcttcacta cctacaacta   6780
ttgctaaaaa tagtgttaag agtgttgcta aattatgttt ggatgccggc attaattatg   6840
tgaagtcacc caaattttct aaaattgttca caatcgctat gtggcattg ttgttaagta   6900 tttgcttagg ttctctaatc tgtgtaactg ctgcttttgg tgtactctta tctaattttg   6960
gtgctccttc ttattgtaat ggcgttagag aattgtatct taattcgtct aacgttacta   7020
ctatggattt ctgtgaaggt tcttttcctt gcagcatttg tttaagtgga ttagactccc   7080
ttgattctta tccagctctt gaaaccattc aggtgacgat tcatcgtac aagctagact   7140 tgacaatttt aggtctggcc gctgagtggg ttttggcata tatgttgttc acaaaattct   7200
tttatttatt aggtctttca gctataatgc aggtgttctt ggctatttt gctagtcatt   7260 tcatcagcaa ttcttggctc atgtggttta tcattagtat tgtacaaatg gcacccgttt   7320
ctgcaatggt taggatgtac atcttctttt cttctttcta ctacatatgg aagagctatg   7380
ttcatatcat ggatggttgc acctcttcga cttgcatgat gtgctataag cgcaatcgtg   7440
ccacacgcgt tgagtgtaca actattgtta atggcatgaa gagatctttc tatgtctatg   7500
caaatggagg ccgtggcttc tgcaagactc acaattggaa ttgtctcaat tgtgacacat   7560
tttgcactgg tagtacattc attagtgatg aagttgctcg tgatttgtca ctccagttta   7620
```

```
aaagaccaat caaccctact gaccagtcat cgtatattgt tgatagtgtt gctgtgaaaa   7680
atggcgcgct tcacctctac tttgacaagg ctggtcaaaa gacctatgag agacatccgc   7740
tctcccattt tgtcaattta gacaatttga gagctaacaa cactaaaggt tcactgccta   7800
ttaatgtcat agttttttgat ggcaagtcca aatgcgacga gtctgcttct aagtctgctt   7860
ctgtgtacta cagtcagctg atgtgccaac ctattctgtt gcttgaccaa gttcttgtat   7920
cagacgttgg agatagtact gaagtttccg ttaagatgtt tgatgcttat gtcgacacct   7980
tttcagcaac ttttagtgtt cctatggaaa aacttaaggc acttgttgct acagctcaca   8040
gcgagttagc aaagggtgta gctttagatg gtgtcctttc tacattcgtg tcagctgccc   8100
gacaaggtgt tgttgatacc gatgttgaca caaaggatgt tattgaatgt ctcaaacttt   8160
cacatcactc tgacttagaa gtgacaggtg acagttgtaa caatttcatg ctcacctata   8220
ataaggttga aaacatgacg cccagagatc ttggcgcatg tattgactgt aatgcaaggc   8280
atatcaatgc ccaagtagca aaagtcaca atgtttcact catctggaat gtaaaagact   8340
acatgtcttt atctgaacag ctgcgtaaac aaattcgtag tgctgccaag aagaacaaca   8400
taccttttag actaacttgt gctacaacta gacaggttgt caatgtcata actactaaaa   8460
tctcactcaa gggtggtaag attgttagta cttgttttaa acttatgctt aaggccacat   8520
tattgtgcgt tcttgctgca ttggtttgtt atatcgttat gccagtacat acattgtcaa   8580
tccatgatgg ttacacaaat gaaatcattg ttacaaagc cattcaggat ggtgtcactc   8640
gtgacatcat ttctactgat gattgttttg caaataaaca tgctggtttt gacgcatggt   8700
ttagccagcg tggcggttca tacaaaaatg acaaaagctg ccctgtagta gctgctatca   8760
ttacaagaga gattggtttc atagtgcctg gcttaccggg tactgtgctg agagcaatca   8820
atggtgactt cttgcatttt ctacctcgtg ttttagtgc tgttggcaac atttgctaca   8880
caccttccaa actcattgag tatagtgatt ttgctacctc tgcttgcgtt cttgctgctg   8940
agtgtacaat ttttaaggat gctatgggca aacctgtgcc atattgttat gacactaatt   9000
tgctagaggg ttctatttct tatagtgagc ttcgtccaga cactcgttat gtgcttatgg   9060
atggttccat catacagttt cctaacactt acctggaggg ttctgttaga gtagtaacaa   9120
cttttgatgc tgagtactgt agacatggta catgcgaaag gtcagaagta ggtatttgcc   9180
tatctaccag tggtagatgg gttcttaata atgagcatta cagagctcta tcaggagttt   9240
tctgtggtgt tgatgcgatg aatctcatag ctaacatctt tactcctctt gtgcaacctg   9300
tgggtgcttt agatgtgtct gcttcagtag tggctggtgg tattattgcc atattggtga   9360
cttgtgctgc ctactactt atgaaattca gacgtgtttt tggtgagtac aaccatgttg   9420
ttgctgctaa tgcactttg tttttgatgt ctttcactat actctgtctg gtaccagctt   9480
acagctttct gccgggagtc tactcagtct tttacttgta cttgacattc tatttcacca   9540
atgatgtttc attcttggct caccttcaat ggtttgccat gttttctcct attgtgcctt   9600
tttggataac agcaatctat gtattctgta tttctctgaa gcactgccat tggttcttta   9660
acaactatct taggaaaaga gtcatgttta atggagttac atttagtacc ttcgaggagg   9720
ctgctttgtg taccttttg ctcaacaagg aaatgtacct aaaattgcgt agcgagacac   9780
tgttgccact tacacagtat aacaggtatc ttgctctata taacaagtac aagtatttca   9840
gtggagcctt agatactacc agctatcgtg aagcagcttg ctgccactta gcaaaggctc   9900
taaatgactt tagcaactca ggtgctgatg ttctctacca accaccacag acatcaatca   9960
```

```
cttctgctgt tctgcagagt ggttttagga aaatggcatt cccgtcaggc aaagttgaag    10020
ggtgcatggt acaagtaacc tgtggaacta caactcttaa tggattgtgg ttggatgaca    10080
cagtatactg tccaagacat gtcatttgca cagcagaaga catgcttaat cctaactatg    10140
aagatctgct cattcgcaaa tccaaccata gctttcttgt tcaggctggc aatgttcaac    10200
ttcgtgttat tggccattct atgcaaaatt gtctgcttag gcttaaagtt gatacttcta    10260
accctaagac acccaagtat aaatttgtcc gtatccaacc tggtcaaaca ttttcagttc    10320
tagcatgcta caatggttca ccatctggtg tttatcagtg tgccatgaga cctaattata    10380
ccattaaagg ttcttttcctt aatggatcat gtggtagtgt tggttttaac attgattatg    10440
attgcgtgtc tttctgctat atgcatcata tggagcttcc aacaggagta cacgctggta    10500
ctgacttaga aggtaaattc tatggtccat tgttgacag acaaactgca caggctgcag    10560
gtacagacac aaccataaca ttaaatgttt tggcatggct gtatgctgct gttatcaatg    10620
gtgataggtg gtttcttaat agattcacca ctacttttgaa tgactttaac cttgtggcaa    10680
tgaagtacaa ctatgaacct ttgacacaag atcatgttga catattggga cctctttctg    10740
ctcaaacagg aattgccgtc ttagatatgt gtgctgcttt gaaagcgctg ctgcagaatg    10800
gtatgaatgg tcgtactatc cttggtagca ctattttaga agatgagttt acaccatttg    10860
atgttgttag acaatgctct ggtgttacct ccaaggtaa gttcaagaaa attgttaagg    10920
gcactcatca ttgatgcttt ttaactttct tgacatcact attgattctt gttcaaagta    10980
cacagtggtc actgttttc tttgtttacg agaatgcttt cttgccattt actcttggta    11040
ttatggcaat tgctgcatgt gctatgctgc ttgttaagca taagcacgca ttcttgtgct    11100
tgtttctgtt accttctctt gcaacagttg cttactttaa tatggtctac atgcctgcta    11160
gctgggtgat gcgtatcatg acatggcttg aattggctga cactagcttg tctggttata    11220
ggcttaagga ttgtgttatg tatgcttcag ctttagtttt gcttattctc atgacagctc    11280
gcactgttta tgatgatgct gctagacgtg tttggacact gatgaatgtc attacacttg    11340
tttacaaagt ctactatggt aatgctttag atcaagctat ttccatgtgg gccttagtta    11400
tttctgtaac ctctaactat tctggtgtcg ttacgactat catgttttta gctagagcta    11460
tagtgtttgt gtgtgttgag tattacccat tgttatttat tactggcaac accttacagt    11520
gtatcatgct tgtttattgt ttcttaggct attgttgctg ctgctacttt ggccttttct    11580
gtttactcaa ccgttacttc aggcttactc ttggtgttta tgactacttg gtctctacac    11640
aagaatttag gtatatgaac tcccagggc ttttgcctcc taagagtagt attgatgctt    11700
tcaagcttaa cattaagttg ttgggtattg gaggtaaacc atgtatcaag gttgctactg    11760
tacagtctaa aatgtctgac gtaaagtgca catctgtggt actgctctcg gttcttcaac    11820
aacttagagt agagtcatct tctaaattgt gggcacaatg tgtacaactc acaatgata    11880
ttcttcttgc aaaagacaca actgaagctt tcgagaagat ggtttctctt ttgtctgttt    11940
tgctatccat gcagggtgct gtagacatta ataggttgtg cgaggaaatg ctcgataacc    12000
gtgctactct tcaggctatt gcttcagaat ttagttcttt accatcatat gccgcttatg    12060
ccactgccca gaggcctat gagcaggctg tagctaatgg tgattctgaa gtcgttctca    12120
aaaagttaaa gaaatctttg aatgtggcta atctgagtt tgaccgtgat gctgccatgc    12180
aacgcaagtt ggaaaagatg gcagatcagg ctatgaccca aatgtacaaa caggcaagat    12240
ctgaggacaa gagggcaaaa gtaactagtg ctatgcaaac aatgctcttc actatgctta    12300
ggaagcttga taatgatgca cttaacaaca ttatcaacaa tgcgcgtgat ggttgtgttc    12360
```

```
cactcaacat cataccattg actacagcag ccaaactcat ggttgttgtc cctgattatg    12420
gtacctacaa gaacacttgt gatggtaaca cctttacata tgcatctgca ctctgggaaa    12480
tccagcaagt tgttgatgcg gatagcaaga ttgttcaact tagtgaaatt aacatggaca    12540
attcaccaaa tttggcttgg cctcttattg ttacagctct aagagccaac tcagctgtta    12600
aactacagaa taatgaactg agtccagtag cactacgaca gatgtcctgt gcggctggta    12660
ccacacaaac agcttgtact gatgacaatg cacttgccta ctataacaat tcgaagggag    12720
gtaggtttgt gctggcatta ctatcagacc accaagatct caaatgggct agattcccta    12780
agagtgatgg tacaggtaca atttacgcag aactggaacc accttgtagg tttgttacag    12840
acacaccaaa agggcctaaa gtgaaatact tgtacttcat caaaggctta aacaacctaa    12900
atagaggtat ggtgctgggc agtttagctg ctacagtacg tcttcaggct ggaaatgcta    12960
cagaagtacc tgccaattca actgtgcttt ccttctgtgc ttttgcagta gaccctgcta    13020
aagcatataa ggattaccta gcaagtggag gacaaccaat caccaactgt gtgaagatgt    13080
tgtgtacaca cactggtaca ggacaggcaa ttactgtaac accagaagct aacatggacc    13140
aagagtcctt tggtggtgct tcatgttgtc tgtattgtag atgccacatt gaccatccaa    13200
atcctaaagg attctgtgac ttgaaaggta agtacgtcca aatacctacc acttgtgcta    13260
atgacccagt gggttttaca cttagaaaca cagtctgtac cgtctgcgga atgtggaaag    13320
gttatggctg tagttgtgac caactccgcg aacccttgat gcagtctgcg gatgcatcaa    13380 cgttttaaa cgggtttgcg gtgtaagtgc agcccgtctt acaccgtgcg gcacaggcac    13440
tagtactgat gtcgtctaca ggcttttga tatttacaac gaaaagttg ctggttttgc    13500 aaagttccta aaactaatt gctgtcgctt ccaggagaag gatgaggaag caatttatt    13560 agactcttac tttgtagtta agaggcatac tatgtctaac taccaacatg aagagactat    13620
ttataacttg gttaaagatt gtccagcggt tgctgtccat gactttttca gtttagagt    13680 agatggtgac atggtaccac atatatcacg tcagcgtcta actaaataca caatggctga    13740
tttagtctat gctctacgtc attttgatga gggtaattgt gatacattaa agaaatact    13800 cgtcacatac aattgctgtg atgatgatta tttcaataag aaggattggt atgacttcgt    13860
agagaatcct gacatcttac gcgtatatgc taacttaggt gagcgtgtac gccaatcatt    13920
attaaagact gtacaattct gcgatgctat gcgtgatgca ggcattgtag gcgtactgac    13980
attagataat caggatctta atgggaactg gtacgatttc ggtgatttcg tacaagtagc    14040
accaggctgc ggagttccta ttgtggattc atattactca ttgctgatgc ccatcctcac    14100
tttgactagg gcattggctg ctgagtccca tatggatgct gatctcgcaa aaccacttat    14160
taagtgggat ctgctgaaat atgatttac ggaagagaga ctttgtctct tcgaccgtta    14220
ttttaaatat tgggaccaga cataccatcc caattgtatt aactgttgg atgataggtg    14280 tatccttcat tgtgcaaact ttaatgtgtt attttctact gtgtttccac ctacaagttt    14340
tggaccacta gtaagaaaaa tatttgtaga tggtgttcct tttgttgttt caactggata    14400 ccatttcgt gagttaggag tcgtacataa tcaggatgta aacttacata gctcgcgtct    14460
cagtttcaag gaactttag tgtatgctgc tgatccagct atgcatgcag cttctggcaa    14520
tttattgcta gataaacgca ctacatgctt tcagtagct gcactaacaa acaatgttgc    14580
ttttcaaact gtcaaacccg gtaatttaa taaagacttt tatgactttg ctgtgtctaa    14640
aggtttcttt aaggaaggaa gttctgttga actaaaacac ttcttctttg ctcaggatgg    14700
```

```
caacgctgct atcagtgatt atgactatta tcgttataat ctgccaacaa tgtgtgatat    14760
cagacaactc ctattcgtag ttgaagttgt tgataaatac tttgattgtt acgatggtgg    14820
ctgtattaat gccaaccaag taatcgttaa caatctggat aaatcagctg gtttcccatt    14880
taataaatgg ggtaaggcta gactttatta tgactcaatg agttatgagg atcaagatgc    14940
acttttcgcg tatactaagc gtaatgtcat ccctactata actcaaatga atcttaagta    15000
tgccattagt gcaaagaata gagctcgcac cgtagctggt gtctctatct gtagtactat    15060
gacaaataga cagtttcatc agaaattatt gaagtcaata gccgccacta gaggagctac    15120
tgtggtaatt ggaacaagca agttttacgg tggctggcat aatatgttaa aaactgttta    15180
cagtgatgta gaaactccac accttatggg ttgggattat ccaaaatgtg acagagccat    15240
gcctaacatg cttaggataa tggcctctct tgttcttgct cgcaaacata cacttgctg    15300 taacttatca caccgtttct acaggttagc taacgagtgt gcgcaagtat taagtgagat    15360
ggtcatgtgt ggcggctcac tatatgttaa accaggtgga acatcatccg gtgatgctac    15420
aactgcttat gctaatagtg tctttaacat tgtcaagct gttacagcca atgtaaatgc    15480
acttctttca actgatggta ataagatagc tgacaagtat gtccgcaatc tacaacacag    15540
gctctatgag tgtctctata gaaataggga tgttgatcat gaattcgtgg atgagtttta    15600
cgcttacctg cgtaaacatt tctccatgat gattctttct gatgatgccg ttgtgtgcta    15660
taacagtaac tatgcggctc aaggtttagt agctagcatt aagaaccttta aggcagttct    15720 ttattatcaa acaatgtgt tcatgtctga ggcaaaatgt tggactgaga ctgaccttac    15780
taaaggacct cacgaatttt gctcacagca tacaatgcta gttaaacaag gagatgatta    15840
cgtgtacctg ccttacccag atccatcaag aatattaggc gcaggctgtt ttgtcgatga    15900
tattgtcaaa acagatggta cacttatgat tgaaaggttc gtgtcactgg ctattgatgc    15960
ttacccactt acaaaacatc ctaatcagga gtatgctgat gtctttcact tgtatttaca    16020
atacattaga aagttacatg atgagcttac tggccacatg ttggacatgt attccgtaat    16080
gctaactaat gataacacct cacggtactg ggaacctgag ttttatgagg ctatgtacac    16140
accacataca gtcttgcagg ctgtaggtgt ttgtgtattg tgcaattcac agactcact    16200 tcgttgcggt gcctgtatta ggagaccatt cctatgttgc aagtgctgct atgaccatgt    16260
catttcaaca tcacacaaat tagtgttgtc tgttaatccc tatgtttgca atgccccagg    16320
ttgtgatgtc actgatgtga cacaactgta tctaggaggt atgagctatt attgcaagtc    16380
acataagcct cccattagtt ttccattatg tgctaatggt caggttttg gtttatacaa    16440 aaacacatgt gtaggcagtg acaatgtcac tgacttcaat gcgatagcaa catgtgattg    16500
gactaatgct ggcgattaca cacttgccaa cacttgtact gagagactca gcttttcgc    16560 agcagaaacg ctcaaagcca ctgaggaaac atttaagctg tcatatggta ttgctactgt    16620
acgcgaagta ctctctgaca gagaattgca tctttcatgg gaggttggaa acctagacc    16680 accattgaac agaaactatg tctttactgg ttaccgtgta actaaaaata gtaaagtaca    16740
gattggagag tacaccctt aaaaaggtga ctatggtgat gctgttgtgt acagaggtac    16800
tacgacatac aagttgaatg ttggtgatta cttgtgttg acatctcaca ctgtaatgcc    16860
acttagtgca cctactctag tgccacaaga gcactatgtg agaattactg gcttgtaccc    16920
aacactcaac atctcagatg agttttctag caatgttgca aattatcaaa aggtcggcat    16980
gcaaaagtac tctacactcc aaggaccacc tggtactggt aagagtcatt ttgccatcgg    17040
acttgctctc tattacccat ctgctcgcat agtgtatacg gcatgctctc atgcagctgt    17100
```

```
tgatgccctα tgtgaaaagg cattaaaata tttgcccata gataaatgta gtagaatcat  17160
acctgcgcgt gcgcgcgtag agtgttttga taaattcaaa gtgaattcaa cactagaaca  17220
gtatgttttc tgcactgtaa atgcattgcc agaaacaact gctgacattg tagtctttga  17280
tgaaatctct atggctacta attatgactt gagtgttgtc aatgctagac ttcgtgcaaa  17340
acactacgtc tatattggcg atcctgctca attaccagcc ccccgcacat tgctgactaa  17400
aggcacacta gaaccagaat attttaattc agtgtgcaga cttatgaaaa caataggtcc  17460
agacatgttc cttggaactt gtcgccgttg tcctgctgaa attgttgaca ctgtgagtgc  17520
tttagtttat gacaataagc taaaagcaca caaggataag tcagctcaat gcttcaaaat  17580
gttctacaaa ggtgttatta cacatgatgt tcatctgca atcaacagac ctcaaatagg  17640
cgttgtaaga gaatttctta cacgcaatcc tgcttggaga aaagctgttt ttatctcacc  17700
ttataattca cagaacgctg tagcttcaaa aatcttagga ttgcctacgc agactgttga  17760
ttcatcacag ggttctgaat atgactatgt catattcaca caaactactg aaacagcaca  17820
ctcttgtaat gtcaaccgct tcaatgtggc tatcacaagg gcaaaaattg gcattttgtg  17880
cataatgtct gatagagatc tttatgacaa actgcaattt acaagtctag aaataccacg  17940
tcgcaatgtg gctacattac aagcagaaaa tgtaactgga cttttttaagg actgtagtaa  18000 gatcattact ggtcttcatc ctacacaggc acctacacac ctcagcgttg atataaagtt  18060
caagactgaa ggattatgtg ttgacatacc aggcatacca aaggacatga cctaccgtag  18120
actcatctct atgatgggtt tcaaaatgaa ttaccaagtc aatggttacc ctaatatgtt  18180
tatcacccgc gaagaagcta ttcgtcacgt tcgtgcgtgg attggctttg atgtagaggg  18240
ctgtcatgca actagagatg ctgtgggtac taacctacct ctccagctag gatttttctac  18300 aggtgttaac ttagtagctg taccgactgg ttatgttgac actgaaaata cacagaatt  18360 caccagagtt aatgcaaaac ctccaccagg tgaccagttt aaacatctta taccactcat  18420
gtataaaggc ttgccctgga atgtagtgcg tattaagata gtacaaatgc tcagtgatac  18480
actgaaagga ttgtcagaca gagtcgtgtt cgtcctttgg gcgcatggct ttgagcttac  18540
atcaatgaag tactttgtca agattggacc tgaaagaacg tgttgtctgt gtgacaaacg  18600
tgcaacttgc ttttctactt catcagatac ttatgcctgc tggaatcatt ctgtgggttt  18660
tgactatgtc tataacccat ttatgattga tgttcagcag tggggcttta cgggtaacct  18720
tcagagtaac catgaccaac attgccaggt acatggaaat gcacatgtgg ctagttgtga  18780
tgctatcatg actagatgtt tagcagtcca tgagtgcttt gttaagcgcg ttgattggtc  18840
tgttgaatac cctattatag gagatgaact gagggttaat tctgcttgca gaaaagtaca  18900
acacatggtt gtgaagtctg ccctcctggc tgataagttt ccagttcttc atgacattgg  18960
aaatccaaag gctatcaagt gtgtgcctca ggctgaagta gaatggaagt tctacgatgc  19020
tcagccatgt agtgacaaag cttacaaaat agaggagctc ttctattctt atgctacaca  19080
tcacgataaa ttcactgatg gtgtttgttt gttttggaat tgtaacgttg atcgttaccc  19140
agccaatgca attgtgtgta ggtttgacac aagagtcttg tcaaacttga acttaccagg  19200
ctgtgatggt ggtagtttgt atgtgaataa gcatgcattc cacactccag cttttcgataa  19260 aagtgcattt actaatttaa agcaattgcc tttcttttac tattctgata gtccttgtga  19320
gtctcatggc aaacaagtag tgtcggatat tgattatgtt ccactcaaat ctgctacgtg  19380
tattacacga tgcaatttag gtggtgctgt ttgcagacac catgcaaatg agtaccgaca  19440
```

```
gtacttggat gcatataata tgatgatttc tgctggattt agcctatgga tttacaaaca    19500
atttgatact tataacctgt ggaatacatt taccaggtta cagagtttag aaaatgtggc    19560
ttataatgtt gttaataaag gacactttga tggacacgcc ggcgaagcac ctgtttccat    19620
cattaataat gctgtttaca caaaggtaga tggtattgat gtggagatct ttgaaaataa    19680
gacaacactt cctgttaatg ttgcatttga gctttgggct aagcgtaaca ttaaaccagt    19740
gccagagatt aagatactca ataatttggg tgttgatatc gctgctaata ctgtaatctg    19800
ggactataaa agagaagccc cagcacatgt atctacaata ggtgtctgca caatgactga    19860
cattgccaag aaacctactg agagtgcttg ttcttcactt actgtcttgt ttgatggtag    19920
agtggaagga caggtagacc tttttagaaa cgcccgtaat ggtgttttaa taacagaagg    19980
ttcagtcaaa ggtctaacac cttcaaaggg accagcacaa gctagcgtca atggagtcac    20040
attaattgga gaatcagtaa aaacacagtt taactacttt aagaaagtag acggcattat    20100
tcaacagttg cctgaaacct actttactca gagcagagac ttagaggatt ttaagcccag    20160
atcacaaatg gaaactgact ttctcgagct cgctatggat gaattcatac agcgatataa    20220
gctcgagggc tatgccttcg aacacatcgt ttatggagat ttcagtcatg acaacttgg    20280 cggtcttcat ttaatgatag gcttagccaa gcgctcacaa gattcaccac ttaaattaga    20340
ggattttatc cctatggaca gcacagtgaa aaattacttc ataacagatg cgcaaacagg    20400
ttcatcaaaa tgtgtgtgtt ctgtgattga tcttttactt gatgactttg tcgagataat    20460
aaagtcacaa gatttgtcag tgatttcaaa agtggtcaag gttacaattg actatgctga    20520
gatttcattc atgctttggt gtaaggacgg acatgttgaa accttctacc aaaactaca    20580 agcaagtcaa gcgtggcaac caggtgttgc gatgcctaac ttgtacaaga tgcaaagaat    20640
gcttcttgaa aagtgtgacc ttcagaatta tggtgaaaat gctgttatac caaaggaat    20700 aatgatgaat gtcgcaaagt atactcaact gtgtcaatac ttaaatacac ttactttagc    20760
tgtaccctac aacatgagag ttattcactt tggtgctggc tctgataaag agttgcacc    20820 aggtacagct gtgctcagac aatggttgcc aactggcaca ctacttgtcg attcagatct    20880
taatgacttc gtctccgacg cagattctac tttaattgga gactgtgcaa cagtacatac    20940
ggctaataaa tgggacctta ttattagcga tatgtatgac cctaggacca acatgtgac    21000 aaaagagaat gactctaaag aagggttttt cacttatctg tgtggattta taaagcaaaa    21060
actagccctg ggtggttcta tagctgtaaa gataacagag cattcttgga atgctgacct    21120
ttacaagctt atgggccatt tctcatggtg gacagctttt gttacaaatg taaatgcatc    21180
atcatcggaa gcatttttaa ttggggctaa ctatcttggc aagccgaagg aacaaattga    21240
tggctatacc atgcatgcta actacatttt ctggaggaac acaaatccta tccagttgtc    21300
ttcctattca ctctttgaca tgagcaaatt tcctcttaaa ttaagaggaa ctgctgtaat    21360
gtctcttaag gagaatcaaa tcaatgatat gatttattct cttctggaaa aaggtaggct    21420
tatcattaga gaaaacaaca gagttgtggt ttcaagtgat attcttgtta caactaaac    21480 gaacatgttt attttcttat tatttcttac tctcactagt ggtagtgacc ttgaccggtg    21540
caccactttt gatgatgttc aagctcctaa ttacactcaa catacttcat ctatgagggg    21600
ggtttactat cctgatgaaa ttttagatc agacactctt tatttaactc aggatttatt    21660
tcttccattt tattctaatg ttacagggtt tcatactatt aatcatacgt ttggcaaccc    21720
tgtcatacct tttaaggatg gtatttattt tgctgccaca gagaaatcaa atgttgtccg    21780
tggttgggtt tttggttcta ccatgaacaa caagtcacag tcggtgatta ttattaacaa    21840
```

```
ttctactaat gttgttatac gagcatgtaa ctttgaattg tgtgacaacc ctttctttgc   21900
tgtttctaaa cccatgggta cacagacaca tactatgata ttcgataatg catttaattg   21960
cactttcgag tacatatctg atgccttttc gcttgatgtt tcagaaaagt caggtaattt   22020
taaacactta cgagagtttg tgtttaaaaa taaagatggg tttctctatg tttataaggg   22080
ctatcaacct atagatgtag ttcgtgatct accttctggt tttaacactt tgaaacctat   22140
ttttaagttg cctcttggta ttaacattac aaattttaga gccattctta cagccttttc   22200
acctgctcaa gacatttggg gcacgtcagc tgcagcctat tttgttggct atttaaagcc   22260
aactacattt atgctcaagt atgatgaaaa tggtacaatc acagatgctg ttgattgttc   22320
tcaaaatcca cttgctgaac tcaaatgctc tgttaagagc tttgagattg acaaaggaat   22380
ttaccagacc tctaatttca gggttgttcc ctcaggagat gttgtgagat ccctaatat   22440 tacaaacttg tgtccttttg gagaggtttt taatgctact aaattccctt ctgtctatgc   22500
atgggagaga aaaaaatttt ctaattgtgt tgctgattac tctgtgctct acaactcaac   22560
atttttttca acctttaagt gctatggcgt ttctgccact aagttgaatg atctttgctt   22620
ctccaatgtc tatgcagatt cttttgtagt caagggagat gatgtaagac aaatagcgcc   22680
aggacaaact ggtgttattg ctgattataa ttataaattg ccagatgatt tcatgggttg   22740
tgtccttgct tggaatacta ggaacattga tgctacttca actggtaatc ataattataa   22800
atataggtat cttagacatg gcaagcttag gccctttgag agagacatat ctaatgtgcc   22860
tttctcccct gatggcaaac cttgcacccc acctgctctt aattgttatt ggccattaaa   22920
tgattatggt ttttacacca ctactggcat tggctaccaa ccttacagag ttgtagtact   22980
ttcttttgaa cttttaaatg caccggccac ggtttgtgga ccaaaattat ccactgacct   23040
tattaagaac cagtgtgtca attttaattt taatggactc actggtactg gtgtgttaac   23100
tccttcttca aagagatttc aaccatttca acaatttggc cgtgatgttt ctgatttcac   23160
tgattccgtt cgagatccta aaacatctga atattagac atttcacctt gctcttttgg   23220
gggtgtaagt gtaattacac ctggaacaaa tgcttcatct gaagttgctg ttctatatca   23280
agatgttaac tgcactgatg tttctacagc aattcatgca gatcaactca caccagcttg   23340
gcgcatatat tctactggaa acaatgtatt ccagactcaa gcaggctgtc ttataggagc   23400
tgagcatgtc gacacttctt atgagtgcga cattcctatt ggagctggca tttgtgctag   23460
ttaccataca gtttctttat tacgtagtac tagccaaaaa tctattgtgg cttatactat   23520
gtctttaggt gctgatagtt caattgctta ctctaataac accattgcta tacctactaa   23580
cttttcaatt agcattacta cagaagtaat gcctgtttct atggctaaaa cctccgtaga   23640
ttgtaatatg tacatctgcg gagattctac tgaatgtgct aatttgcttc tccaatatgg   23700
tagcttttgc acacaactaa atcgtgcact ctcaggtatt gctgctgaac aggatcgcaa   23760
cacacgtgaa gtgttcgctc aagtcaaaca aatgtacaaa accccaactt gaaatattt   23820 tggtggtttt aatttttcac aaatattacc tgaccctcta agccaacta agaggtcttt   23880 tattgaggac ttgctcttta ataaggtgac actcgctgat gctggcttca tgaagcaata   23940
tggcgaatgc ctaggtgata ttaatgctag agatctcatt tgtgcgcaga gttcaatgg   24000 acttacagtg ttgccaccct gctcactga tgatatgatt gctgcctaca cggctgctct   24060
agttagtggt actgccactg ctggatggac atttggtgct ggcgctgctc ttcaaatacc   24120
ttttgctatg caaatggcat ataggttcaa tggcattgga gttacccaaa atgttctcta   24180
```

```
tgagaaccaa aaacaaatcg ccaaccaatt taacaaggcg attagtcaaa ttcaagaatc    24240
acttacaaca acatcaactg cattgggcaa gctgcaagac gttgttaacc agaatgctca    24300
agcattaaac acacttgtta aacaacttag ctctaatttt ggtgcaattt caagtgtgct    24360
aaatgatatc ctttcgcgac ttgataaagt cgaggcggag gtacaaattg acaggttaat    24420
tacaggcaga cttcaaagcc ttcaaaccta tgtaacacaa caactaatca gggctgctga    24480
aatcagggct tctgctaatc ttgctgctac taaaatgtct gagtgtgttc ttggacaatc    24540
aaaaagagtt gacttttgtg gaaagggcta ccaccttatg tccttcccac aagcagcccc    24600
gcatggtgtt gtcttcctac atgtcacgta tgtgccatcc caggagagga acttcaccac    24660
agcgccagca atttgtcatg aaggcaaagc atacttccct cgtgaaggtg ttttgtgtt    24720 taatggcact tcttggttta ttacacagag gaacttcttt tctccacaaa taattactac    24780
agacaataca tttgtctcag gaaattgtga tgtcgttatt ggcatcatta acaacacagt    24840
ttatgatcct ctgcaacctg agctcgactc attcaaagaa gagctggaca agtacttcaa    24900
aaatcataca tcaccagatg ttgatcttgg cgacatttca ggcattaacg cttctgtcgt    24960
caacattcaa aaagaaattg accgcctcaa tgaggtcgct aaaaatttaa atgaatcact    25020
cattgacctt caagaattgg gaaaatatga gcaatatatt aaatggcctt ggtatgtttg    25080
gctcggcttc attgctggac taattgccat cgtcatggtt acaatcttgc tttgttgcat    25140
gactagttgt tgcagttgcc tcaagggtgc atgctcttgt ggttcttgct gcaagtttga    25200
tgaggatgac tctgagccag ttctcaaggg tgtcaaatta cattacacat aaacgaactt    25260
atggatttgt ttatgagatt ttttactctt ggatcaatta ctgcacagcc agtaaaaatt    25320
gacaatgctt ctcctgcaag tactgttcat gctacagcaa cgataccgct acaagcctca    25380
ctccctttcg gatggcttgt tattggcgtt gcatttcttg ctgttttca gagcgctacc    25440 aaaataattg cgctcaataa aagatggcag ctagccettt ataagggctt ccagttcatt    25500
tgcaatttac tgctgctatt tgttaccatc tattcacatc ttttgcttgt cgctgcaggt    25560
atggaggcgc aatttttgta cctctatgcc ttgatatatt ttctacaatg catcaacgca    25620
tgtagaatta ttatgagatg ttggctttgt tggaagtgca aatccaagaa cccattactt    25680
tatgatgcca actactttgt tgctggcac acacataact atgactactg tataccatat    25740
aacagtgtca cagatacaat tgtcgttact gaaggtgacg gcatttcaac accaaaactc    25800
aaagaagact accaaattgg tggttattct gaggataggc actcaggtgt taaagactat    25860
gtcgttgtac atggctattt caccgaagtt tactaccagc ttgagtctac acaaattact    25920
acagacactg gtattgaaaa tgctacattc ttcatcttta caagcttgt taaagaccca    25980 ccgaatgtgc aaatacacac aatcgacggc tcttcaggag ttgctaatcc agcaatggat    26040
ccaatttatg atgagccgac gacgactact agcgtgcctt tgtaagcaca agaaagtgag    26100
tacgaactta tgtactcatt cgtttcggaa gaaacaggta cgttaatagt taatagcgta    26160 cttcttttc ttgctttcgt ggtattcttg ctagtcacac tagccatcct tactgcgctt    26220
cgattgtgtg cgtactgctg caatattgtt aacgtgagtt tagtaaaacc aacggtttac    26280
gtctactcgc gtgttaaaaa tctgaactct ctgaaggag ttcctgatct tctggtctaa    26340
acgaactaac tattattatt attctgtttg gaactttaac attgcttatc atggcagaca    26400
acggtactat taccgttgag aagcttaaac aactcctgga acaatggaac ctagtaatag    26460
gtttcctatt cctagcctgg attatgttac tacaatttgc ctattctaat cggaacaggt    26520
ttttgtacat aataaagctt gttttcctct ggctcttgtg gccagtaaca cttgcttgtt    26580
```

```
ttgtgcttgc tgctgtctac agaattaatt gggtgactgg cgggattgcg attgcaatgg   26640
cttgtattgt aggcttgatg tggcttagct acttcgttgc ttccttcagg ctgtttgctc   26700
gtacccgctc aatgtggtca ttcaacccag aaacaaacat tcttctcaat gtgcctctcc   26760
gggggacaat tgtgaccaga ccgctcatgg aaagtgaact tgtcattggt gctgtgatca   26820
ttcgtggtca cttgcgaatg gccggacacc ccctagggcg ctgtgacatt aaggacctgc   26880
caaaagagat cactgtggct acatcacgaa cgctttctta ttacaaatta ggagcgtcgc   26940
agcgtgtagg cactgattca ggttttgctg catacaaccg ctaccgtatt ggaaactata   27000
aattaaatac agaccacgcc ggtagcaacg acaatattgc tttgctagta cagtaagtga   27060
caacagatgt ttcatcttgt tgacttccag gttacaatag cagagatatt gattatcatt   27120
atgaggactt tcaggattgc tatttggaat cttgacgtta taataagttc aatagtgaga   27180
caattattta agcctctaac taagaagaat tattcggagt tagatgatga agaacctatg   27240
gagttagatt atccataaaa cgaacatgaa aattattctc ttcctgacat tgattgtatt   27300
tacatcttgc gagctatatc actatcagga gtgtgttaga ggtacgactg tactactaaa   27360
agaaccttgc ccatcaggaa catacgaggg caattcacca tttcaccctc ttgctgacaa   27420
taaatttgca ctaacttgca ctagcacaca cttttgcttt tgcttgtgctg acggtactcg   27480
acatacctat cagctgcgtg caagatcagt ttcaccaaaa cttttcatca gacaagagga   27540
ggttcaacaa gagctctact cgccactttt tctcattgtt gctgctctag tatttttaat   27600
actttgcttc accattaaga gaaagacaga atgaatgagc tcactttaat tgacttctat   27660
ttgtgctttt tagcctttct gctattcctt gtttaataa tgcttattat attttggttt   27720
tcactcgaaa tccaggatct agaagaacct tgtaccaaag tctaaacgaa catgaaactt   27780
ctcattgttt tgacttgtat ttctctatgc agttgcatat gcactgtagt acagcgctgt   27840
gcatctaata aacctcatgt gcttgaagat ccttgtaagg tacaacacta ggggtaatac   27900
ttatagcact gcttggcttt gtgctctagg aaaggttta cctttcata gatggcacac   27960
tatggttcaa acatgcacac ctaatgttac tatcaactgt caagatccag ctggtggtgc   28020
gcttatagct aggtgttggt accttcatga aggtcaccaa actgctgcat ttagagacgt   28080
acttgttgtt ttaaataaac gaacaaatta aatgtctga taatggaccc caatcaaacc   28140
aacgtagtgc cccccgcatt acatttggtg gacccacaga ttcaactgac aataaccaga   28200
atggaggacg caatggggca aggccaaaac agcgccgacc ccaaggttta cccaataata   28260
ctgcgtcttg gttcacagct ctcactcagc atggcaagga ggaacttaga ttccctcgag   28320
gccagggcgt tccaatcaac accaatagtg gtccagatga ccaaattggc tactaccgaa   28380
gagctacccg acgagttcgt ggtggtgacg gcaaaatgaa agagctcagc cccagatggt   28440
acttctatta cctaggaact ggcccagaag cttcacttcc ctacggcgct aacaaagaag   28500
gcatcgtatg ggttgcaact gagggagcct tgaatacacc caaagaccac attggcaccc   28560
gcaatcctaa taacaatgct gccaccgtgc tacaacttcc tcaaggaaca acattgccaa   28620
aaggcttcta cgcagaggga agcagaggcg gcagtcaagc ctcttctcgc tcctcatcac   28680
gtagtcgcgg taattcaaga aattcaactc ctggcagcag taggggaaat tctcctgctc   28740
gaatggctag cggaggtggt gaaactgccc tcgcgctatt gctgctagac agattgaacc   28800
agcttgagag caaagtttct ggtaaaggcc aacaacaaca aggccaaact gtcactaaga   28860
aatctgctgc tgaggcatct aaaaagcctc gccaaaaacg tactgccaca aaacagtaca   28920
```

```
acgtcactca agcatttggg agacgtggtc cagaacaaac ccaaggaaat ttcggggacc    28980
aagacctaat cagacaagga actgattaca aacattggcc gcaaattgca caatttgctc    29040
caagtgcctc tgcattcttt ggaatgtcac gcattggcat ggaagtcaca ccttcgggaa    29100
catggctgac ttatcatgga gccattaaat tggatgacaa agatccacaa ttcaaagaca    29160
acgtcatact gctgaacaag cacattgacg catacaaaac attcccacca acagagccta    29220
aaaaggacaa aaagaaaaag actgatgaag ctcagccttt gccgcagaga caaaagaagc    29280
agcccactgt gactcttctt cctgcggctg acatggatga tttctccaga caacttcaaa    29340
attccatgag tggagcttct gctgattcaa ctcaggcata aacactcatg atgaccacac    29400
aaggcagatg ggctatgtaa acgttttcgc aattccgttt acgatacata gtctactctt    29460
gtgcagaatg aattctcgta actaaacagc acaagtaggt ttagttaact ttaatctcac    29520
atagcaatct ttaatcaatg tgtaacatta gggaggactt gaaagagcca ccacattttc    29580
atcgaggcca cgcggagtac gatcgagggt acagtgaata atgctaggga gagctgccta    29640 tatgaagag ccctaatgtg taaaattaat tttagtagtg ctatccccat gtgattttaa     29700
tagcttctta ggagaatgac                                                29720
```

MATERIALS AND METHODS FOR DETECTING CORONAVIRUS

FIELD OF THE INVENTION

The disclosure relates to test kits and methods for detecting the presence of coronavirus polynucleotides in a biological sample.

INCORPORATION BY REFERENCE

This application contains, as a separate part of the disclosure, a sequence listing in computer-readable form (filename: 55504_SeqListing.txt, 119,401 bytes, created Mar. 19, 2020), which is incorporated by reference in its entirety.

BACKGROUND

2019 Novel Coronavirus (2019-nCoV or SARS-CoV-2) is a virus recently identified as the cause of an outbreak of respiratory illness (Coronavirus disease 2019, COVID-19) with an increasing number of patients with severe symptoms and deaths. Typically, with most respiratory viruses, people are thought to be most contagious when they are most symptomatic (the sickest). With SARS-CoV-2, however, there have been reports of spread from an infected patient with no symptoms to a close contact. To monitor the presence of SARS-CoV-2 and to prevent its spread, it is highly important to detect infection as early and as fast as possible with a sensitive, reliable test, not only in the clinic, but also in remote locations, without the need for laboratory equipment.

Currently available Coronavirus diagnostic tests are based on the polymerase chain reaction (PCR) that usually require extensive technical infrastructure and know-how. (2,3) Thus, there is a need for a point-of-care (PoC) SARS-CoV-2 screening test that is selective, sensitive, reliable, and easily integrated in different settings around the world. Such a test must be simple, cost-effective, portable, able to be mass-produced, and easy to use in low resource settings

SUMMARY

In one aspect, described herein is a kit for the detection of a Coronavirus polynucleotide in a biological sample comprising (a) a primer pair and (b) a capture probe; wherein (a) and (b) are capable of detecting the presence of Coronavirus polynucleotides, if present, in the sample by recombinase polymerase amplification (RPA).

In some embodiments, the Coronavirus polynucleotide is a polynucleotide from SARS-CoV-2, CoV-229E, CoV-NL63, CoV-OC43, CoV-HKU1, SARS or MERS. In some embodiments, the Coronavirus polynucleotide is a polynucleotide from SARS-CoV-2.

In some embodiments, the primer pair comprises a first primer that is a tailed forward primer and a second primer is a reverse primer labeled with 6-carboxyfluorescein (FAM). In some embodiments, the primer pair comprises the nucleotide sequence set forth in SEQ ID NOs: 5 and 6. In some embodiments, the capture probe comprises a nucleotide sequence set forth in SEQ ID NO: 8, and is optionally biotinylated.

In some embodiments, the primer pair comprises a first primer that is a 5'-phosphorylated forward primer and a second primer is a reverse primer labeled with 6-carboxy-fluorescein (FAM). In some embodiments, the primer pair comprises the nucleotide sequence set forth in SEQ ID NOs: 4 and 6. In some embodiments, the capture probe comprises a nucleotide sequence set forth in SEQ ID NO: 7, and is optionally biotinylated.

In some embodiments, the kit further comprises a running buffer and optionally a test strip (e.g., filter paper (e.g., with capture line with streptavidin) or chitosan). In some embodiments, the running buffer comprises magnesium chloride and sodium chloride. In some embodiments, running buffer comprises about 420 mM sodium chloride and about 83 mM magnesium chloride, pH 6.5-8.5.

Also described herein is a method for detecting Coronavirus polynucleotides in a biological sample comprising (a) an amplifying step comprising adding the biological sample to a vessel containing a primer pair that is capable of amplifying Coronavirus polynucleotides, if present, in the biological sample, (b) combining the single-stranded amplified product with a running buffer comprising a capture probe that is capable of detecting the single-stranded amplified product to form a mixture, and incubating the mixture for a period of time in the vessel; and, (c) a detecting step comprising wicking the mixture into a test strip and visually detecting the capture probe on the test strip. In some embodiments, the primer pair comprises a first primer that is a tailed forward primer and a second primer is a reverse primer labeled with 6-carboxyfluorescein (FAM). In some embodiments, the primer pair comprises the nucleotide sequence set forth in SEQ ID NOs: 5 and 6. In some embodiments, the capture probe comprises a nucleotide sequence set forth in SEQ ID NO: 8, and is optionally biotinylated.

In another aspect, described herein is a method for detecting Coronavirus polynucleotides in a biological sample comprising (a) an amplifying step comprising adding the biological sample to a vessel containing a primer pair that is capable of amplifying Coronavirus polynucleotides, if present, in the biological sample, (b) digesting amplified Coronavirus polynucleotides in the vessel into a single-stranded amplified product before the combining step; (c) combining the single-stranded amplified product with a running buffer comprising a capture probe that is capable of detecting the single-stranded amplified product to form a mixture, and incubating the mixture for a period of time in the vessel; and, (d) a detecting step comprising wicking the mixture into a test strip and visually detecting the capture probe on the test strip. In some embodiments, the digesting step comprises adding an exonuclease to the vessel before the detecting step. In some embodiments, the exonuclease is lambda exonuclease. In some embodiments, the primer pair comprises a first primer that is a 5'-phosphorylated forward primer and a second primer is a reverse primer labeled with 6-carboxyfluorescein (FAM). In some embodiments, the primer pair comprises the nucleotide sequence set forth in SEQ ID NOs: 4 and 6. In some embodiments, the capture probe comprises a nucleotide sequence set forth in SEQ ID NO: 7, and is optionally biotinylated.

In some embodiments, the amplifying step does not comprise incubating the mixture at a temperature greater than about 37° C. In some embodiments, the amplifying step does not comprise incubating the mixture at a temperature greater than about 42° C. In some embodiments, the amplifying step comprises incubating the mixture for about 10 minutes to about 2 hours (e.g., 5 minutes, 0 minutes, 20 minutes, 30 minutes, 40 minutes, 50 minutes, 60 minutes, 70 minutes, 80 minutes, 90 minutes, 100 minutes, 110 minutes or 120 minutes).

The foregoing summary is not intended to define every aspect of the invention, and other features and advantages of the present disclosure will become apparent from the following detailed description, including the drawings. The present disclosure is intended to be related as a unified document, and it should be understood that all combinations of features described herein are contemplated, even if the combination of features are not found together in the same sentence, paragraph, or section of this disclosure. In addition, the disclosure includes, as an additional aspect, all embodiments of the invention narrower in scope in any way than the variations specifically mentioned above. With respect to aspects of the disclosure described or claimed with "a" or "an," it should be understood that these terms mean "one or more" unless context unambiguously requires a more restricted meaning. With respect to elements described as one or more within a set, it should be understood that all combinations within the set are contemplated. If aspects of the disclosure are described as "comprising" a feature, embodiments also are contemplated "consisting of" or "consisting essentially of" the feature. Additional features and variations of the disclosure will be apparent to those skilled in the art from the entirety of this application, and all such features are intended as aspects of the disclosure.

BRIEF DESCRIPTION OF THE FIGURES

FIG. 1 is an alignment of three Coronavirus polynucleotides from MERS(NC 019843.3) (SEQ ID NO: 11), SARS-CoV-2(MN908947.3) (SEQ ID NO: 12) and SARS (FJ882957.1) (SEQ ID NO: 13).

FIG. 2 provides gels showing the limit of detection of SARS-CoV-2 in the rapid RPA method.

FIG. 4A: Dilution of SARS-CoV-2 plasmid DNA and RPA using primers tailed-WHfw and FAM-WHrv, and separation by agarose gel. FIG. 4B: Dilution of SARS-CoV-2 plasmid DNA and RPA using primers tailedWHfw (SEQ ID NO: 6) and FAM-WHrv (SEQ ID NO: 5), and detection with paperstrips using Capture1 probe (SEQ ID NO: 7).

DETAILED DESCRIPTION

Figure 3:
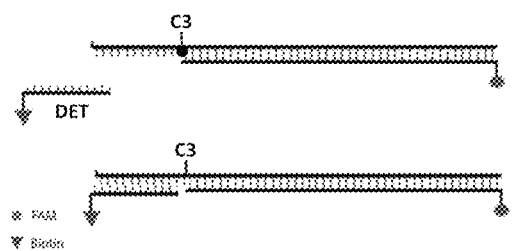
FIG. 3 is a schematic showing the detection of an RPA product with a single-stranded overhang at the 5'-end generated by using a tailed forward primer blocked with an internal C3 spacer.

The present disclosure provides kits and methods for detecting Coronavirus in biological samples that eliminate the need for laboratory equipment. Combination of isothermal reverse transcription recombinase polymerase amplification (RT-RPA) with a paper-based microfluidic analytical detection platform eliminates the need for equipment and high cost associated with PCR testing. The isothermal POC test described herein will amplify SARS-CoV-2 in a single tube for subsequent detection by paper-based lateral flow. It is contemplated that the assay described herein as a primary screening tool will be useful at airports/borders, local hospitals, doctors' offices and in remote setting around the world that often do not have access to clinical laboratories.

Described herein is an isothermal point of care method for the rapid detection of Coronavirus polynucleotides that works at a constant temperature (<42° C.) using recombinase polymerase amplification (RPA). RPA operates isothermally at temperatures between 25° C. and 42° C. and to prevent primer dimer formation and non-specific background amplification requires careful selection of primers and conditions for optimal amplification (20, 21). The polynucleotide amplification reactions can be run at constant temperatures (e.g., staying within five degrees from the starting temperature) that are near ambient or room temperature, for example, about 20° C. to about 37° C. The amplification reactions (and digestion by lambda exonuclease, if performed using a 5'-phosphorylated forward primer) can be run in a single reaction vessel. The test strip serves as a separation device that detects labelled capture probes hybridized to amplified Coronavirus nucleic acids based on capture lines (e.g., streptavidin) embedded in the test strip. Because the amplification can be completed in as little as 10-30 minutes, virtually immediate results can be provided on-site, rather than requiring days or weeks for results to be returned from a clinician or laboratory.

Also described herein are primer pairs that are capable of amplifying a Coronavirus polynucleotide. In some embodiments, the Coronavirus polynucleotide is SARS-CoV-2, CoV-229E, CoV-NL63, CoV-OC43, CoV-HKU1, SARS or MERS. In some embodiments, the primer pairs are capable of amplifying a Coronavirus polynucleotide in a sample from both humans and animals that may act as a carrier for SARS-CoV-2. To enable the detection of the amplified double-stranded RPA products, one of two methods can be employed associated with the present disclosure. In the first method, one primer in the primer pair is a tailed forward primer, and the other primer is a reverse primer labeled at the 5'-end with 6-carboxyfluorescein (FAM), generating single-stranded 5'-FAM-labelled RPA products.

In the second method, one primer in the primer pair is a 5'-phosphorylated forward primer and the other primer is a reverse primer labeled at the 5'-end with 6-carboxyfluorescein (FAM). In this second method, the double-stranded labelled RPA product is digested with lambda exonuclease, which preferentially digests 5'-phosphorylated DNA ends whereas the 5'-FAM ends are protected, generating single-stranded 5'-FAM-labelled RPA products.

The single-stranded products produced by either method can be detected by paper-based lateral flow assays (LFA) using biotinylated capture probes that are specific to each Coronavirus polynucleotide. Lateral flow assay conditions were developed that allow these probes to detect Coronavirus polynucleotides even at room temperature. Using this isothermal rapid detection method, amplification of Coronavirus polynucleotides at constant temperature (e.g., at about 37° C.) within short time (e.g., less than 1 hour) was achieved.

Detection Methods

In one aspect, the disclosure provides a method for detecting a Coronavirus polynucleotide in a biological sample comprising an amplifying step comprising adding the biological sample to a vessel containing a primer pair that is capable of amplifying the coronavirus polynucleotide, if present, in the biological sample, combining the amplified product with a running buffer comprising a capture probe that is capable of detecting the single-stranded amplified product, and incubating the mixture for a period of time in the vessel; and a detecting step comprising wicking the mixture onto a test strip and visually detecting the capture probe on the test strip. In some embodiments, single-stranded amplified products can be generated using tailed primers with an internal C3 spacer (3 hydrocarbons) (Jauset-Rubio et al., Scientific Reports 6:37732, 2016, the disclosure of which is incorporated by reference in its entirety). Such primers contain an additional sequence at the 5'-end separated by a C3 spacer from the sequence required for amplification. This additional sequence will not be copied during RPA since the C3 spacer blocks the polymerase. Hence, the single stranded amplified product can be detected by hybridizing a capture probe and subsequent lateral flow assay.

In another aspect, the disclosure provides a method for detecting a Coronavirus polynucleotide in a biological sample comprising an amplifying step comprising adding the biological sample to a vessel containing a primer pair that is capable of amplifying the coronavirus polynucleotide, if present, in the biological sample, digesting amplified coronavirus nucleic acids into a single stranded amplified product; combining the amplified product with a running buffer comprising a capture probe that is capable of detecting the single-stranded amplified product, and incubating the mixture for a period of time in the vessel; and a detecting step comprising wicking the mixture onto a test strip and visually detecting the capture probe on the test strip. In some embodiments, the digesting step further comprises adding an exonuclease to the vessel before the detecting step to generate a single stranded amplified product. In some embodiments, wherein the exonuclease is lambda exonuclease. In some embodiments, the digesting step does not comprise adding a exonuclease to the vessel before the detection step.

In some embodiments, the primer pair comprises a nucleotide sequence that is at least 90% identical (e.g., at least 90%, 91%, 92%, 93%, 94%, 95%, 96%, 97%, 98%, 99% or more identical) to a nucleotide sequence set forth in SEQ ID NOs: 1-6. In some embodiments, the primer pair comprises any combination of two primers comprises a nucleotide sequence set forth in SEQ ID NOs: 1-6. In some embodiments, the primer pair comprises the nucleotide sequences set forth in SEQ ID NOs: 5 and 6. In some embodiments, the nucleotide sequence set forth in SEQ ID NO: 6 is a tailed primer and the nucleotide sequence set forth in SEQ ID NO: 5 is labeled (e.g., with 6-carboxyfluorescein (FAM)).

In some embodiments, the primer pair comprises the nucleotide sequences set forth in SEQ ID NOs: 4 and 5. In some embodiments, the nucleotide sequence set forth in SEQ ID NO: 4 is a 5'phosphrylated forward primer and the nucleotide sequence set forth in SEQ ID NO: 5 is labeled (e.g., with 6-carboxyfluorescein (FAM)).

In some embodiments, the capture probe comprises nucleotide sequence that is at least 90% identical (e.g., at least 90%, 91%, 92%, 93%, 94%, 95%, 96%, 97%, 98%, 99% or more identical) to a nucleotide sequence set forth in any one of SEQ ID NO: 7 or SEQ ID NO: 8. In some embodiments, the capture probe comprises a nucleotide sequence set forth in any one of SEQ ID NO: 7 or SEQ ID NO: 8.

In some embodiments, the primer pair comprises SEQ ID NOs: 5 and 6 and the capture probe comprises SEQ ID NO: 7. In some embodiments, the primer pair comprises SEQ ID NOs: 4 and 5 and the capture probe comprises SEQ ID NO: 8.

The biological sample is, in various embodiments, obtained from a human or other mammalian subject, for example, by collecting a bodily fluid sample or swabbing a body orifice. The sample may be collected by, e.g., a health care worker or self-sampling. Alternatively, the biological sample is obtained from an environmental source, such as a water or soil or a contaminated surface, device or laboratory equipment. The biological sample may also be a food sample (e.g., a fluid or swab taken from food in order to, for example, detect contamination).

When the mixture of the biological sample and reagents is formed, if a Coronavirus polynucleotide is present in the biological sample, RPA amplification occurs and the capture probe hybridizes to the single-stranded copies of the amplified product to form a reporter complex.

Optionally, the capture probe is conjugated to a microparticle. The term "microparticle" refers to a particle comprising a diameter less than 100 micrometers and includes particles having a diameter less than one micrometer. Microparticles may be spherical (e.g., microbeads) or have an irregular shape, and may be composed of any of a number of substances, including gold and/or other metals, nylon and/or other polymers, magnetic compounds, and combinations thereof. In one aspect, the microparticle has a diameter less than about one micrometer. In various aspects, the microparticle is selected from a nylon microparticle, gold microparticle, or magnetic (e.g., paramagnetic) microparticle. Combinations of microparticles may also be used. Conjugation of the capture probe and microparticle can be achieved using any suitable method, such as covalent linkage. The labelled capture probe can be detected using lateral flow assay or by any other method suitable to detect it.

In the method using a primer pair comprising a 5'-phosphrylated forward primer, the running buffer used for the detection by lateral flow assay, in one aspect, comprises magnesium chloride and sodium chloride, optionally about 1 mM to about 100 mM magnesium chloride and about 1 mM to about 500 mM sodium chloride. In some embodiments, the running buffer comprises magnesium chloride at a concentration of about 1 mM, 5 mM, about 10 mM, about 15 mM, about 20 mM, about 25 mM, about 30 mM, about 35 mM, about 40 mM, about 45 mM, about 50 mM, about 55 mM, about 60 mM, about 70 mM, about 80 mM, about 81 mM, about 82 mM, about 83 mM, about 84 mM, about 85 mM, about 86 mM, about 87 mM, about 88 mM, about 89 mM, about 90 mM, about 91 mM, about 92 mM, about 93 mM, about 94 mM, about 95 mM, about 96 mM, about 97 mM, about 98 mM, about 99 mM or about 100 mM. In some embodiments, the running buffer comprises sodium chloride at a concentration of about 1 mM, 5 mM, about 10 mM, about 15 mM, about 20 mM, about 25 mM, about 30 mM, about 35 mM, about 40 mM, about 45 mM, about 50 mM, about 55 mM, about 60 mM, about 70 mM, about 80 mM, about 81 mM, about 82 mM, about 83 mM, about 84 mM, about 85 mM, about 86 mM, about 87 mM, about 88 mM, about 89 mM, about 90 mM, about 100 mM, about 200 mM, about 300 mM, about 400 mM, about 410 mM, about 415 mM, about 420 mM, about 425 mM, about 430 mM, about 435 mM, about 440 mM, about 445 mM, about 450 mM, about 455 mM, about 460 mM, about 465 mM, about 470 mM, about 475 mM, about 480 mM, about 485 mM, about 490 mM, about 495 mM, or about 500 mM. For example, in some embodiments, a 1× running buffer comprises about 83 mM magnesium chloride and about 420 mM sodium chloride, between pH 6.5 and 8.5.

In one aspect, the amplification step in either method described herein is performed at a temperature of less than about 42° C. (e.g., between about 25° C. and 42° C.), unlike traditional PCR reactions, which require laboratory equipment for temperature cycling to achieve temperatures greater than 90° C. Therefore, in one aspect, the amplification step does not comprise incubating the mixture at a temperature greater than about 42° C. In one aspect, the amplification step comprises incubating the mixture at a temperature between about 20° C. and about 42° C., for example, between about 22° C. and about 35° C., between about 23° C. and about 32° C., or between about 25° C. and about 30° C. In another aspect, the amplification step does not comprise incubating the mixture at a temperature greater than about 30° C. Optionally, the amplification step comprises incubating the mixture at a constant temperature of about 37° C. The term "constant temperature" refers to temperatures that are within ±5° C. of a reference temperature. In some embodiments, the amplification step comprises incubating the mixture at a temperature of about 37° C. or less for a time of about 10 minutes to about 2 hours, for example, about 10 minutes, about 20 minutes, about 30 minutes, about 40 minutes, about 50 minutes, about 60 minutes, about 90 minutes or about 2 hours. In some embodiments, the amplification step comprises incubating the mixture at a temperature of about 37° C. or less for a time of about 10 minutes to about 20 minutes.

In one aspect, either method of the disclosure described herein further comprises a detection step comprising wicking the mixture, e.g., via capillary action, into a test strip and visually detecting the capture probe. In some embodiments, the test strip is a paper strip, optionally comprising filter paper, such as Whatman #1 filter paper. The test strip optionally comprises pores having a diameter of about 5 micrometers to about 20 micrometers, for example, about 5 micrometers, about 10 micrometers, about 11 micrometers, about 12 micrometers, about 13 micrometers, about 14 micrometers, about 15 micrometers, or about 20 micrometers. Optionally, the test strip comprises a region comprising a capture line of streptavidin, or chitosan, which non-specifically binds polynucleotides and provides a control region or indicator of test completion. The test strip separates the components in the mixture based on size exclusion so that reporter probes hybridized to amplified polynucleotides, i.e., the reporter complexes, travel less along the length of the test strip than smaller, uncomplexed reporter probes. Thus, when a Coronavirus polynucleotide is present in the biological sample, a distinct band is visible near the bottom of the test strip, e.g., below an indicator of test completion, indicating that a Coronavirus polynucleotide is present in the biological sample. In contrast, a test strip dipped into a mixture containing only uncomplexed reporter probes exhibits a band farther up the test strip, e.g., at the mid-point of the strip or at an indicator of test completion, indicating that a Coronavirus polynucleotide is not present in the biological sample.

Kits

The disclosure also provides a kit for the detection of one or more Coronavirus polynucleotides in a biological sample, the kit comprising a primer pair and a biotinylated capture probe, wherein the primer pair and the capture probe are capable of detecting the Coronavirus polynucleotides, if present, in the sample. In some embodiments, the Coronavirus polynucleotide is a polynucleotide from SARS-CoV-2, CoV-229E, CoV-NL63, CoV-OC43, CoV-HKU1, SARS or MERS. In some embodiments, the primer pair and the capture probe are capable of identifying SARS-CoV-2.

In some embodiments, the primer pair comprises a nucleotide sequence that is at least 90% identical (e.g., at least 90%, 91%, 92%, 93%, 94%, 95%, 96%, 97%, 98%, 99% or more identical) to a nucleotide sequence set forth in SEQ ID NOs: 1-6. In some embodiments, the primer pair comprises any combination of two primers comprises a nucleotide sequence set forth in SEQ ID NOs: 1-6. In some embodiments, the primer pair comprises the nucleotide sequences set forth in SEQ ID NOs: 5 and 6. In some embodiments, the nucleotide sequence set forth in SEQ ID NO: 6 is a tailed primer and the nucleotide sequence set forth in SEQ ID NO: 5 is labeled (e.g., with 6-carboxyfluorescein (FAM)).

In some embodiments, the primer pair comprises the nucleotide sequences set forth in SEQ ID NOs: 4 and 6. In some embodiments, the nucleotide sequence set forth in SEQ ID NO: 4 is a 5'-phosphrylated forward primer and the nucleotide sequence set forth in SEQ ID NO: 5 is labeled (e.g., with 6-carboxyfluorescein (FAM)).

In some embodiments, the capture probe comprises nucleotide sequence that is at least 90% identical (e.g., at least 90%, 91%, 92%, 93%, 94%, 95%, 96%, 97%, 98%, 99% or more identical) to a nucleotide sequence set forth in SEQ ID NO: 7 or SEQ ID NO: 8. In some embodiments, the capture probe comprises a nucleotide sequence set forth in SEQ ID NO: 7 or SEQ ID NO: 8

In some embodiments, the primer pair comprises SEQ ID NOs: 5 and 6 and the capture probe comprises SEQ ID NO: 7. In some embodiments, the primer pair comprises SEQ ID NOs: 4 and 5 and the capture probe comprises SEQ ID NO: 8.

In some embodiments, the kit further comprises a test strip. In some embodiments, the test strip is a paper strip, optionally comprising filter paper, such as Whatman #1 filter paper. The test strip optionally comprises pores having a diameter of about 5 micrometers to about 20 micrometers, for example, about 5 micrometers, about 10 micrometers, about 11 micrometers, about 12 micrometers, about 13 micrometers, about 14 micrometers, about 15 micrometers, or about 20 micrometers. Optionally, the test strip comprises a region comprising a capture line such as streptavidin or chitosan, which non-specifically binds polynucleotides and provides a control region or indicator of test completion.

In some embodiments, the kit further comprises a running buffer for detection of products amplified with a 5'-phosphorylated forward primer by lateral flow assay. In some embodiments, the running buffer comprises magnesium chloride and sodium chloride, optionally about 1 mM to about 100 mM magnesium chloride and about 100 mM to about 500 mM sodium chloride. In some embodiments, the running buffer comprises magnesium chloride at a concentration of about 1 mM, 5 mM, about 10 mM, about 15 mM, about 20 mM, about 25 mM, about 30 mM, about 35 mM, about 40 mM, about 45 mM, about 50 mM, about 55 mM, about 60 mM, about 70 mM, about 80 mM, about 81 mM, about 82 mM, about 83 mM, about 84 mM, about 85 mM, about 86 mM, about 87 mM, about 88 mM, about 89 mM, about 90 mM, about 91 mM, about 92 mM, about 93 mM, about 94 mM, about 95 mM, about 96 mM, about 97 mM, about 98 mM, about 99 mM or about 100 mM. In some embodiments, the running buffer comprises sodium chloride at a concentration of about 1 mM, 5 mM, about 10 mM, about 15 mM, about 20 mM, about 25 mM, about 30 mM, about 35 mM, about 40 mM, about 45 mM, about 50 mM, about 55 mM, about 60 mM, about 70 mM, about 80 mM, about 81 mM, about 82 mM, about 83 mM, about 84 mM, about 85 mM, about 86 mM, about 87 mM, about 88 mM, about 89 mM, about 90 mM, about 100 mM, about 200 mM, about 300 mM, about 400 mM, about 410 mM, about 415 mM, about 420 mM, about 425 mM, about 430 mM, about 435 mM, about 440 mM, about 445 mM, about 450 mM, about 455 mM, about 460 mM, about 465 mM, about 470 mM, about 475 mM, about 480 mM, about 485 mM, about 490 mM, about 495 mM, or about 500 mM. For example, in some embodiments, a 1× running buffer comprises about 83 mM magnesium chloride and about 420 mM sodium chloride, between pH 6.5 and 8.5.

All of the U.S. patents, U.S. patent application publications, U.S. patent applications, foreign patents, foreign patent applications and non-patent publications referred to in this specification, are incorporated herein by reference, in their entireties.

From the foregoing it will be appreciated that, although specific embodiments of the invention have been described herein for purposes of illustration, various modifications may be made without deviating from the spirit and scope of the invention.

The following Examples are provided to further illustrate aspects of the disclosure, and are not meant to constrain the disclosure to any particular application or theory of operation.

EXAMPLES

Materials and Methods
Primer Design:

A plasmid containing the entire N capsid gene was used to test several primers that are unique to SARS-CoV-2 (when compared to SARS and MERS) to specifically amplify SARS-CoV-2 DNA (IDT). The genomic RNA/DNA sequences of the three most relevant Coronaviruses (MERS (NC_019843.3); SARS-CoV-2 (MN908947.3); and SARS (FJ882957.1)) were aligned using CLUSTAL 0(1.2.4) multiple sequence alignment (FIG. 1). Similar to a strategy that was used by the CDC for generating PCR primers, a region of the N capsid gene was selected that was different between MERS, COVID-19 and SARS. Several RPA primers of 30 bp length were designed and tested using COVID-19 control plasmid containing the entire N gene (IDT) (Table 1).

TABLE 1

| Primer | SEQ ID NO: | Sequence |
|---|---|---|
| WHfw | 1 | 5'-TCTGATAATGGACCCCAAAATCAGCGAAAT-3' |
| WHry | 2 | 5'-ACGCCTTGTCCTCGAGGGAATTTAAGGTCT-3' |
| WHrv2 | 3 | 5'-GGTAAACCTTGGGGCCGACGTTGTTTTGAT-3' |
| p-WHfw | 4 | p-5'-TCTGATAATGGACCCCAAAATCAGCGA AAT-3' |
| FAM-WHrv | 5 | FAM-5'-ACGCCTTGTCCTCGAGGGAATTTAA GGTCT-3' |
| WHtailfw | 6 | 5'-GTTTTCCCAGTCAGAC-SpacerC3-TCTGATAATGGACCCCAAAATCAGCGAAAT-3' |
| WHDET1 | 7 | Biotin-5'-GCGATCAAAACAACG-3' |
| Capture1 | 8 | 5'-GTCGTGACTGGGAAAACTTTTTTTT-3'-Biotin-TEG |
| T7PCRfw | 9 | 5'-ATTCATCGATGATAATACGACTCACTATAGG AGGGTTGCGTTTGAGA-3' |
| T7PCRrv | 10 | 5'-TAATGCAGCTGGCACGACAGGT-3' |

Development of Tailed Primers:

Single-stranded RPA products can be generated using tailed primers with an internal C3 spacer (3 hydrocarbons). (11) Such primers contain an additional sequence at the 5'-end separated by a C3 spacer from the sequence required for amplification. This additional sequence will not be copied during RPA since the C3 spacer blocks the polymerase. (11) Hence, it can be detected by hybridizing a capture probe and subsequent lateral flow assay. The RPA product generated by these primers will be single-stranded at one end and FAM-labelled at the other, so that it can be captured and detected by lateral flow assay using a biotinylated capture probe complementary to the 5'-overhang present in tailed forward primer. Alternatively, both the forward and reverse primer can be used with an internal C3 spacer and with having two different tail sequences, that can be detected with two different capture probes labelled with Biotin (DETA) and FAM (DETB).

Isothermal Recombinase Polymerase Amplification:

Isothermal RPA amplification of Coronovirus DNA was essentially done according to the TwistAmp Basic RPA kit (TwistDX). Briefly, 2.4 μL forward primer (10 μM) and 2.4 μL reverse primer (10 μM) (Table 1), 29.5 rehydration buffer, CoV plasmids, and water (RT-PCR grade water (Invitrogen)) to a total volume of 47.5 μL were added to the freeze-dried reaction mixture and mixed by pipetting and centrifuged. The reaction was then started with 2.5 μL 280 mM Mg-Acetate and incubated for 20 min at 37° C. The RPA products were separated by a 2% agarose gel, the band with the correct size (approximately 150 bp) extracted with a gel extraction kit (Qiagen) and the HPV type confirmed by sequencing (Genewiz). Images of agarose gels containing Gel Red were acquired by an Azure Biosystems C200 Imaging system. For dilution experiments, plasmids or genomic DNA were serially diluted 1/10 with water (RT-PCR grade water (Invitrogen)) in DNA LoBind tubes (Eppendorf).

Lateral Flow Assay on Milenia Hybridetect Dipstick:

The single-stranded FAM-labeled SARS-CoV-2 RPA reaction product is spotted on the Hybridetect Dipstick, processed as described in the manufacturers' protocol (Milenia), and photographed. For capture, the running buffer is supplemented with 1 μL of the Capture probe (50 μM) (SEQ ID NO: 7 or SEq ID NO: 8) and vortexted, before addition of the loaded Dipstick Detection by Lateral Flow Assay:

To 8 microL of the RPA Product, 1 μL of Lambda exonuclease (NEB) and 1 μL 10× buffer was added and incubated for 20 min at 37° C. Then, 1 to 4 μL were spotted on the Hybridetect Dipstick, processed as described in the manufacturers' protocol (Milenia Biotec), and photographed. In some cases, if amplification was very efficient, that sample was dilutes with water before spotting on the Dipstick. For detection of SARS-CoV-2 products amplified using a 5'-phosphrorylated forward primer by lateral flow assay, the protocol was modified by adding to the running buffer (100 μL) 1 μL of detection probes (5'-biotinylated (SEQ ID NO: 4), 50 μM) (Table 1), 10 μL of 5 M NaCl (final 420 mM) and 10 μL 1M $MgCl_2$ (83 mM), and mixed by vortexing. The test strip was placed into the tube and lateral flow assay was performed for 5 min. The Dipsticks were photographed, and the bands were quantified using the AlphaEaseFC Software (Alphalnotech, San Leandro, Calif.).

Example 1—Plasmid Preparation for Generation of Capsid Gene N RNA

SARS-CoV-2 plasmid containing the N gene (IDT) was amplified using T7PCRfw (50 μM) and T7PCRrv primers (50 µM) and Q5 DNA polymerase (NEB). The PCR fragment was separated on a 1.5% agarose gel, isolated (Qiagen) and cut with ClaI and EcoRI for 2 hours, separated on a 1.5% agarose gel, and the ClaI/EcoRI fragment ligated back into the original plasmid cut also with ClaI/EcoRI. After transformation into NEB5alpha, the correct insert was checked by ClaI/EcoRI and confirmed by Sanger sequencing (Genewiz). The T7N plasmid DNA was generated using a maxiprep kit (Qiagen). 5 µg of plasmid T7N was linearized with PstI and used to generate N gene RNA using the HiScribe™ T7 Quick High Yield RNA Synthesis Kit according the manufacturers instruction (NEB). After DNae (RNasefree, NEB) digestion of template DNA, the RNA was purified using the Monrach RNA cleanup kit (NEB). The concentration of the N gene template COVID-19 RNA (1224 bp) was measured using a Spectrophotometer/FluorometerNano (DS-11 FX+, DeNovix) as 740 ng/µL, with a copy number of 1.530e+9 per ng or 2.541 fmol, and used in RPA reactions and paperstrip detection.

Example 2—RPA Method with DNA Templates

Dilute in DNA LoBind tubes (Eppendorf) 1 µL of plasmid SARS-CoV-2 (Integrated DNA Technology, IDT) (200000 copies) into 799 µL of PCR water (Invitrogen) to generate working stock for RPA (250 copies per µL). For two reactions dilute 10 of working stock plus 17.4 water (1250 copies final for one reaction), 8 of working stock plus 19.4 water (1000 copies), 6 µL of working stock plus 21.4 water (750 copies), 4 µL working stock plus 23.4 water (500 copies), 2 µL of working stock plus 25.4 water (250 copies), 1 of working stock plus 26.4 water (125 copies), 0.5 µL of working stock plus 26.9 water (62.5 copies), and 27.4 water (0 copies).

In a separate PCR tube strip, assemble at the wall of the tubes in this order 2.4 µL tailedWHfw primer (10 µM), 2.4 µL WHrv primer (10 µM), 29.5 Rehydration buffer, 13.2 of the above diluted samples and centrifuge. Add this solution to the RPA test strip (TwistDX) and pipette in and out 6 times. Add 2.5 µL MgAcetate to the wall just below the ring of the RPA test strip, centrifuge, vortex, centrifuge and incubate for 20 min at 37° C. Use 20 µL of this for 2% agarose gel, or 1 µL for paperstrip. To 100 µL of the running buffer of the paperstrip (Milenia) add 1 µL Capture1 probe (50 µM), mix and add the loaded paperstrip for 5 minutes.

Figure 4:
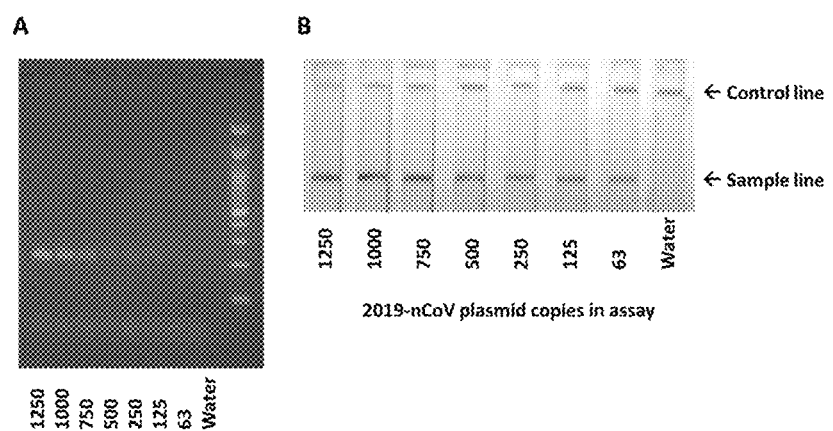
FIGS. 4A and 4B demonstrate that a primer pair comprising a tailed forward primer (tailedWHfw) and a FAM-labelled reverse primer (FAM-WHrv) were able to amplify COVID-19 plasmid with a detection limit of 60 copies on paperstrips using the RPA method.

The primers provided in Table 1 detected all 129 SARS-CoV-2 variants known to date (Koyama, T., Platt, D. & Parida, L. Variant analysis of COVID-19 genomes. Bull World Health Organ, 2020). These primers were able to detect SARS-CoV-2 with a detection limit of about 20-60 copies (FIG. 2). The best primer set (WHfw/WHrv, SEQ ID NOs: 1 and 2, respectively) was used to generate a tailed forward primer (tailedWHfw, SEQ ID NO: 6 and a FAM-labelled reverse primer (FAM-WHrv, SEQ ID NO: 5) (FIG. 3). Using a biotinylated capture probe (Capture1, SEQ ID NO: 8), these primers were able to amplify SARS-CoV-2 plasmid with a detection limit of 60 copies on paperstrips (FIG. 4). By using different sequences with the tail and the capture probe, this detection method can be multiplexed on paperstrips or in microtiter/microfluidic devices (e.g. multiplexed for SARS-CoV-2, SARS, MERS, etc.).

Alternatively, a 5'-phosphorylated forward primer (SEQ ID NO: 4), which can be digested after RPA by Lambda exonuclease to generate single-stranded FAM-labelled amplification products that can be detected with a capture probe (SEQ ID NO: 7).

Example 3—RPA Method with RNA Templates

Figure 5:
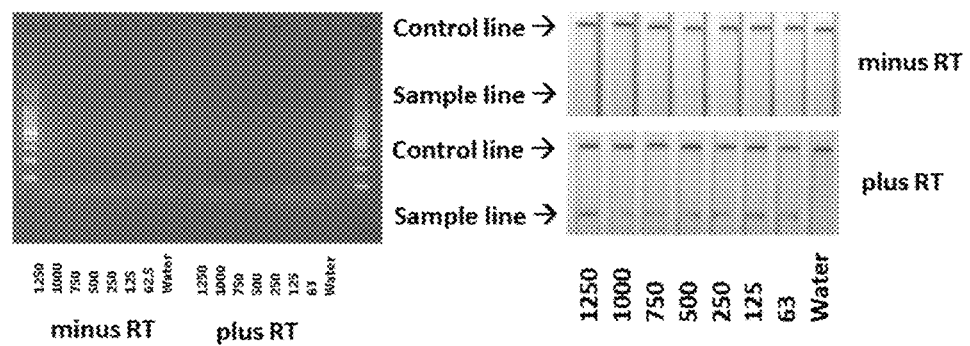
FIG. 5 shows amplification of low copy numbers RNA (1250-63 copies) of the N gene from SARS-CoV-2 by RT-RPA with Multiscribe reverse transcriptase using primers tailedWHfw (SEQ ID NO: 6) and FAM-WHrv (SEQ ID NO: 5) and detection with paperstrips using Capture1 probe (SEQ ID NO: 7).
Figure 6:
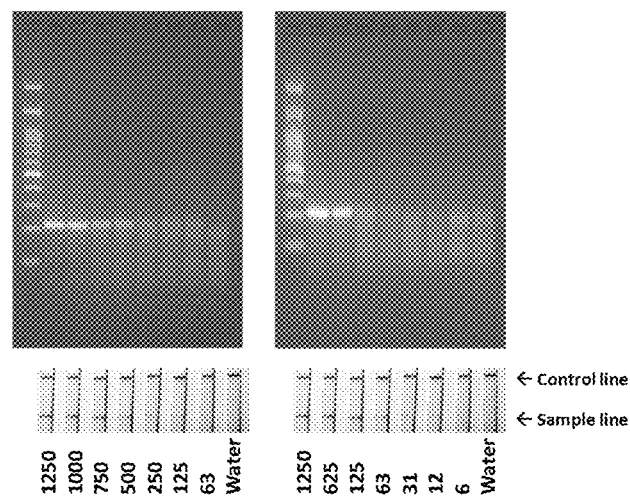
FIG. 6 shows amplification of plasmid DNA of the N gene from SARS-CoV-2 by RPA using primers phospho-WHfw (SEQ ID NO: 4) and FAM-WHrv (SEQ ID NO: 5), digestion with lambda exonuclease and detection with paperstrips using biotinylated WHDet1 (SEQ ID NO: 8).

The RNA generated from the plasmid T7N was diluted with Nuclease-free PCR water (Invitrogen) to 250 copies/µL and tested in reverse transcriptase recombinase polymerase amplification (RT-RPA). RPA reactions were assembled as before. Just before adding MgAcetate, 1 µL Multiscribe reverse transcriptase (50 U/µL, Applied Biosystems) was added to the RPA reaction. RPA products were visible on agarose gel when using high copy number RNA templates (>60000 copies), but not when using low copy number (<1250 copies). When detected on paperstrip, low copy number of RNA were detected only when adding reverse transcriptase, indicating that the test detects RNA of SARS-CoV-2 (FIGS. 5 and 6).

Example 4—Point of Care Assay Design for Testing of Respiratory Viruses

The above methods are used for samples such as oropharyngeal/nasopharyngeal swabs, sputum, bronchoalveolar lavages (BAL), urine or blood. Depending on the amounts and source (e.g., exhaled virus particles/droplets/fomites), such samples may require a purification/concentration step before the assay can be performed. An advantage of the assay design described below minimizes "hands-on" work from a clinician.

Balloon Test:

The patient exhales into a 5 inch clear latex balloon containing dried RPA assay components (e.g., at different positions), such as tailedWHfw primer (10 µM), WHrv primer (10 µM), and lyophilized RPA assay reagents. After inflation, the balloon is filled with 1× Rehydration buffer containing Mg Acetate and incubated for 20 min at 37° C. An amount of the buffer mix is used for 2% agarose gel, or for paperstrip. To 100 µL of the running buffer of the paperstrip (Milenia), add 1 µL Capture1 probe (50 µM), mix and added the loaded paperstrip to run for 5 minutes. Alternatively, directly detect RPA product in the balloon using Crystal violet dye or a fluorescent dye such as Ethidium bromide/Gel Red or Syber green.

Filter Test:

The patient exhales into a filter (such as an RNA filter (NEB)) connected to a 5 inch clear latex balloon. The latex filter is used directly for RPA by pipetting RPA assay components, tailedWHfw primer (10 µM), WHrv primer (10 µM), lyophilized RPA assay reagents, and an amount 1× Rehydration buffer containing Mg Acetate, and incubated for 20 min at 37° C. The filter is eluted using a syringe and X µL of the eluate is used for 2% agarose gel, or for paperstrip. To 100 µL of the running buffer of the paperstrip (Milenia), add 1 µL Capture1 probe (50 µM), mix and add the loaded paperstrip to run for 5 minutes. Alternatively, directly detect RPA product in filter using Crystal violet or a fluorescent dye such as Ethidium bromide or Syber green.

REFERENCES

1. Stringer, O. W., Andrews, J. M., Greetham, H. L. & Forrest, M. S. TwistAmp Liquid: a versatile amplifcation method to replace PCR. *Nature methods* 15, 1-3 (2018).
2. Zhang, N. et al. Recent advances in the detection of respiratory virus infection in humans. *J Med Virol*, doi: 10.1002/jmv.25674 (2020).
3. Sheridan, C. Coronavirus and the race to distribute reliable diagnostics. *Nature biotechnology* (2020).

4. Lu, W., Yuan, Q., Yang, Z. & Yao, B. Self-primed isothermal amplification for genomic DNA detection of human papillomavirus. *Biosensors & bioelectronics* 90, 258-263, doi:10.1016/j.bios.2016.10.024 (2017).
5. Zingg, J.-M. & Daunert, S. Trinucleotide Rolling Circle Amplification: A Novel Method for the Detection of RNA and DNA. *Methods and Protocols* 1, 15 (2018).
6. Barbieri, D., Venturoli, S., Rosl, F. & Rincon-Orozco, B. Detection of high-risk human papillomavirus type 16 and 18 using isothermal helicase-dependent amplification. *Diagnostic microbiology and infectious disease* 79, 178-182, doi:10.1016/j.diagmicrobio.2014.02.012 (2014).
7. Lin, J. et al. Colorimetric Detection of 23 Human Papillomavirus Genotypes by Loop-Mediated Isothermal Amplification. *Clin Lab* 63, 495-505, doi:10.7754/Clin.Lab.2016.160906 (2017).
8. Song, J. et al. Two-Stage Isothermal Enzymatic Amplification for Concurrent Multiplex Molecular Detection. *Clinical chemistry*, doi:10.1373/clinchem.2016.263665 (2017).
9. Ma, B. et al. Isothermal Method of a Recombinase Polymerase Amplification Assay for the Detection of Most Common High-Risk Human Papillomavirus Type 16 and Type 18 DNA. *Clin Lab* 63, 27-38, doi:10.7754/Clin.Lab.2016.160325 (2017).
10. Mahmoodi, P. et al. Early detection of cervical cancer based on high-risk HPV DNA-based genosensors: A systematic review. *BioFactors* 45, 101-117, doi:10.1002/biof.1465 (2019).
11. Jauset-Rubio, M. et al. Ultrasensitive, rapid and inexpensive detection of DNA using paper based lateral flow assay. *Scientific reports* 6, 37732, doi:10.1038/srep37732 (2016).
12. Banerjee, A. et al. Fast, Efficient, and Stable Conjugation of Multiple DNA Strands on Colloidal Quantum Dots. *Bioconjug Chem* 26, 1582-1589, doi:10.1021/acs.bioconjchem.5b00221 (2015).
13. Banerjee, A., Pons, T., Lequeux, N. & Dubertret, B. Quantum dots-DNA bioconjugates: synthesis to applications. *Interface Focus* 6, 20160064, doi:10.1098/rsfs.2016.0064 (2016).
14. Zhang, D. et al. A paper-based platform for detection of viral RNA. *The Analyst* 142, 815-823, doi:10.1039/c6an02452a (2017).
15. Rodriguez, N. M. et al. Paper-Based RNA Extraction, in Situ Isothermal Amplification, and Lateral Flow Detection for Low-Cost, Rapid Diagnosis of Influenza A (H1N1) from Clinical Specimens. *Analytical chemistry* 87, 7872-7879, doi:10.1021/acs.analchem.5b01594 (2015).

What is claimed is:

1. A kit for the detection Coronavirus polynucleotides in a biological sample comprising
   (a) a primer pair, wherein at least one primer of the primer pair comprises the sequence of SEQ ID NO: 1, wherein at least one of the primers of the primer pair is modified with an internal spacer or detectable label; and
   wherein (a) is capable of detecting Coronavirus polynucleotides, if present, in the sample by recombinase polymerase amplification (RPA).

2. The kit of claim 1, further comprising a running buffer.

3. The kit of claim 1 or claim 2, further comprising a test strip.

4. The kit of claim 1, wherein the Coronavirus polynucleotide is a polynucleotide from SARS-CoV-2, CoV-229E, CoV-NL63, CoV-OC43, CoV-HKU1, SARS or MERS.

5. The kit of claim 1, wherein Coronavirus polynucleotide is a polynucleotide from SARS-CoV-2.

6. The kit of claim 1, wherein the primer pair comprises the nucleotide sequence set forth in SEQ ID NOs: 5 and 6.

7. The kit of claim 1, wherein the primer pair comprises a first primer that is a tailed forward primer and a second primer is a reverse primer labeled with 6-carboxyfluorescein (FAM).

8. The kit of claim 1, wherein the primer pair comprises the nucleotide sequence set forth in SEQ ID NOs: 4 and 5.

9. The kit of claim 3, wherein the test strip comprises filter paper.

10. The kit of claim 3, wherein the test strip comprises chitosan.

11. A method for detecting Coronavirus polynucleotides in a biological sample comprising:
    (a) an amplifying step comprising adding the biological sample to a vessel containing a primer pair that is capable of amplifying Corona virus polynucleotides, if present, in the biological sample, wherein at least one primer of the primer pair comprises the sequence of SEQ ID NO: 1,
    (b) combining the single-stranded amplified product with a running buffer comprising a capture probe that is capable of detecting the single-stranded amplified product to form a mixture, and incubating the mixture for a period of time in the vessel; and,
    (c) a detecting step comprising wicking the mixture into a test strip and visually detecting the capture probe on the test strip.

12. A method for detecting Coronavirus polynucleotides in a biological sample comprising:
    (a) an amplifying step comprising adding the biological sample to a vessel containing a primer pair that is capable of amplifying Coronavirus polynucleotides, if present, in the biological sample, wherein at least one primer of the primer pair comprises the sequence of SEQ ID NO: 1,
    (b) digesting amplified Coronavirus polynucleotides in the vessel into a single-stranded amplified product before the combing step;
    (c) combining the single-stranded amplified product with a running buffer comprising a capture probe that is capable of detecting the single-stranded amplified product to form a mixture, and incubating the mixture for a period of time in the vessel; and,
    (d) a detecting step comprising wicking the mixture into a test strip and visually detecting the capture probe on the test strip.

13. The method of claim 12, wherein the digesting step comprises adding an exonuclease to the vessel before the detecting step.

14. The method of claim 13, wherein the exonuclease is lambda exonuclease.

15. The method of claim 11, wherein the amplifying step does not comprise incubating the mixture at a temperature greater than about 37° C.

16. The method of claim 11, wherein the amplifying step comprises incubating the mixture for about 10 minutes to about 2 hours.

17. The method of claim 11, wherein the amplifying step and/or the detecting step is performed without additional instrumentation.

18. The kit of claim 1 further comprising a capture probe.

19. The kit of claim 18, wherein the capture probe comprises a nucleotide sequence set forth in SEQ ID NO: 7.

20. The kit of claim 18, wherein the capture probe comprises a nucleotide sequence set forth in SEQ ID NO: 8.

21. The kit of claim 18, wherein the capture probe is biotinylated.

* * * * *